US007232888B2

(12) United States Patent
Begent et al.

(10) Patent No.: US 7,232,888 B2
(45) Date of Patent: Jun. 19, 2007

(54) ANTIBODIES AGAINST TUMOR SURFACE ANTIGENS

(75) Inventors: Richard J. H. Begent, London (GB); Kerry Ann Chester, London (GB); Christilyn P. Graff, Cambridge, MA (US); K. Dane Wittrup, Cambridge, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 302 days.

(21) Appl. No.: 10/609,671

(22) Filed: Jul. 1, 2003

(65) Prior Publication Data

US 2005/0147614 A1    Jul. 7, 2005

Related U.S. Application Data

(60) Provisional application No. 60/392,354, filed on Jul. 1, 2002.

(51) Int. Cl.
C07K 16/00 (2006.01)
(52) U.S. Cl. ............ 530/387.3; 530/350; 530/380; 530/385; 530/387.1; 530/387.7; 530/388.1; 424/134.1; 424/135.1; 424/141.1; 424/155.1; 424/142.1; 424/178.1; 424/85.1; 435/7.9; 435/188; 435/320.1; 435/54.1
(58) Field of Classification Search ........... 530/387.3, 530/350, 380, 385, 387.1, 387.7, 388.1; 424/134.1, 424/135.1, 141.1, 155.1, 142.1, 178.1, 85.1; 435/7.9, 188, 320.1, 54.1
See application file for complete search history.

(56) References Cited

U.S. PATENT DOCUMENTS 5,876,691 A * 3/1999 Chester et al. .......... 424/1.49

FOREIGN PATENT DOCUMENTS

| AU | 11251/92 | 1/1993 |
|---|---|---|
| CA | 2107513 | 4/1994 |
| EP | 0396387 A2 | 11/1990 |
| EP | 0396387 A3 | 11/1990 |
| EP | 0497585 A2 | 8/1992 |
| EP | 0501215 A2 | 9/1992 |
| EP | 0497585 A3 | 5/1993 |
| EP | 0501215 A3 | 8/1993 |
| EP | 0396387 B1 | 12/1993 |
| EP | 0590530 A2 | 4/1994 |
| EP | 0590530 A3 | 3/1997 |
| EP | 0590530 B1 | 4/2000 |
| EP | 0501215 B1 | 5/2000 |
| IE | 920630 A1 | 9/1992 |
| WO | WO 88/07378 | 10/1988 |
| WO | WO 91/01990 | 2/1991 |
| WO | WO 92/01059 | 1/1992 |
| WO | WO 92/15333 | 9/1992 |
| WO | WO 94/19466 | 9/1994 |
| WO | WO 95/15341 | 6/1995 |

OTHER PUBLICATIONS

Burgess et al, Journal of Cell Biology vol. 111 Nov. 1990 2129-2138.*
Lazar et al Molecular and Cellular Biology Mar. 1988 vol. 8 No. 3 1247-1252.*
Schwartz et al, Proc Natl Acad Sci USA vol. 84:6408-6411 (1987).*
Lin et al Biochemistry USA vol. 14:1559-1563 (1975).*
Paul, Fundamental Immunology, 3rd Edition, 1993, pp. 292-295.*
Rudikoff et al (Proc. Natl. Acad. Sci. USA 1982 vol. 79:1979-1983).*
Colman et al (Research in Immunology 1994, 145:33-36).*
Ibragimova and Eade (Biophysical Journal, Oct. 1999, vol. 77, pp. 2191-2198).*
Read et al. "Mutagenesis of single-chain antibody MFE 23 and its effect on affinity for CEA" Br. J. Cancer 71:57 (1995) (Abstract No. P132).
Zaccolo et al. "The effect of high-frequency random mutagenesis on in vitro protein evolution: A study on TEM-1 β-Lactamase" J. Mol. Biol. 285:775-783 (1999).
Adams, et al. "High affinity restricts the localization and tumor penetration of single-chain fv antibody molecules" Cancer Res. 61:4750-4755 (2001).
Baca et al. "Antibody humanization using monovalent phage display" J. Biol. Chem. 272:10678-10684 (1997).
Bagshawe et al. "Antibody-enzyme conjugates can generate cytotoxic drugs from inactive precursors at tumor sites" Antibody Immunocon. Radiopharm. 4:915-922 (1991).
Baulida et al. "All ErbB receptors other than the epidermal growth factor receptor are endocytosis impaired" J. Biol. Chem. 271:5251-5257 (1996).
Baxter et al. "Biodistribution of monoclonal antibodies: Scale-up from mouse to human using a physiologically based pharmacokinetic model" Cancer Res. 55:4611-4622 (1995).
Baxter et al. "Transport of fluid and macromolecules in tumors: III. Role of binding and metabolism" Microvasc. Res. 41:5-23 (1991).
Baxter et al. "Transport of fluid and macromolecules in tumors: IV. A microscopic model of the perivascular distribution" Microvasc. Res. 41:252-272 (1991).
Beers et al. "Immunotoxins with increased activity against epidermal growth factor receptor vIII-expressing cells produced by antibody phage display" Clin. Cancer Res. 6:2835-2843 (2000).
Begent et al. "Clinical evidence of efficient tumor targeting based on single-chain Fv antibody selected from a combinatorial library" Nat. Med. 2:979-984 (1996).

(Continued)

Primary Examiner—Sheela J. Huff
Assistant Examiner—Parithosh K. Tungaturthi
(74) Attorney, Agent, or Firm—Nixon & Vanderhye P.C.

(57) ABSTRACT

The present invention relates to improved antibodies against tumor surface antigens and their use in the treatment of tumors. Of particular interest are highly stable, humanized, high affinity antibodies against carcinoembryonic antigen (CEA), especially the antibody we have termed sm3E, which is derived from the scFv antibody MFE-23. Such antibodies have the potential for improved therapeutic efficacy.

6 Claims, 24 Drawing Sheets

OTHER PUBLICATIONS

Berk et al. "Direct in vivo measurement of targeted binding in a human tumor xenograft" Proc. Natl. Acad. Sci. USA, 94:1785-1790 (1997).
Bidart et al. "Kinetics of serum tumor marker concentrations and usefulness in clinical monitoring" Clin. Chem. 45:1695-1707 (1999).
Boder. "Yeast surface display for screening combinatorial polypeptide libraries" Nat. Biotechnol. 15:553-557 (1997).
Boder et al. "Optimal screening of surface-displayed polypeptide libraries" Biotechnol. Prog. 14:55-62 (1998).
Boder et al. "Directed evolution of antibody fragments with monovalent femtomolar antigen-binding affinity" Proc. Natl. Acad. Sci. USA 97:10701-10705 (2000).
Boehm et al. "Crystal structure of the anti-(carcinoembryonic antigen) single-chain Fv antibody MFE-23 and a model for antigen binding based on intermolecular contacts" Biochem. J. 346:519-528 (2000).
Boehm et al. "Structural models for carcinoembryonic antigen and its complex with the single-chain Fv antibody molecule MFE23" FEBS Lett. 475:11-16 (2000).
Bosslet et al. "Generation of bispecific monoclonal antibodies for two phase radioimmunotherapy" Br. J. Cancer 63:681-686 (1991).
Boxer et al. "Factors influencing variability of localisation of antibodies to carcinoembryonic antigen (CEA) in patients with colorectal carcinoma implications for radioimmunotherapy" Br. J. Cancer 65:825-831 (1992).
Burgess et al. "Possible dissociation of the heparin-binding and mitogenic activities of heparin-binding (acidic fibroblast) growth factor-1 from its receptor-binding activities by site-directed mutagenesis of a single lysine residue" J. Cell Biol. 111:2129-2138 (1990).
Casey et al. "Purification of bacterially expressed single chain Fv antibodies for clinical applications using metal chelate chromatography" J. Immunol. Meth. 179:105-116 (1995).
Chester et al. "Phage libraries for generation of clinically useful antibodies" Lancet 343:455-456 (1994).
Chester et al. "Clinical applications of phage-derived sFvs and sFv fusion proteins" Dis. Markers, 16:53-62 (2000).
Chester et al. "Recombinant anti-carcinoembryonic antigen antibodies for targeting cancer" Cancer Chemother. Pharmacol. 46:S8-12 (2000).
Chester et al. "Production of a high affinity anti-CEA scFv for colorectal tumour targeting" Abstract T306 J. Cellular Biochem. S18 D198 abstract at Keystone Symposium Lake Tahoe, CA (1994).
Clackson et al. "Makine antibody fragments using phage display libraries" Nature 352:624-628 (1991).
Cooke et al. "In vivo tumor delivery of a recombinant single-chain Fv::tumor necrosis factor: A fusion protein" Bioconjug. Chem. 13:7-15 (2002).
Daugherty et al. "Quantitative analysis of the effect of the mutation frequency on the affinity maturation of single chain Fv antibodies" Proc. Natl. Acad. Sci. USA 97:2029-2034 (2000).
Drewinko et al. "New monoclonal antibodies against colon cancer-associated antigens" Cancer Res. 46:5137-5143 (1986).
Dvorak et al. "Vascular permeability factor/vascular endothelial growth factor, microvascular hyperpermeability, and angiogenesis" Am. J. Pathol. 146:1029-1039 (1995).
Fujimori et al. "Modeling analysis of the global and microscopic distribution of immunoglobulin G, F(ab')$_2$, and Fab in tumors" Cancer Res. 49:5656-5663 (1989).
Fujimori et al. "A modeling analysis of monoclonal antibody percolation through tumors: A binding-site barrier" J. Nucl. Med. 31:1191-1198 (1990).
Gerlowski et al. "Microvascular permeability of normal and neoplastic tissues" Microvasc. Res. 31:288-305 (1986).
Gold et al. "Specific carcinoembryonic antigens of the human digestive system" J. Exp. Med. 122:467-481 (1965).
Goldenberg "Cancer imaging with CEA antibodies: Historical and current perspectives" Int. J. Biol. Markers 7:183-188 (1992).
Graham et al. "Post surgical surveillance of colon cancer" Ann. Surg. 228:59-63 (1998).
Green et al. "Mathematical model of antibody targeting: Important parameters defined using clinical data" Phys. Med. Biol. 45:1679-1693 (2000).
Groebe et al. "On the relation between size of necrosis and diameter of tumor spheroids" Int. J. Radiat. Oncol. Biol. Phys. 34:395-401 (1996).
Hammarstrom "The carcinoembryonic antigen (CEA) family: Structures, suggested functions and expression in normal and malignant tissues" Cancer Biol. 9:67-81 (1999).
Hammarstrom et al. "Antigenic sites in carcinoembryonic antigen" Cancer Res. 49:4852-4858 (1989).
Jackson et al. "Antigen specificity and tumor targeting efficiency of a human carcinoembryonic antigen-specific scFv and affinity-matured derivatives" Bri. J. Cancer 78:181-188 (1998).
Jain "Transport of molecules, particles, and cells in solid tumors" Annu. Rev. Biomed. Engin. 1:241-263 (1999).
Juweid et al. "Micropharmacology of monoclonal antibodies in solid tumors: Direct experimental evidence for a binding site barrier" Cancer Res. 52:5144-5153 (1992).
Knappik et al. "Fully synthetic human combinatorial antibody libraries (HuCAL) based on modular consensus frameworks and CDRs randomized with trinucleotides" J. Mol. Biol. 296:57-86 (2000).
Krol et al. "Available volume fraction of macromolecules in the extravascular space of a fibrosarcoma: Implications for drug delivery" Cancer Res. 59:4136-4141 (1999).
Kuan et al. "Increased binding affinity enhances targeting of glioma xenografts by EGFR vIII-specific scFv." Int. J. Cancer 88:962-969 (2000).
Kyriakos et al. "The fate of antibodies bound to the surface of tumor cells in vitro" Cancer Res. 52:835-842 (1992).
Lazar et al. "Transforming growth factor α: Mutation of aspartic acid 47 and leucine 48 results in different biological activities" Mol. Cell. Biol. 8:1247-1252 (1988).
Ledermann et al. "Repeated antitumour antibody therapy in man with suppression of the host response by cyclosporin A" Bv. J. Cancer 58:654-657 (1988).
Ledermann et al. "A phase-I study of repeated therapy with radiolabelled antibody to carcinoembryonic antigen using intermittent or continuous administration of cyclosporin A to suppress the immune response" Int. J. Cancer 47:659-664 (1991).
Low et al. "Mimicking somatic hypermutation: affinity maturation of antibodies displayed on bacteriophage using a bacterial mutator strain" J. Mol. Biol. 260:359-368 (1996).
Matsuoka et al. "Highly effective extraction of carcinoembryonic antigen with phosphatidylinositol-specific phospholipase C" Tumor Biol. 12:91-98 (1991).
Mayer et al. "Radioimmunoguided surgery in colorectal cancer using a genetically engineered anti-CEA single-chain Fv antibody" Clin. Cancer Res. 6:1711-1719 (2000).
Mendez et al. "Functional transplant of megabase human immunoglobulin loci recapitulates human antibody response in mice" Nat. Genet. 15:146-56 (1997).
Milenic et al. "Construction, binding properties, metabolism, and tumor targeting of a single-chain Fv derived from the pancarcinoma monoclonal antibody CC49" Cancer Res. 51:6363-6371 (1991).
Nap et al. "Immunohistochemistry of carcino-embryonic antigen in the embryo, fetus and adult" Tumor Biol. 9:145-153 (1988).
Nap et al. "Specificity and affinity of monoclonal antibodies against carcinoembryonic antigen" Cancer Res. 52:2329-39 (1992).
Nielsen et al. "Targeting of bivalent anti-ErbB2 diabody antibody fragments to tumor cells is independent of the intrinsic antibody affinity" Cancer Res. 60:6434-6440 (2000).
Osband et al. "Problems in the investigational study and clinical use of cancer immunotherapy" Immunol. Today 11:193-195 (1990).
Osbourn et al. "Generation of a panel of related human scFv antibodies with high affinities for human CEA" Immunotechnol. 2:181-196 (1996).
Osbourn et al. "Isolation of a panel of human anti-CEA single chain Fv from a large phage display library" Tumor Targeting 4:150-157 (1999).

Pedersen et al. "Comparison of surface accessible residues in human and murine immunoglobulin Fv domains. Implication for humanization of murine antibodies" J. Mol. Biol. 235:959-73 (1994).

Pedley et al. "The effect of second antibody clearance ont eh distribution and dosimetry of radiolabelled anti-CEA antibody in a human colonic tumor xenograft model" Int. J. Cancer 43:713-718 (1989).

Pedley et al. "Comparative radioimmunotherapy using intact or F(ab')$_2$ fragments of $^{131}$I anti-CEA antibody in a colonic xenograft model" Int. J. Cancer 68:69-73 (1993).

Pini et al. "Design and use of a phage display library. Human antibodies with subnanomolar affinity against a marker of angiogenesis eluted from a two-dimensional gel" J. Biol. Chem. 273:21769-21776 (1998).

Prall et al. "CD66a (BGP), an adhesion molecule of the carcinoembryonic antigen family, is expressed in epithelium, endothelium, and myeloid cells in a wide range of normal human tissues" J. Histochem. Cytochem. 44:35-41 (1996).

Press et al. "Retention of B-cell-specific monoclonal antibodies by human lymphoma cells" Blood 83:1390-1397 (1994).

Proba et al. "Antibody scFv fragments without disulfide bonds made by molecular evolution" J. Mol. Biol. 275:245-53 (1998).

Rader et al. "A phage display approach for rapid antibody humanization: Designed combinatorial V gene libraries" Proc. Natl. Acad. Sci. USA 95:8910-8915 (1998).

Roguska et al. "Humanization of murine monoclonal antibodies through variable domain resurfacing" Proc. Natl. Acad. Sci. USA 91:969-973 (1994).

Saga et al. "Targeting cancer micrometastases with monoclonal antibodies: A binding-site barrier" Proc. Natl. Acad. Sci. USA 92:8999-9003 (1995).

Saviranta et al. "Engineering the steroid-specificity of an anti-17β-estradiol Fab by random mutagenesis and competitive phage panning" Protein Eng. 11:143-52 (1998).

Schier et al. "Isolation of picomolar affinity anti-c-erbB-2 single-chain Fv by molecular evolution of the complementary determining regions in the center of the antibody binding site" J. Mol. Biol. 263:551-567 (1996).

Shi et al. "Subcellular distribution, synthesis, and release of carcinoembryonic antigen in cultured human colon adenocarcinoma cell lines" Cancer Res. 43:4045-4049 (1983).

Shusta et al. "Increasing the secretory capacity of *Saccharomyces cerevisiae* for production of single-chain antibody fragments" Nature Biotechnol. 16:773-777 (1998).

Shusta et al. "Yeast polypeptide fusion surface display levels predict thermal stability and soluble secretion efficiency" J. Mol. Biol. 292:949-956 (1999).

Shusta et al. "Directed evolution of a stable scaffold for T-cell receptor engineering" Nature Biotechnol. 16:754-759 (2000).

Stein et al. "Carcinoembryonic antigen as a target for radioimmunotherapy of human medullary thyroid carcinoma: Antibody processing, targeting, and experimental therapy with $^{131}$I and $^{90}$Y labeled MAbs" Cancer Biother. Radiopharm. 14:37-47 (1999).

Stemmer "Rapid evolution of a protein in vitro by DNA shuffling" Nature 370:389-391 (1994).

Sung et al. "Predicted and observed effects of antibody affinity and antigen density on monoclonal antibody uptake in solid tumors" Cancer Res. 52:377-384 (1992).

Tao et al. "Studies of aglycosylated chimeric mouse-human IgG: Role of carbohydrate in the structure and effector functions mediated by the human IgG constant region" J. Immunol. 143:2595-2601 (1989).

"The Fifth IBC International Conference on Antibody Engineering" La Jolla, California Dec. 7-10, 1994.

Thomas et al. "Effect of dose, molecular size, affinity, and protein binding on tumor uptake of antibody or ligand: A biomathematical model" Cancer Res. 49:3290-3296 (1989).

van Osdol et al. "An analysis of monoclonal antibody distribution in microscopic tumor nodules: Consequences of a 'binding site barrier'" Cancer Res. 51:477647-84 (1991).

Viti et al. "Increased binding affinity and valence of recombinant antibody fragments lead to improved targeting of tumoral angiogenesis" Cancer Res. 59:347-352 (1999).

Weinstein et al. "The pharmacology of monoclonal antibodies" Annu. N. Y. Acad. Sci. 507:199-210 (1987).

Weinstein et al. "Early intervention in cancer using monoclonal antibodies and other biological ligands: Micropharmacology and the 'binding site barrier'" Cancer Res. 52:2747s-2751s (1992).

Williams et al. "The immunoglobulin superfamily-domains for cell surface recognition" Annu. Rev. Immunol. 6:381-405 (1988).

Willuda et al. "High thermal stability is essential for tumor targeting of antibody fragments: Engineering of a humanized anti-epithelial glycoprotein-2 (epithelial cell adhesion molecule) single-chain Fv fragment" Cancer Res. 59:5758-5767 (1999).

Worthylake et al. "ErbB-2 amplification inhibits down-regulation and induces constitutive activation of both ErbB-2 and epidermal growth factor receptors" J. Biol. Chem. 274:8865-8874 (1999).

Winter et al. "Man-made antibodies" Nature 349:293-299 (1991).

Wu et al. "Tumor localization of anti-CEA single-chain Fvs: Improved targeting by non-covalent dimers" Immunotechnol. 2:21-36 (1996).

Yang et al. "CDR walking mutagenesis for the affinity maturation of a potent human anti-HIV-1 antibody into the picomolar range" J. Mol. Biol. 254:392-403 (1995).

* cited by examiner

A

B

SEQUENCE LISTING

```
<160> NUMBER OF SEQ ID NOS: 25

<210> SEQ ID NO 1
<211> LENGTH: 732
<212> TYPE: DNA
<213> ORGANISM: Mus musculus
<220> FEATURE:
<221> NAME/KEY: CDS
<222> LOCATION: (1)..(732)
<223> OTHER INFORMATION:

<400> SEQUENCE: 1 cag gtg aaa ctg cag cag tct ggg gca gaa ctt gtg agg tca ggg acc      48
Gln Val Lys Leu Gln Gln Ser Gly Ala Glu Leu Val Arg Ser Gly Thr
1               5                  10                  15 tca gtc aag ttg tcc tgc aca gct tct ggc ttc aac att aaa gac tcc      96
Ser Val Lys Leu Ser Cys Thr Ala Ser Gly Phe Asn Ile Lys Asp Ser
            20                  25                  30 tat atg cac tgg ttg agg cag ggg cct gaa cag ggc ctg gag tgg att     144
Tyr Met His Trp Leu Arg Gln Gly Pro Glu Gln Gly Leu Glu Trp Ile
        35                  40                  45
```

-continued

| | | |
|---|---|---|
| gga tgg att gat cct gag aat ggt gat act gaa tat gcc ccg aag ttc<br>Gly Trp Ile Asp Pro Glu Asn Gly Asp Thr Glu Tyr Ala Pro Lys Phe<br>    50                  55                  60 | | 192 |
| cag ggc aag gcc act ttt act aca gac aca tcc tcc aac aca gcc tac<br>Gln Gly Lys Ala Thr Phe Thr Thr Asp Thr Ser Ser Asn Thr Ala Tyr<br>65                  70                  75                  80 | | 240 |
| ctg cag ctc agc agc ctg aca tct gag gac act gcc gtc tat tat tgt<br>Leu Gln Leu Ser Ser Leu Thr Ser Glu Asp Thr Ala Val Tyr Tyr Cys<br>                85                  90                  95 | | 288 |
| aat gag ggg act ccg act ggg ccg tac tac ttt gac tac tgg ggc caa<br>Asn Glu Gly Thr Pro Thr Gly Pro Tyr Tyr Phe Asp Tyr Trp Gly Gln<br>                    100                 105                 110 | | 336 |
| ggg acc acg gtc acc gtc tcc tca ggt gga ggc ggt tca ggc gga ggt<br>Gly Thr Thr Val Thr Val Ser Ser Gly Gly Gly Gly Ser Gly Gly Gly<br>            115                 120                 125 | | 384 |
| ggc tct ggc ggt ggc gga tca gaa aat gtg ctc acc cag tct cca gca<br>Gly Ser Gly Gly Gly Gly Ser Glu Asn Val Leu Thr Gln Ser Pro Ala<br>130                 135                 140 | | 432 |
| atc atg tct gca tct cca ggg gag aag gtc acc ata acc tgc agt gcc<br>Ile Met Ser Ala Ser Pro Gly Glu Lys Val Thr Ile Thr Cys Ser Ala<br>145                 150                 155                 160 | | 480 |
| agc tca agt gta agt tac atg cac tgg ttc cag cag aag cca ggc act<br>Ser Ser Ser Val Ser Tyr Met His Trp Phe Gln Gln Lys Pro Gly Thr<br>                165                 170                 175 | | 528 |
| tct ccc aaa ctc tgg att tat agc aca tcc aac ctg gct tct gga gtc<br>Ser Pro Lys Leu Trp Ile Tyr Ser Thr Ser Asn Leu Ala Ser Gly Val<br>            180                 185                 190 | | 576 |
| cct gct cgc ttc agt ggc agt gga tct ggg acc tct tac tct ctc aca<br>Pro Ala Arg Phe Ser Gly Ser Gly Ser Gly Thr Ser Tyr Ser Leu Thr<br>        195                 200                 205 | | 624 |
| atc agc cga atg gag gct gaa gat gct gcc act tat tac tgc cag caa<br>Ile Ser Arg Met Glu Ala Glu Asp Ala Ala Thr Tyr Tyr Cys Gln Gln<br>210                 215                 220 | | 672 |
| agg agt agt tac cca ctc acg ttc ggt gct ggc acc aag ctg gag ctg<br>Arg Ser Ser Tyr Pro Leu Thr Phe Gly Ala Gly Thr Lys Leu Glu Leu<br>225                 230                 235                 240 | | 720 |
| aaa cgg gcg gcc<br>Lys Arg Ala Ala | | 732 |

<210> SEQ ID NO 2
<211> LENGTH: 244
<212> TYPE: PRT
<213> ORGANISM: Mus musculus

<400> SEQUENCE: 2

Gln Val Lys Leu Gln Gln Ser Gly Ala Glu Leu Val Arg Ser Gly Thr
1               5                   10                  15

Ser Val Lys Leu Ser Cys Thr Ala Ser Gly Phe Asn Ile Lys Asp Ser
                20                  25                  30

Tyr Met His Trp Leu Arg Gln Gly Pro Glu Gln Gly Leu Glu Trp Ile
            35                  40                  45

Gly Trp Ile Asp Pro Glu Asn Gly Asp Thr Glu Tyr Ala Pro Lys Phe
        50                  55                  60

Gln Gly Lys Ala Thr Phe Thr Thr Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Asn Glu Gly Thr Pro Thr Gly Pro Tyr Tyr Phe Asp Tyr Trp Gly Gln
            100                 105                 110

```
Gly Thr Thr Val Thr Val Ser Ser Gly Gly Gly Ser Gly Gly
        115                 120                 125

Gly Ser Gly Gly Gly Ser Glu Asn Val Leu Thr Gln Ser Pro Ala
    130                 135                 140

Ile Met Ser Ala Ser Pro Gly Glu Lys Val Thr Ile Thr Cys Ser Ala
145                 150                 155                 160

Ser Ser Ser Val Ser Tyr Met His Trp Phe Gln Gln Lys Pro Gly Thr
                165                 170                 175

Ser Pro Lys Leu Trp Ile Tyr Ser Thr Ser Asn Leu Ala Ser Gly Val
            180                 185                 190

Pro Ala Arg Phe Ser Gly Ser Gly Ser Gly Thr Ser Tyr Ser Leu Thr
        195                 200                 205

Ile Ser Arg Met Glu Ala Glu Asp Ala Ala Thr Tyr Tyr Cys Gln Gln
    210                 215                 220

Arg Ser Ser Tyr Pro Leu Thr Phe Gly Ala Gly Thr Lys Leu Glu Leu
225                 230                 235                 240

Lys Arg Ala Ala

<210> SEQ ID NO 3
<211> LENGTH: 867
<212> TYPE: DNA
<213> ORGANISM: Artificial Sequence
<220> FEATURE:
<223> OTHER INFORMATION: nucleic acid encoding a humanized murine
      antibody
<220> FEATURE:
<221> NAME/KEY: CDS
<222> LOCATION: (1)..(867)
<223> OTHER INFORMATION:

<400> SEQUENCE: 3 cca tac gac gtt cca gac tac gct ctg cag gct agt ggt ggt ggt ggt      48
Pro Tyr Asp Val Pro Asp Tyr Ala Leu Gln Ala Ser Gly Gly Gly Gly
1               5                   10                  15 tct ggt ggt ggt ggt tct ggt ggt ggt ggt tct gct agc caa gtt aaa      96
Ser Gly Gly Gly Gly Ser Gly Gly Gly Gly Ser Ala Ser Gln Val Lys
                20                  25                  30 ctg gaa cag tcc ggt gct gaa gtt gtc aaa cca ggt gct tcc gtg aag     144
Leu Glu Gln Ser Gly Ala Glu Val Val Lys Pro Gly Ala Ser Val Lys
            35                  40                  45 ttg tcc tgt aaa gcc tct ggt ttt aac atc aag gat tcg tat atg cat     192
Leu Ser Cys Lys Ala Ser Gly Phe Asn Ile Lys Asp Ser Tyr Met His
        50                  55                  60 tgg ttg aga caa ggg cca gga caa aga ttg gaa tgg att ggc tgg att     240
Trp Leu Arg Gln Gly Pro Gly Gln Arg Leu Glu Trp Ile Gly Trp Ile
65                  70                  75                  80 gat cca gag aat ggt gat act gag tac gct cct aaa ttt cag gga aag     288
Asp Pro Glu Asn Gly Asp Thr Glu Tyr Ala Pro Lys Phe Gln Gly Lys
                85                  90                  95 gct act ttt act acc gac act tcc gct aat acc gca tac ttg ggc tta     336
Ala Thr Phe Thr Thr Asp Thr Ser Ala Asn Thr Ala Tyr Leu Gly Leu
                100                 105                 110 tct tcc ttg aga cca gag gac act gcc gta tac tac tgc aac gaa ggg     384
Ser Ser Leu Arg Pro Glu Asp Thr Ala Val Tyr Tyr Cys Asn Glu Gly
            115                 120                 125 aca cca act ggt cct tac tat ttc gac tac tgg gga caa ggt acc tta     432
Thr Pro Thr Gly Pro Tyr Tyr Phe Asp Tyr Trp Gly Gln Gly Thr Leu
        130                 135                 140
```

-continued

```
gtt act gtc tct agc ggt ggc gga ggt tca ggc ggt gga ggg tct gga        480
Val Thr Val Ser Ser Gly Gly Gly Gly Ser Gly Gly Gly Gly Ser Gly
145             150                 155                 160 ggt ggc ggt agt gaa aat gtg ctg acc caa tct cca agc tcc atg tct        528
Gly Gly Gly Ser Glu Asn Val Leu Thr Gln Ser Pro Ser Ser Met Ser
                165                 170                 175 gct tct gtt ggc gat aga gta aac atc gct tgt agc gca tcc tct agt        576
Ala Ser Val Gly Asp Arg Val Asn Ile Ala Cys Ser Ala Ser Ser Ser
            180                 185                 190 gtc tca tat atg cac tgg ttt caa cag aag cca ggt aaa agc cca aag        624
Val Ser Tyr Met His Trp Phe Gln Gln Lys Pro Gly Lys Ser Pro Lys
        195                 200                 205 ttg tgg att tat tcg aca tcc aac ttg gct tct gga gtg cct tca agg        672
Leu Trp Ile Tyr Ser Thr Ser Asn Leu Ala Ser Gly Val Pro Ser Arg
    210                 215                 220 ttt tct ggt tcc ggc tca gga acc gat tat agt ttg act att agc tca        720
Phe Ser Gly Ser Gly Ser Gly Thr Asp Tyr Ser Leu Thr Ile Ser Ser
225                 230                 235                 240 atg cag cca gag gat gct gca acc tac tat tgc cag caa agg tcc tca        768
Met Gln Pro Glu Asp Ala Ala Thr Tyr Tyr Cys Gln Gln Arg Ser Ser
                245                 250                 255 tat cca ctg act ttc ggg ggt gga acg aag ttg gaa atc aag gct gca        816
Tyr Pro Leu Thr Phe Gly Gly Gly Thr Lys Leu Glu Ile Lys Ala Ala
            260                 265                 270 gcc gga tcc gaa caa aag ctt att tct gaa gag gac ttg taa tag ctc        864
Ala Gly Ser Glu Gln Lys Leu Ile Ser Glu Glu Asp Leu                Leu
        275                 280                 285 gag                                                                    867
Glu
```

<210> SEQ ID NO 4
<211> LENGTH: 285
<212> TYPE: PRT
<213> ORGANISM: Artificial Sequence
<220> FEATURE:
<223> OTHER INFORMATION: humanized murine antibody

<400> SEQUENCE: 4

```
Pro Tyr Asp Val Pro Asp Tyr Ala Leu Gln Ala Ser Gly Gly Gly Gly
1               5                   10                  15

Ser Gly Gly Gly Gly Ser Gly Gly Gly Gly Ser Ala Ser Gln Val Lys
                20                  25                  30

Leu Glu Gln Ser Gly Ala Glu Val Val Lys Pro Gly Ala Ser Val Lys
            35                  40                  45

Leu Ser Cys Lys Ala Ser Gly Phe Asn Ile Lys Asp Ser Tyr Met His
        50                  55                  60

Trp Leu Arg Gln Gly Pro Gly Gln Arg Leu Glu Trp Ile Gly Trp Ile
65                  70                  75                  80

Asp Pro Glu Asn Gly Asp Thr Glu Tyr Ala Pro Lys Phe Gln Gly Lys
                85                  90                  95

Ala Thr Phe Thr Thr Asp Thr Ser Ala Asn Thr Ala Tyr Leu Gly Leu
            100                 105                 110

Ser Ser Leu Arg Pro Glu Asp Thr Ala Val Tyr Tyr Cys Asn Glu Gly
        115                 120                 125

Thr Pro Thr Gly Pro Tyr Tyr Phe Asp Tyr Trp Gly Gln Gly Thr Leu
    130                 135                 140

Val Thr Val Ser Ser Gly Gly Gly Gly Ser Gly Gly Gly Gly Ser Gly
145                 150                 155                 160
```

```
Gly Gly Gly Ser Glu Asn Val Leu Thr Gln Ser Pro Ser Ser Met Ser
                165                 170                 175

Ala Ser Val Gly Asp Arg Val Asn Ile Ala Cys Ser Ala Ser Ser Ser
            180                 185                 190

Val Ser Tyr Met His Trp Phe Gln Gln Lys Pro Gly Lys Ser Pro Lys
        195                 200                 205

Leu Trp Ile Tyr Ser Thr Ser Asn Leu Ala Ser Gly Val Pro Ser Arg
    210                 215                 220

Phe Ser Gly Ser Gly Ser Gly Thr Asp Tyr Ser Leu Thr Ile Ser Ser
225                 230                 235                 240

Met Gln Pro Glu Asp Ala Ala Thr Tyr Tyr Cys Gln Gln Arg Ser Ser
                245                 250                 255

Tyr Pro Leu Thr Phe Gly Gly Gly Thr Lys Leu Glu Ile Lys Ala Ala
            260                 265                 270

Ala Gly Ser Glu Gln Lys Leu Ile Ser Glu Glu Asp Leu
        275                 280                 285

<210> SEQ ID NO 5
<211> LENGTH: 867
<212> TYPE: DNA
<213> ORGANISM: Artificial Sequence
<220> FEATURE:
<223> OTHER INFORMATION: nucleic acid encoding a humanized, affinity
      matured and stabilized murine antibody
<220> FEATURE:
<221> NAME/KEY: CDS
<222> LOCATION: (1)..(867)
<223> OTHER INFORMATION:

<400> SEQUENCE: 5 cca tac gac gtt cca gac tac gct ctg cag gct agt ggt ggt ggt ggt         48
Pro Tyr Asp Val Pro Asp Tyr Ala Leu Gln Ala Ser Gly Gly Gly Gly
1               5                   10                  15 tct ggt ggt ggt ggt tct ggt ggt ggt ggt tct gct agc caa gtt aaa         96
Ser Gly Gly Gly Gly Ser Gly Gly Gly Gly Ser Ala Ser Gln Val Lys
            20                  25                  30 ctg gaa cag tcc ggt gct gaa gtt gtc aaa cca ggt gct tcc gtg aag        144
Leu Glu Gln Ser Gly Ala Glu Val Val Lys Pro Gly Ala Ser Val Lys
        35                  40                  45 ttg tcc tgt aaa gcc tct ggt ttt aac atc aag gat tcg tat atg cat        192
Leu Ser Cys Lys Ala Ser Gly Phe Asn Ile Lys Asp Ser Tyr Met His
    50                  55                  60 tgg ttg aga caa ggg cca gga caa aga ttg gaa tgg att ggc tgg att        240
Trp Leu Arg Gln Gly Pro Gly Gln Arg Leu Glu Trp Ile Gly Trp Ile
65                  70                  75                  80 gat cca gag aat ggt gat acc gag tac gct cct aaa ttt cag gga aag        288
Asp Pro Glu Asn Gly Asp Thr Glu Tyr Ala Pro Lys Phe Gln Gly Lys
                85                  90                  95 gct act ttt act acc gac act tcc gct aat acc gca tac ttg ggc tta        336
Ala Thr Phe Thr Thr Asp Thr Ser Ala Asn Thr Ala Tyr Leu Gly Leu
            100                 105                 110 tct tcc ttg aga cca gag gac act gcc gta tac tac tgc aac gaa ggg        384
Ser Ser Leu Arg Pro Glu Asp Thr Ala Val Tyr Tyr Cys Asn Glu Gly
        115                 120                 125 aca cca act ggt cct tac tat ttc gac tac tgg gga caa ggt acc tta        432
Thr Pro Thr Gly Pro Tyr Tyr Phe Asp Tyr Trp Gly Gln Gly Thr Leu
    130                 135                 140 gtt act gtc tct agc ggt ggc gga ggt tca ggc ggt gga ggg tct gga        480
Val Thr Val Ser Ser Gly Gly Gly Gly Ser Gly Gly Gly Gly Ser Gly
145                 150                 155                 160
```

-continued

```
ggt ggc ggt agt gaa aat gtg ctg acc caa tct cca agc tcc atg tct    528
Gly Gly Gly Ser Glu Asn Val Leu Thr Gln Ser Pro Ser Ser Met Ser
            165                 170                 175 gtt tct gtt ggc gat aga gta acc atc gct tgt agc gca tcc tct agt    576
Val Ser Val Gly Asp Arg Val Thr Ile Ala Cys Ser Ala Ser Ser Ser
        180                 185                 190 gtc cca tat atg cac tgg ctt caa cag aag cca ggt aaa agc cca aag    624
Val Pro Tyr Met His Trp Leu Gln Gln Lys Pro Gly Lys Ser Pro Lys
    195                 200                 205 ttg ttg att tat ttg aca tcc aac ttg gct tct gga gtg cct tca agg    672
Leu Leu Ile Tyr Leu Thr Ser Asn Leu Ala Ser Gly Val Pro Ser Arg
210                 215                 220 ttt tct ggt tcc ggc tca gga acc gat tat agt ttg act att agc tca    720
Phe Ser Gly Ser Gly Ser Gly Thr Asp Tyr Ser Leu Thr Ile Ser Ser
225                 230                 235                 240 gtg cag cca gag gat gct gca acc tac tat tgc cag caa agg tcc tca    768
Val Gln Pro Glu Asp Ala Ala Thr Tyr Tyr Cys Gln Gln Arg Ser Ser
            245                 250                 255 tat cca ctg act ttc ggg ggt gga acg aag ttg gaa atc aag gct gca    816
Tyr Pro Leu Thr Phe Gly Gly Gly Thr Lys Leu Glu Ile Lys Ala Ala
        260                 265                 270 gcc gga tcc gaa caa aag ctt att tct gaa gag gac ttg taa tag ctc    864
Ala Gly Ser Glu Gln Lys Leu Ile Ser Glu Glu Asp Leu          Leu
    275                 280                 285 gag                                                                867
Glu
```

```
<210> SEQ ID NO 6
<211> LENGTH: 285
<212> TYPE: PRT
<213> ORGANISM: Artificial Sequence
<220> FEATURE:
<223> OTHER INFORMATION: humanized, affinity matured and
      stabilized murine antibody
<220> FEATURE:
<221> NAME/KEY: heavy chain CDR1
<222> LOCATION: (55)..(61)
<223> OTHER INFORMATION:
<220> FEATURE:
<221> NAME/KEY: heavy chain CDR2
<222> LOCATION: (81)..(86)
<223> OTHER INFORMATION:
<220> FEATURE:
<221> NAME/KEY: heavy chain CDR3
<222> LOCATION: (129)..(137)
<223> OTHER INFORMATION:
<220> FEATURE:
<221> NAME/KEY: light chain CDR1
<222> LOCATION: (190)..(194)
<223> OTHER INFORMATION:
<220> FEATURE:
<221> NAME/KEY: light chain CDR2
<222> LOCATION: (213)..(215)
<223> OTHER INFORMATION:
<220> FEATURE:
<221> NAME/KEY: light chain CDR3
<222> LOCATION: (254)..(259)
<223> OTHER INFORMATION:

<400> SEQUENCE: 6
```

```
Pro Tyr Asp Val Pro Asp Tyr Ala Leu Gln Ala Ser Gly Gly Gly Gly
1               5                   10                  15

Ser Gly Gly Gly Gly Ser Gly Gly Gly Ser Ala Ser Gln Val Lys
            20                  25                  30

Leu Glu Gln Ser Gly Ala Glu Val Val Lys Pro Gly Ala Ser Val Lys
        35                  40                  45
```

```
Leu Ser Cys Lys Ala Ser Gly Phe Asn Ile Lys Asp Ser Tyr Met His
 50                  55                  60

Trp Leu Arg Gln Gly Pro Gly Gln Arg Leu Glu Trp Ile Gly Trp Ile
 65                  70                  75                  80

Asp Pro Glu Asn Gly Asp Thr Glu Tyr Ala Pro Lys Phe Gln Gly Lys
                 85                  90                  95

Ala Thr Phe Thr Thr Asp Thr Ser Ala Asn Thr Ala Tyr Leu Gly Leu
            100                 105                 110

Ser Ser Leu Arg Pro Glu Asp Thr Ala Val Tyr Tyr Cys Asn Glu Gly
        115                 120                 125

Thr Pro Thr Gly Pro Tyr Tyr Phe Asp Tyr Trp Gly Gln Gly Thr Leu
    130                 135                 140

Val Thr Val Ser Ser Gly Gly Gly Gly Ser Gly Gly Gly Gly Ser Gly
145                 150                 155                 160

Gly Gly Gly Ser Glu Asn Val Leu Thr Gln Ser Pro Ser Ser Met Ser
                165                 170                 175

Val Ser Val Gly Asp Arg Val Thr Ile Ala Cys Ser Ala Ser Ser Ser
            180                 185                 190

Val Pro Tyr Met His Trp Leu Gln Gln Lys Pro Gly Lys Ser Pro Lys
        195                 200                 205

Leu Leu Ile Tyr Leu Thr Ser Asn Leu Ala Ser Gly Val Pro Ser Arg
    210                 215                 220

Phe Ser Gly Ser Gly Ser Gly Thr Asp Tyr Ser Leu Thr Ile Ser Ser
225                 230                 235                 240

Val Gln Pro Glu Asp Ala Ala Thr Tyr Tyr Cys Gln Gln Arg Ser Ser
                245                 250                 255

Tyr Pro Leu Thr Phe Gly Gly Gly Thr Lys Leu Glu Ile Lys Ala Ala
            260                 265                 270

Ala Gly Ser Glu Gln Lys Leu Ile Ser Glu Glu Asp Leu
        275                 280                 285

<210> SEQ ID NO 7
<211> LENGTH: 36
<212> TYPE: DNA
<213> ORGANISM: Artificial Sequence
<220> FEATURE:
<223> OTHER INFORMATION: Primer

<400> SEQUENCE: 7
gtcagtgcta gccaggtgaa actgcagcag tctggg                          36

<210> SEQ ID NO 8
<211> LENGTH: 39
<212> TYPE: DNA
<213> ORGANISM: Artificial Sequence
<220> FEATURE:
<223> OTHER INFORMATION: Primer

<400> SEQUENCE: 8
gttcacggat cctgctttca gctccagctt ggtgccagc                       39

<210> SEQ ID NO 9
<211> LENGTH: 30
<212> TYPE: DNA
<213> ORGANISM: Artificial Sequence
<220> FEATURE:
<223> OTHER INFORMATION: Oligonucleotide
```

```
<400> SEQUENCE: 9
gatcccatca ccatcatcac cattaatagc                                       30

<210> SEQ ID NO 10
<211> LENGTH: 30
<212> TYPE: DNA
<213> ORGANISM: Artificial Sequence
<220> FEATURE:
<223> OTHER INFORMATION: Oligonucleotide

<400> SEQUENCE: 10
tcgagctatt aatggtgatg atggtgatgg                                       30

<210> SEQ ID NO 11
<211> LENGTH: 24
<212> TYPE: DNA
<213> ORGANISM: Artificial Sequence
<220> FEATURE:
<223> OTHER INFORMATION: Primer

<400> SEQUENCE: 11
ggcagcccca taaacacaca gtat                                             24

<210> SEQ ID NO 12
<211> LENGTH: 23
<212> TYPE: DNA
<213> ORGANISM: Artificial Sequence
<220> FEATURE:
<223> OTHER INFORMATION: Primer

<400> SEQUENCE: 12
gttacatcta cactgttgtt atc                                              23

<210> SEQ ID NO 13
<211> LENGTH: 44
<212> TYPE: DNA
<213> ORGANISM: Artificial Sequence
<220> FEATURE:
<223> OTHER INFORMATION: Primer

<400> SEQUENCE: 13
ggtaaaagcc caaagttgtt gatttatttg acatccaact tggc                       44

<210> SEQ ID NO 14
<211> LENGTH: 44
<212> TYPE: DNA
<213> ORGANISM: Artificial Sequence
<220> FEATURE:
<223> OTHER INFORMATION: Primer

<400> SEQUENCE: 14
gccaagttgg atgtcaaata atcaacaac tttgggcttt tacc                        44

<210> SEQ ID NO 15
<211> LENGTH: 39
<212> TYPE: DNA
<213> ORGANISM: Artificial Sequence
<220> FEATURE:
<223> OTHER INFORMATION: Primer

<400> SEQUENCE: 15
gatagatgaa acatcgctgt tagcgcatcc tctagtgtc                             39
```

```
<210> SEQ ID NO 16
<211> LENGTH: 39
<212> TYPE: DNA
<213> ORGANISM: Artificial Sequence
<220> FEATURE:
<223> OTHER INFORMATION: Primer

<400> SEQUENCE: 16
gacactagag gatgcgctaa cagcgatgtt tactctatc                              39

<210> SEQ ID NO 17
<211> LENGTH: 36
<212> TYPE: DNA
<213> ORGANISM: Artificial Sequence
<220> FEATURE:
<223> OTHER INFORMATION: Primer

<400> SEQUENCE: 17
ggatgctgca acctactatg cccagcaaag gtcctc                                 36

<210> SEQ ID NO 18
<211> LENGTH: 36
<212> TYPE: DNA
<213> ORGANISM: Artificial Sequence
<220> FEATURE:
<223> OTHER INFORMATION: Primer

<400> SEQUENCE: 18
gaggaccttt gctgggcata gtaggttgca gcatcc                                 36

<210> SEQ ID NO 19
<211> LENGTH: 34
<212> TYPE: DNA
<213> ORGANISM: Artificial Sequence
<220> FEATURE:
<223> OTHER INFORMATION: Primer

<400> SEQUENCE: 19
ctctatcgcc aacagaaaca gacatggagc ttgg                                   34

<210> SEQ ID NO 20
<211> LENGTH: 32
<212> TYPE: DNA
<213> ORGANISM: Artificial Sequence
<220> FEATURE:
<223> OTHER INFORMATION: Primer

<400> SEQUENCE: 20
gttggcgata gatgaaccat cgcttgtagc gc                                     32

<210> SEQ ID NO 21
<211> LENGTH: 32
<212> TYPE: DNA
<213> ORGANISM: Artificial Sequence
<220> FEATURE:
<223> OTHER INFORMATION: Primer

<400> SEQUENCE: 21
gcgcatcctc tagtgtccca tatatgcact gg                                     32

<210> SEQ ID NO 22
<211> LENGTH: 34
<212> TYPE: DNA
<213> ORGANISM: Artificial Sequence
<220> FEATURE:
<223> OTHER INFORMATION: Primer
```

```
<400> SEQUENCE: 22
gtttgactat tagctcagtg cagccagagg atgc                                    34

<210> SEQ ID NO 23
<211> LENGTH: 32
<212> TYPE: DNA
<213> ORGANISM: Artificial Sequence
<220> FEATURE:
<223> OTHER INFORMATION: Primer

<400> SEQUENCE: 23
cgaagggaca ccagctggtc cttactattt cg                                      32

<210> SEQ ID NO 24
<211> LENGTH: 32
<212> TYPE: DNA
<213> ORGANISM: Artificial Sequence
<220> FEATURE:
<223> OTHER INFORMATION: Primer

<400> SEQUENCE: 24
cgaaatagta aggaccagct ggtgtccctt cg                                      32

<210> SEQ ID NO 25
<211> LENGTH: 5
<212> TYPE: PRT
<213> ORGANISM: Artificial Sequence
<220> FEATURE:
<223> OTHER INFORMATION: light chain CDR1 of a humanized, affinity
      matured and stabilized murine antibody

<400> SEQUENCE: 25

Ser Ser Ser Val Ser
1               5
```

ANTIBODIES AGAINST TUMOR SURFACE ANTIGENS

This application claims priority to provisional application Ser. No. 60/392,354, filed Jul. 1, 2002, the contents of which are incorporated herein their entirety.

FIELD OF THE INVENTION

The present invention relates to improved antibodies against tumor surface antigens and their use in the treatment of tumors. Of particular interest are highly stable, humanized, high affinity antibodies against carcinoembryonic antigen (CEA), especially the antibody we have termed sm3E, which is derived from the scFv antibody MFE-23 Such antibodies have the potential for improved therapeutic efficacy.

BACKGROUND OF THE INVENTION

Treatment of Cancer with Antibodies, and Tumor Targeting of Antibodies

Antibodies have been used to treat cancer for many years. There are currently 5 antibodies approved by the FDA as cancer therapeutics, more than ten in Phase III clinical trials, and several hundred more in Phase II and Phase I trials. Antibodies act to remove cancerous cells through several effector mechanisms. For antibodies that are fully human or chimeric, the Fc portion of the molecule can efficiently activate and interact with the human immune system. By this method, cells can be destroyed by soluble components of the immune system (complement) or through ADCC-mediated cell killing. Additionally, binding of the antibody to the target antigen can initiate a biological response that can lead to apoptosis. Finally, antibody molecules can be used as delivery vehicles to transport therapeutic moieties such as radioisotopes, toxins, or enzymes.

Tumor targeting by antibodies is a complex process that involves circulation and clearance from the bloodstream, diffusion or convection into bulk tumors or micrometastases, binding and release of antigen, and metabolism of antigen/antibody complexes. In order to better understand the processes that influence treatment success, several mathematical models have been developed to analyze the distribution, retention, and removal of full antibody molecules and antibody fragments from solid tumors (Thomas et al., 1989, Sung et al., 1992, van Osdol et al, 1991, Baxter et al., 1995). Most have found there to be an affinity ceiling for uniform penetration and retention. Weinstein and colleagues first proposed the idea of a "binding site barrier" in 1987 (Weinstein et al., 1987). This hypothesis states that antibodies with extremely high affinity would bind antigens at the periphery of the tumor first, which would act as a barrier to further penetration within the tumor. This would result in heterogeneous distribution of the antibody and consequently ineffective treatment. Several additional papers have been published which support this hypothesis with mathematical models (Fujimori et al., 1989, Fujimori et al., 1990, van Osdol et al., 1991, Weinstein and van Osdol, 1992). Subsequent experimental studies have confirmed the existence of this phenomenon (Juweid et al., 1992). Tumor microenvironment can also cause unexpected hindrances. While blood vessels may be more permeable to solute transfer in the tumor (Dvorak et al., 1995, Gerlowski and Jain, 1986), the tumor in general may be less vascularized (Jain, 1999). Tumors also have a high interstitial pressure, which prevents migration of macromolecules into them. Jain et al. have carefully examined the unusual pressure and convection patterns in bulk tumors both experimentally and by mathematical modeling, and have found surprising phenomena such as temporary reverse flows out of tumor tissue.

The first generation of therapeutic antibodies consisted of entire IgG molecules, the format naturally utilized by the mammalian immune system. However, protein engineering technologies have been developed for a wide variety of antibody fragments varying in size and valency. These smaller fragments are more highly diffusible, and therefore penetrate tumor tissue more rapidly. With the advent of directed evolution and display technologies, it is now possible to engineer extremely high affinity antibody fragments. In some instances, experimental biodistribution data indicates limiting returns in targeting as affinity is progressively improved.

Carcinoembryonic Antigen (CEA) and Antibodies thereto in Cancer Treatment

Carcinoembryonic antigen (CEA) has long been identified as a tumor associated antigen (Gold and Freedman, 1965). Originally classified as a protein expressed only in fetal tissue, CEA has now been identified as present in several normal adult tissues. These tissues are primarily epithelial in origin, including cells of the colon, stomach, tongue, esophagus, cervix, sweat glands, and prostrate (Nap et al., 1988, Nap et al., 1992, Prall et al., 1996). Tumors of epithelial origin, as well as their metastases, contain CEA as a tumor associated antigen. While presence of CEA itself does not indicate transformation to a cancerous cell, the distribution of CEA is indicative. In normal tissue, CEA is restricted to the apical surface of the cell (Hammarstrom, 1999). As an example of normal tissue expression, a healthy adult excretes 50–70 mg of CEA in feces per day (Matsuoka et al., 1991). In contrast to normal tissue, cancerous cells tend to express CEA over the entire surface (Hammarstrom, 1999).

Carcinoembryonic antigen is a 180,000 kDa protein with approximately 50% carbohydrate content. It has seven domains, with a single N-terminal Ig variable domain and six domains homologous to the Ig constant domain (Williams and Barclay, 1988). Several distinct epitopes have been identified in CEA (Hammarstrom et al., 1989). Multiple monoclonal antibodies have been raised against CEA for research purposes and as diagnostic tools (Nap et al., 1992). More recently, single chain antibody fragments have been isolated from phage display libraries to be used in radioimmunodetection and radioimmunotherapy (Chester et al., 1994; Osbourn et al., 1999). Of particular interest is the MFE-23 scFv (Chester et al., 1994, WO95/15431, U.S. Pat. No. 5,876,691 to Chester et al.). This antibody fragment has been shown to effectively target colon cancer for radioimmunodetection in viva (Begent et al., 1996). MFE-23 has also been used in radioimmunoguided surgery of colorectal cancer (Mayer et al., 2000). MFE-23 has been produced as a fusion protein to carboxypeptidase G2 (CPG2) and TNFα as well. Both fusions have shown promise in therapy (Chester et al., 2000; Chester et al., 2000, Cooke et al., 2002).

SUMMARY OF THE INVENTION

As discussed above, the prevailing view in the literature is that increasing affinity of an antibody to a tumor antigen such as CEA above a certain level will not increase its efficacy, and may even result in ineffective treatment. However, we find that technological advances allowing the engineering of extremely high affinity antibody fragments raise new questions about the therapeutic payout of such antibodies and have set out to investigate the relationship between affinity and efficacy.

In order to better understand what processes are responsible for this limit, and if it can be overcome, a model of antibody penetration into tumor microspheroids was constructed. Microspheroids were modelled because they are a good physiological representation for micrometastases, which occur quite frequently in several forms of cancer. For example, up to 70% of patients with colorectal cancer eventually develop liver metastases (see www dot livertumor dot ora). Our model incorporates diffusion, antibody/antigen binding, and antibody/antigen complex degradation. Convection was explicitly not incorporated into the model. Through analysis of the simulation results and comparison to published experimental data, our goal was to understand the key variables for loading of the antibody and maximal tumor retention.

An appreciation that the antibody penetrates a tumor as a moving front allowed for comparison to the "shrinking core model" (SCM), derived to model particulate combustion or catalyst regeneration in classical chemical engineering literature. The SCM provides a simple analytical method that will be useful for predicting the effects of altered antibody pharmacokinetics, antibody molecular weight, antigen turnover rate, antigen expression level, and micrometastases size on antibody penetration and retention. We were thus able to discern the key variables for loading of the antibody and maximal tumor retention.

There are several key variables for retention of the antibody in the tumor. Stability of the antigen is of critical importance. For example, an antibody will not remain bound to an antigen that has been internalized and degraded. Also, the antibody should be engineered to bind the antigen with an off-rate less than or equal to the degradation rate of the antigen. Optimal loading favors the use of highly diffusible, small antibody fragments. Additionally and significantly, we have found that affinity does not restrict penetration for antibodies with a $K_D$<1 nM. This is counter to the accepted thinking in the field.

This theoretical grounding enables us to apply current techniques in protein engineering to produce improved anti-tumour antibodies with greater efficacy. We selected the MFE-23 scFv antibody to CEA (Chester et al., supra) as a target for improvement. In this study, MFE-23 was engineered to increase the retention time of the antibody in the tumor relative to normal tissue. This was accomplished through partial humanization of MFE-23, and maturation of the affinity and stability of the scFv.

Since MFE-23 was isolated from a murine phage library, there exists the possibility that its administration elicits an immune response in humans. This could in turn decrease the lifetime of the antibody in circulation. In order to reduce the likelihood of immunogenicity, the antibody was resurfaced to present a more "human" Fv framework surface (Pedersen et al., 1994; Roguska et al., 1994, and see also Boehm et al., 2000). Equilibrium titration verified that our resurfacing resulted in no detectable change in CEA binding affinity. We termed this resurfaced scFv hMFE.

We then addressed the affinity of MFE-23. We predict that increased affinity of the hMFE scFv will increase retention time of the antibody in a tumor, on the basis of the mathematical modelling detailed herein. A critical parameter determining tumor retention is the off-rate ($k_{off}$). After two rounds of mutagenesis and screening, several variants of hMFE were isolated which showed a 10-fold, 100-fold, and 1000-fold improvement in the off-rate over the original scFv, hMFE. This series of scFvs will enable us to confirm the impact of increased affinity on efficacy in anti-CEA tumor therapy. The greatest improvement corresponds to a half-life for binding to CEA of approximately 7 days (versus 10 minutes for hMFE). The two mutations of greatest interest in this regard are both in the light chain. The change that led to the greatest improvement in affinity, $SV_L50L$, is in the CDR 2 loop of the light chain. From inspection of the crystal structure, the side chain of this residue protrudes into the cavity where contact with the antigen may occur. The other mutation that increased the affinity is $FV_L36L$. It is not in a CDR loop and occurs at the interface of the light and heavy chain, directly below this cavity. Significantly, the off-rate achieved in this study is amongst the slowest known for antibody-protein antigen interactions.

A further parameter addressed in our study was the stability of the scFv. In order to function in a therapeutic setting, the scFv must be resistant to thermal denaturation at 37° C. (Willuda et al., 1999). Furthermore, stability has been shown to correlate closely with expression efficiency (Shusta et al., 1999), and the affinity matured hMFE mutants were found to express poorly. Our affinity improved mutants were therefore subjected to stability maturation. All stability improved mutants retained their affinity gains and soluble expression levels were greatly increased. Yeast cells displaying the stabilized, highest affinity mutant retained approximately 80% binding after incubation at 37° C. for 9 days. In addition, this mutant had comparable thermal stability to the wild-type hMFE scFv after restabilization. We have termed the most preferred mutant scFv produced herein sm3E.

By affinity maturing an antibody with a half-life equal to the turnover half-life of the antigen, we have engineered an antibody with effectively. Irreversible binding to CEA. Because CEA is a stable target with a long half-life, differences in tumor retention for the series of scFvs will be dominated by the off-rate of the antibody and not the half-life of CEA. We have therefore succeeded in producing new antibodies with the highly desirable anti-CEA specificity of MFE-23, lacking immunogenicity in humans and having high affinity, high stability and good expressibility. Our mathematical modelling studies show that, contrary to established thinking in the field, these antibodies will have enhanced therapeutic properties, which prediction can be confirmed via the series of scFvs we have generated. Such approaches will also be applicable to tumor surface antigens in general.

Accordingly, the invention provides an antibody specific to carcinoembryonic antigen (CEA) with a dissociation constant of less than 5.0 nM for said antigen and comprising the following six CDRs, as shown in SEQ ID NO: 6 (with the exception of CDR (d)(ii)).

(a) Heavy Chain CDR 1: gly phe asn ile lys asp ser,
(b) Heavy Chain CDR 2: asp pro glu asn gly asp;
(c) Heavy Chain CDR 3: thr pro thr gly pro tyr tyr phe asp,
(d) Light Chain CDR 1: (i) ser ser ser val pro, or
   (ii) ser ser ser val ser;
(e) Light Chain CDR 2: leu thr ser;
(f) Light Chain CDR 3: arg ser ser tyr pro leu.

The invention also provides an antibody to a tumor surface antigen, said antibody binding to said antigen with a dissociation half time of one day or more at 37° C.

The invention also provides a composition comprising an antibody of the invention.

The invention also provides a pharmaceutical composition comprising an antibody of the invention and a pharmaceutically acceptable carrier.

The invention also provides an antibody of the invention for use in a method of treatment of the human or animal body, or in a method of diagnosis practised on the human or animal body.

The invention also provides the use of an antibody of the invention in the manufacture of a medicament for the treatment of a tumor, or in the diagnosis of a tumor.

The invention also provides a method of treating a patient suffering from a tumor, said method comprising administering an antibody of any one of the invention to said patient.

The invention also provides a method of detecting a tumor comprising administering to a patient suspected of suffering from said tumor an antibody of the invention and detecting said label.

The invention also provides a nucleic acid sequence encoding an antibody of the invention.

The invention also provides a vector comprising such a nucleic acid sequence operably linked to sequences capable of securing expression of said antibody in a host cell.

The invention also provides a host cell comprising said vector.

The invention also provides a method of producing an antibody of the invention, said method comprising
(a) expressing said antibody in a host cell, and
(b) recovering said antibody, and optionally purifying said antibody, and optionally
(c) purifying said antibody, and/or
(d) attaching to said antibody an anti-tumor agent and/or a detectable label

($K_D$=8.3±0.5 nM) (●), MFE-23 produced at 20° C. ($K_D$=8.3±1.3 nM) (■), hMFE produced at 37° C. ($K_D$=8.5±0.6 nM) (▲), MFE-23 produced at 37° C. ($K_D$=7.5±0.8 nM) (◆). C) Soluble production of MFE-23 (1) and hMFE (2) at 37° C. for 48 hours. Additional lanes are the scFvs produced at 37° C. and 20° C. for varying amounts of time.

Figure 14:
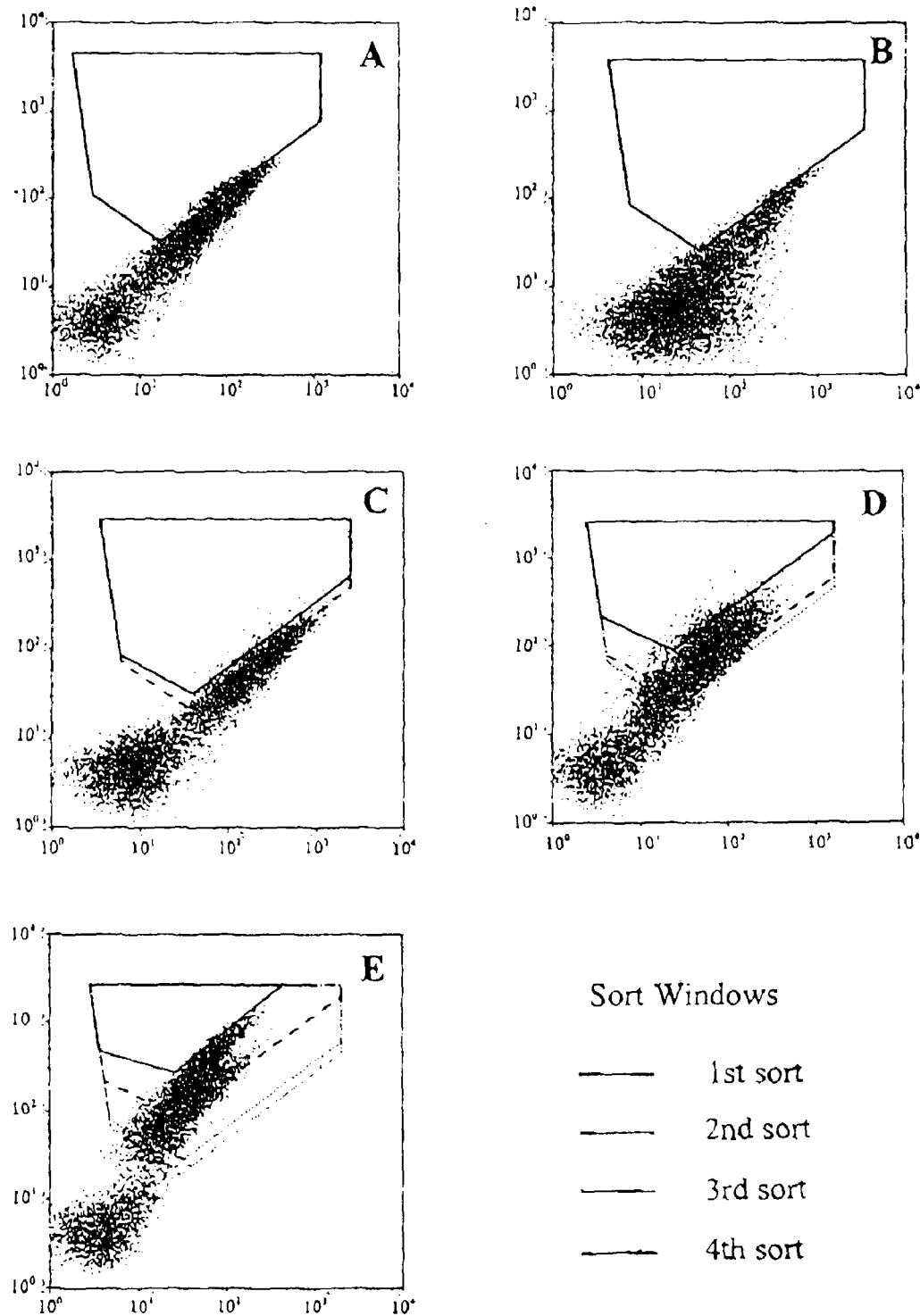

FIG. 14: Sort Data Sort progression for hMFE library labeled at 0.2 nM biotinylated-CEA. CEA binding is on the Y-axis, number of fusions on the surface is on the X-axis.

Figure 15:
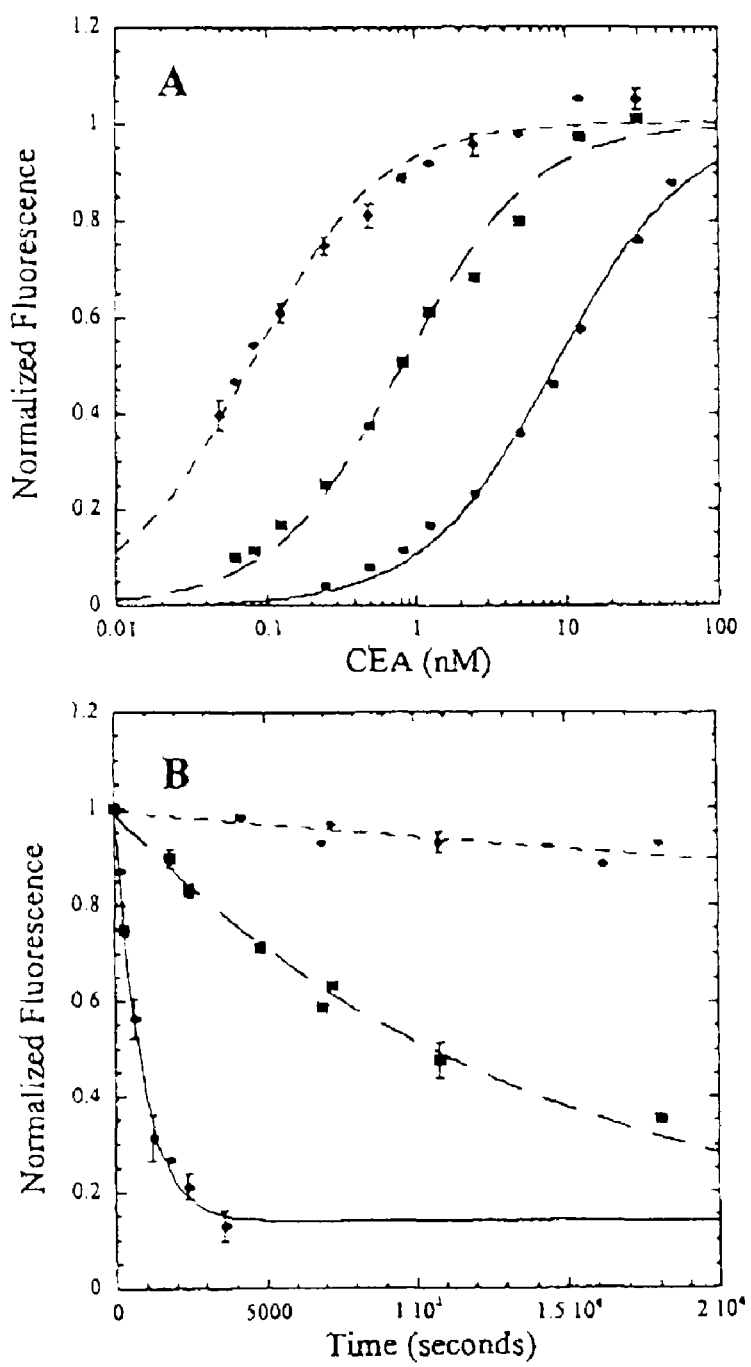

FIG. 15: Titration and Off-Rate for Equilibrium Sort Binding analysis of clones isolated from aggressive hMFE Library sort. A) Equilibrium Titration (Example 3). hMFE ($k_D$=8.5±0.5 nM) (●), m9B ($k_D$=0.8±0.1 nM) (■), m10B ($k_D$=0.08±0.01 nM) (◆)B). Off-rate. Dissociation rates were measured by first labeling yeast displaying the scFv of interest with biotinylated CEA. Then, the labeled cells were washed and incubated with an excess of nonbiotinylated CEA. Dissociation of labeled CEA from the cells was followed at the single cell level by flow cytometry and streptavidin-PE labeling, as described in Example 3. hMFE ($k_{off}$=1.2±0.1×10$^{-3}$ s$^{-1}$) (●), m9B ($k_{off}$=7.5±0.4×10$^{-5}$ s$^{-1}$) (■), m10B ($k_{off}$=6.0±0.4×10$^{-6}$ s$^{-1}$) (◆).

Figure 16:
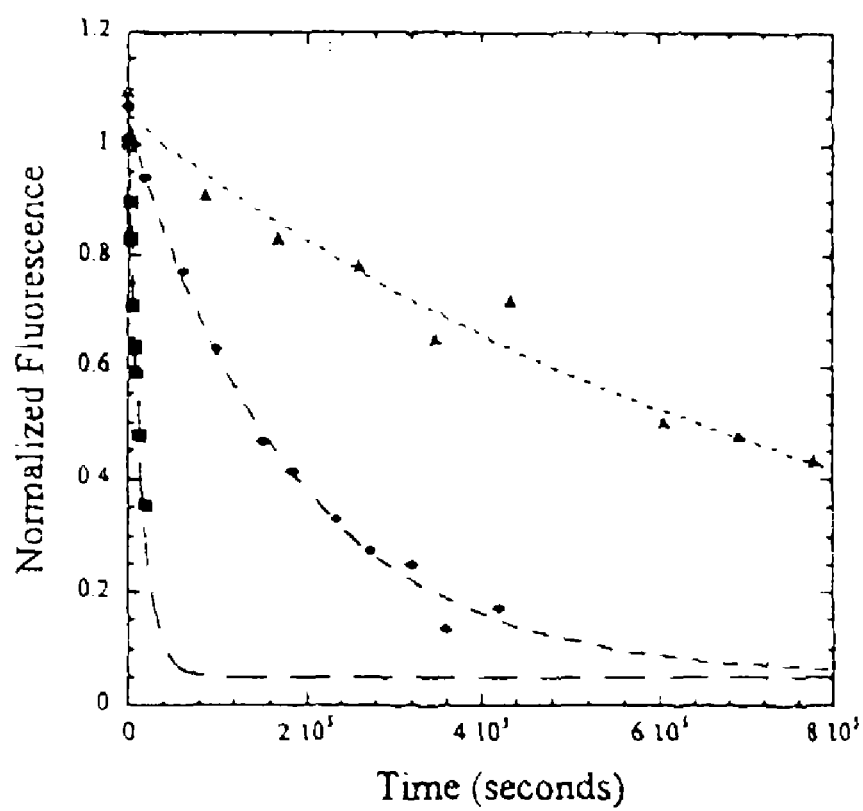

FIG. 16: Off-Rate of Series of Mutants

Off-rate analysis of clones isolated from hMFE library and hLib2 library sorts. m9B (■), m10B (◆), m3E (koff=1.2+0.4×10−6 s−1) (●).

Figure 17:
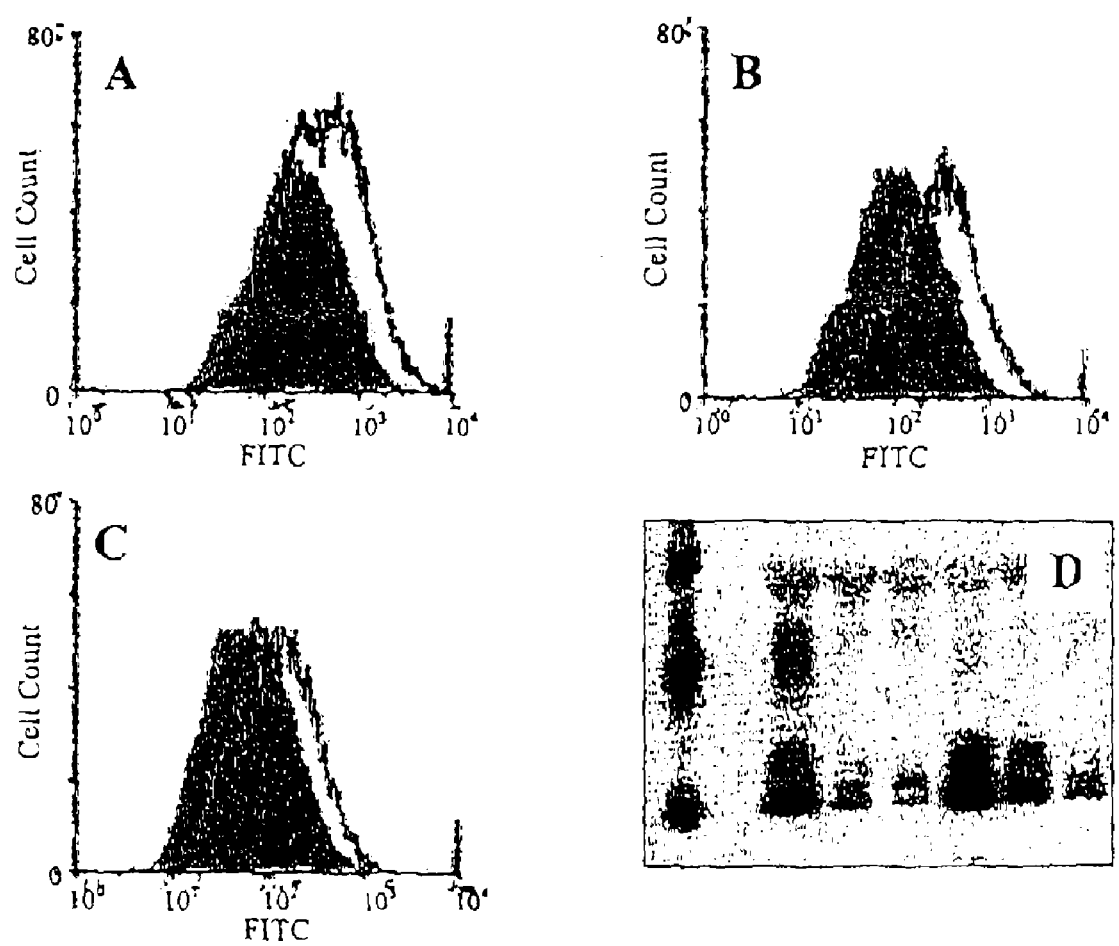

FIG. 17: Effect of $V_L$W47L mutation Display levels were compared between each scFv and the scFv+$V_L$W47L. The solid gray histogram represents the scFv without W47L, the overlay is the scFv containing W47L. A) hMFE. B) m10B. C) m3E. D) Soluble production of mutants. From left to right, samples are: molecular weight ladder, empty lane, hMFE, m10B, m3E, hMFE47L, m10B47L, m3E47L.

Figure 18:
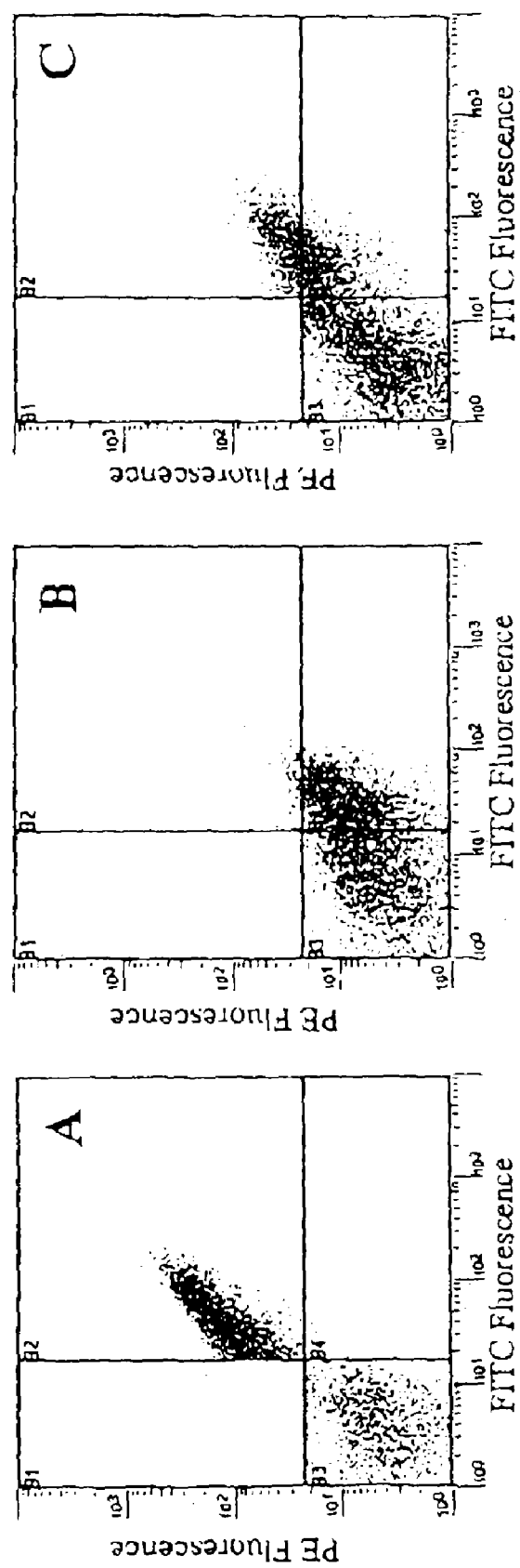

FIG. 18: Destabilization of m3E and m3E47L The two cysteines were removed from the light chain of m3E and m3E47 The number of scFvs on the surface is on the X-axis, CEA binding is on the Y-axis. All samples were labeled at 10 nM CEA. A) m3E. B) m3E-cysout. C) m3E-cys47L.

Figure 19:
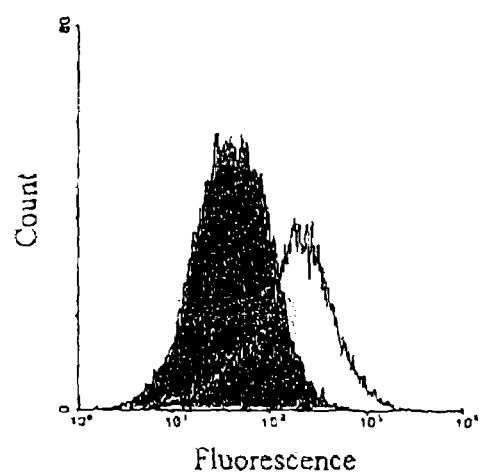
Figure 19:
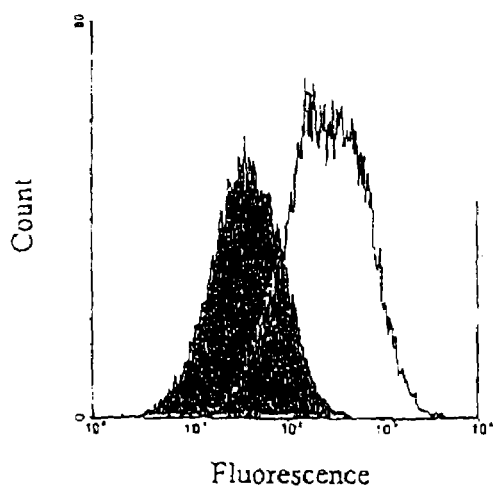
Figure 19:
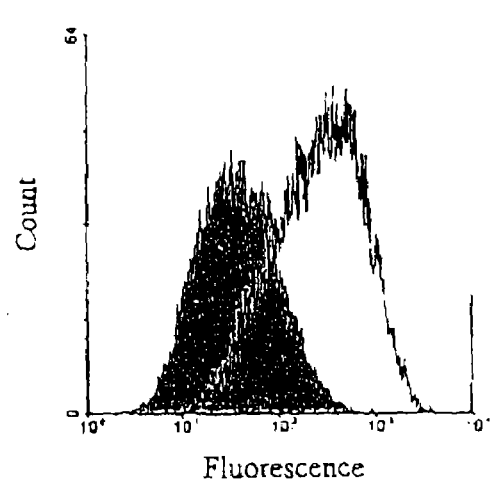

FIG. 19: Display Levels of Well-Expressed Mutants Display levels were compared between each scFv and the scFv plus additional mutations. The solid gray histogram represents the scFv, and the overlay is the scFv containing the mutations. A) m9B. B) m10B. C) m3E.

Figure 20:
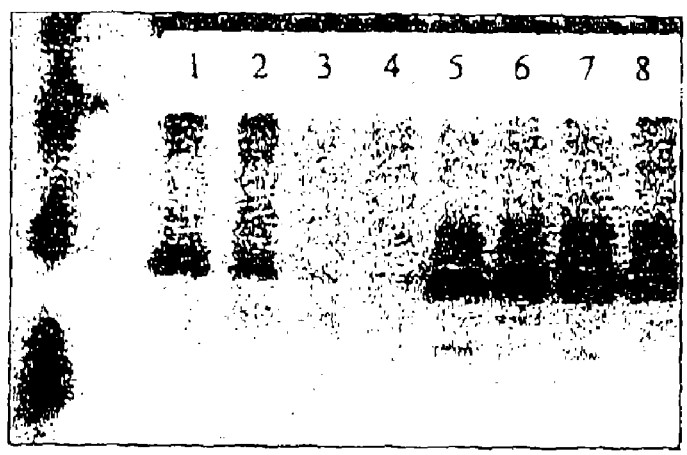
Figure 20:
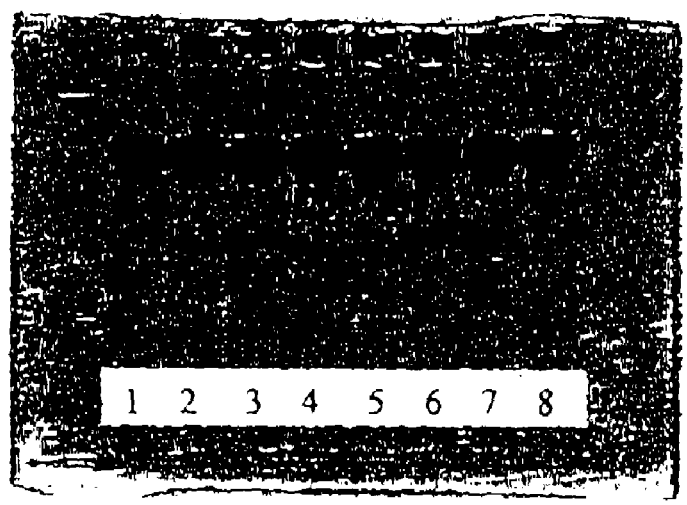

FIG. 20: Soluble Production Soluble production of mutants. A) His$_6$ western. B) Coomassie gel. Samples are hMFE (1), m9B (2), m10B (3), m3E (4), shMFE (5), sm9B (6), sm10B (7), sm3E (8). Description of mutations is in the text FIG. 21: Affinity of Stabilized Mutants A) The affinity of the stabilized mutants was verified by off-rate analysis. The measured off-rates were as follows: sm9B ($k_{off}$=1.1±0.09× 10$^{-4}$ s$^{-1}$) (■), sm10B ($k_{off}$=8.3±0.2×10$^{-6}$ s$^{-1}$) (◆), sm3E ($k_{off}$=1.2±0.08×10$^{-6}$ s$^{-1}$) (▲). B) Equilibrium titration of sm3E ($K_D$=30±3 pM).

Figure 22:
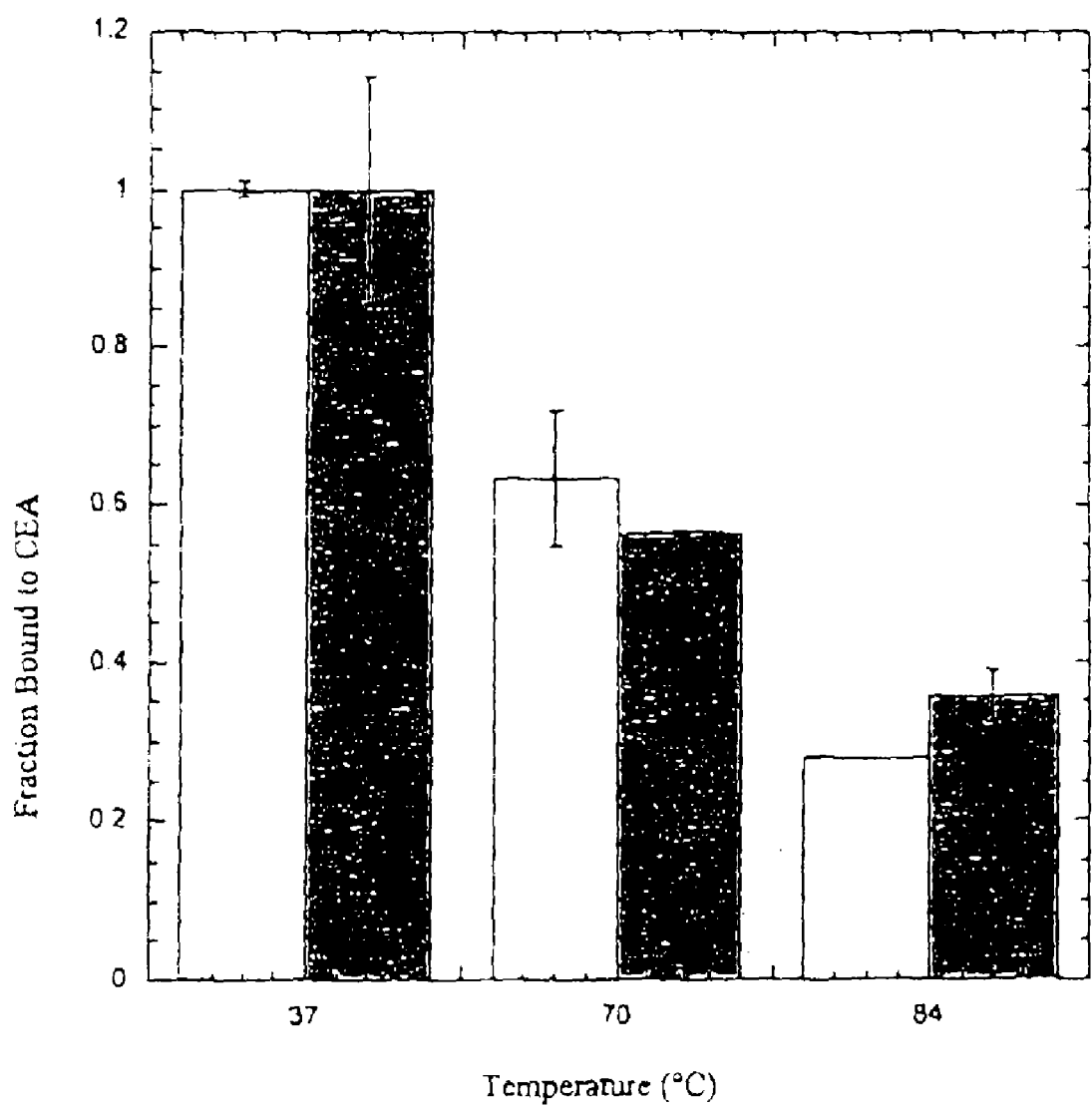

FIG. 22: Stability of hMFE and sm3E scFvs The stability of soluble sm3E was compared to the hMFE scFv at elevated temperatures. Samples were incubated for 1 hour at the designated temperature and then labeled with biotinylated-CEA at 37° C. (See above). Fluorescence readings from incubation at all temperatures were normalized to the reading at 37° C. hMFE (open bars), sm3E (diagonal stripes)

Figure 23:
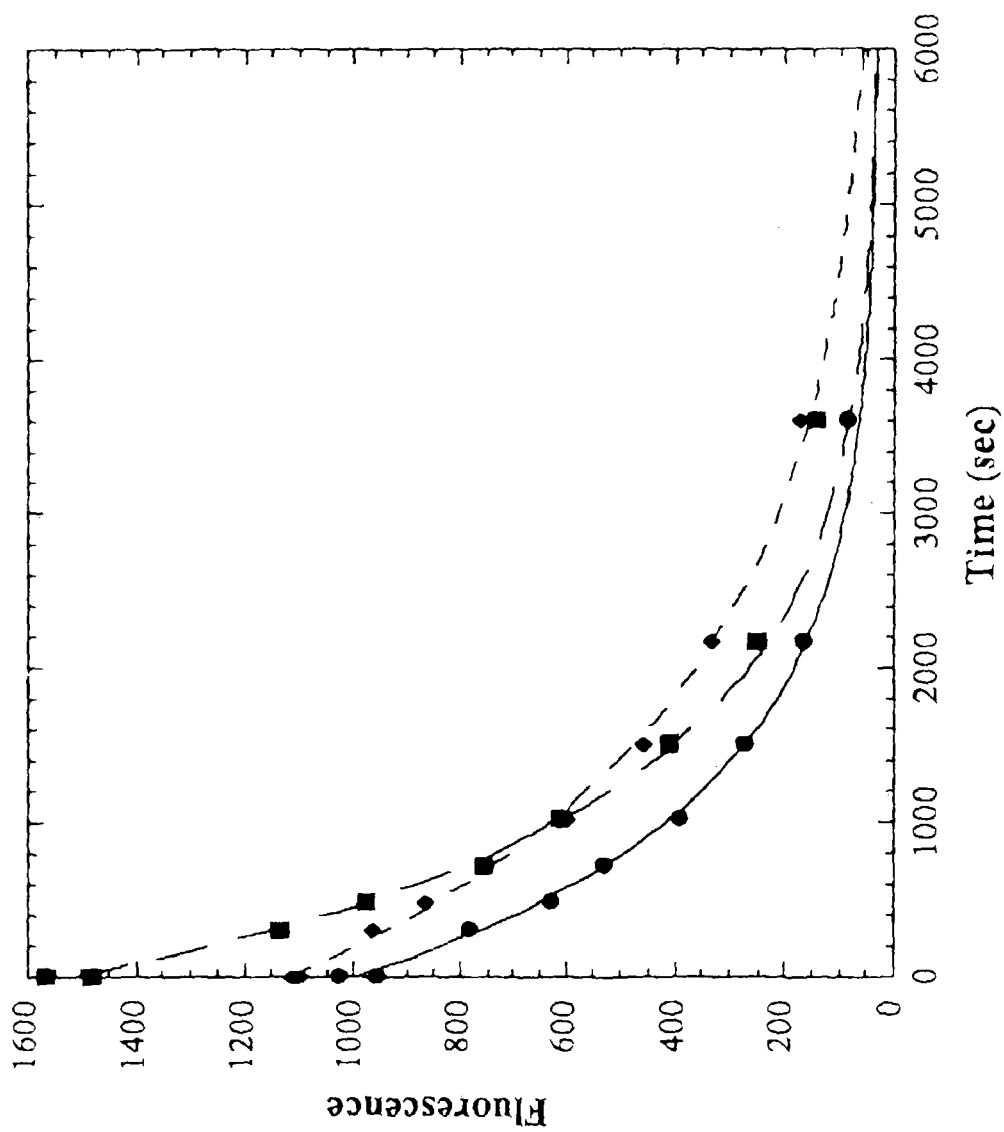
Figure 24:
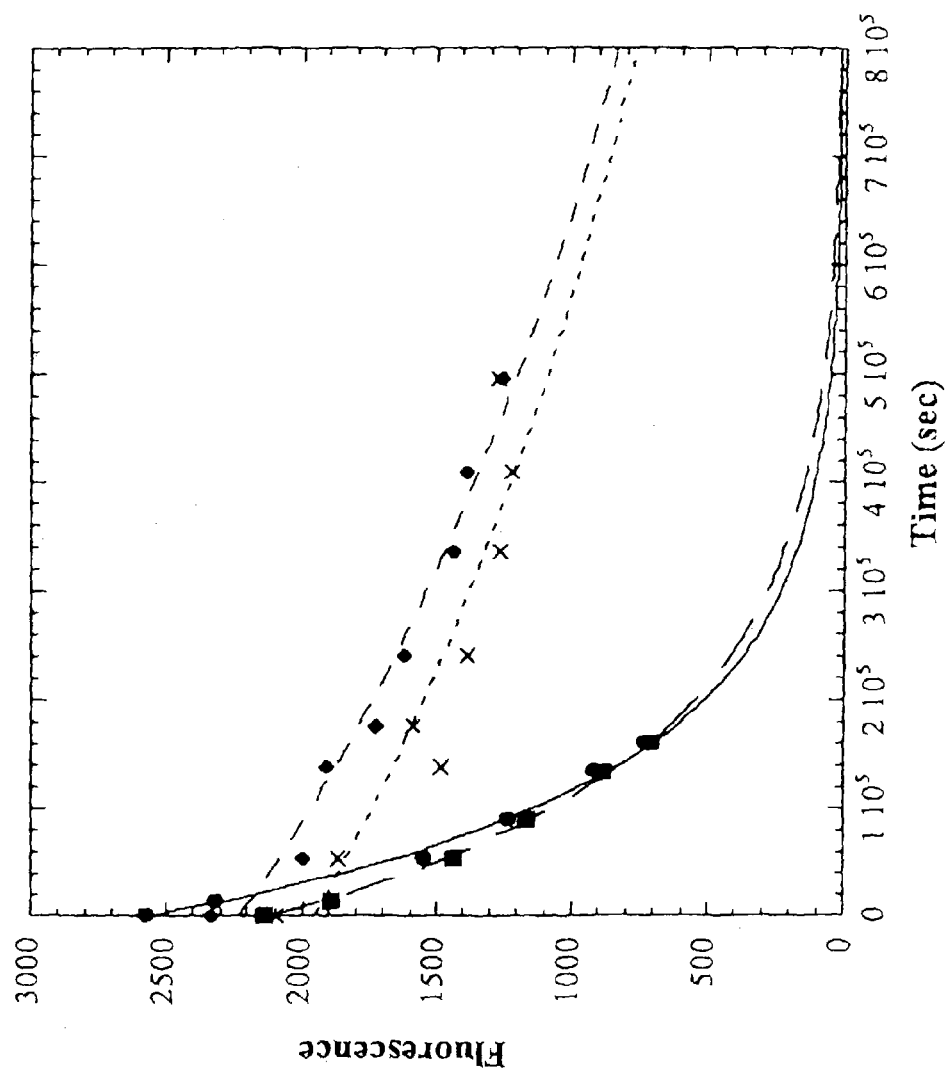

FIGS. 23 and 24: Construction of T98A Mutants To check the contribution of the T98A mutation, this mutation was added to the hMFE, sm10B and sm3E scFcs off-rate analysis was performed with and without T98A. In FIG. 23, the graph plotted circles represents MFE-23, squares=MFE-23, diamonds=hMFE+T98A. In FIG. 24, cirlces=sm10B; squares=sm10B+T98A, diamonds=sm3E; crosses=sm3E+T98A.

BRIEF DESCRIPTION OF THE SEQUENCES

SEQ ID NO: 1/2—Nucleotide and amino acid sequence of MFE-23 This is based on the amino acid sequence of SEQ ID NOS: 1/2 of WO95/15341 but begins from gln 27 of that sequence, which corresponds to position +1 (start heavy chain) of SEQ ID NOS: 3/4 and 5/6 herein. CDRs are shown in bold. Note that the position and length of the CDRs shown below correspond to the position and length of the CDRs shown in SEQ ID NOS: 3/4 and 5/6 herein. Slightly different positions and lengths are in some cases given in WO95/15341.

SEQ ID NO 3/4—Nucleotide (SEQ ID NO: 3) and amino acid (SEQ ID NO: 4) sequence of hMFE-23.

SEQ ID NO: 5/6—Nucleotide (SEQ ID NO: 5) and amino acid sequence (SEQ ID NO: 6) of sm3E.

SEQ ID NOS: 7/8—Primers used in the cloning of MFE-23.

SEQ ID NOS: 9/10—Oligonucleotides for HIS tag in secretion vector.

SEQ ID NOS: 11/12—Nested primers for shuffled amplification in construction and screening of hMFE library.

SEQ ID NOS: 13/14—Primers for W47L change.

SEQ ID NOS; 15–18—Primers for site-directed mutagenesis.

SEQ ID NOS: 19–22—Primers for high stability mutant.

SEQ ID NOS: 23–24 —Primers for T98A mutants.

DETAILED DESCRIPTION OF THE INVENTION

Antibodies of the Invention

An antibody of the invention is specific to a tumor surface antigen. Preferably, said antigen is carcinoembryonic antigen (CEA).

An antibody of the invention may be of any type as long as it has the ability to bind to the tumor surface antigen. For example, it may be a complete IgG molecule. It may comprise two heavy and two light chains as in nature. Alternatively, it may be an antibody fragment such as a Fab or F(ab')$_2$ fragment or an Fv or single-chain Fv antibody (scFv).

Preferably, the antibody of the invention will be an scFv ScFvs are advantageous from the point of view of delivery to tumours.

An antibody of the invention may be fully or partly humanised in order to minimise its immunogenicity in humans.

An antibody of the invention will typically have a dissociation constant ($K_D$) for its antigen of 10.0 nM or less, or 5.0 nM or less, more preferably 2.0 nM or less, 1.0 nM or less, 0.5 nM or less, 0.2 nM or less, 0.1 nM or less, 0.05 nM or less or 0.01 nM or less.

An antibody of the invention will typically have an off-rate of less than 10×10$^{-6}$ s$^{-1}$, more preferably less than 5×10$^{-6}$ s$^{-1}$, less than 2×10$^{-6}$ s$^{-1}$, or less than 1.5×10$^{-6}$ s$^{-1}$.

An antibody of the invention will desirably have an off-rate equal to or lower than the degradation rate of the antigen to which it binds. Put another way, an antibody of the invention will desirably have a half-life equal to or longer than the turnover half-life of the antigen. This ensures effectively irreversible binding of the antibody to the antigen. Thus, tumor retention of the antibody will be dominated by the off-rate of the antibody and not the half-life of the antigen.

An antibody of the invention will typically bind to its antigen with a dissociation half time of 6 hours or more, 12 hours or more, 1 day or more, 3 days or more, 2 days or more or 5 days or more.

Antibodies of the invention may include non-antibody sequences as long as the properties of the invention are retained. For example, epitope tags may be included. Two tags that may be included are HA tags and c-myc tags.

Antibodies to CEA

Anti-CEA antibodies of the invention will typically be derived from the MFE-23 scFv of Chester et al. (supra).

Typically, such an antibody will comprise the following six CDRs, as shown in SEQ ID NO: 6 (with the exception of CDR (d)(ii)):
 (a) Heavy Chain CDR 1: gly phe asn ile lys asp ser.
 (b) Heavy Chain CDR 2: asp pro glu asn gly asp,
 (c) Heavy Chain CDR 3: thr pro thr gly pro tyr tyr phe asp;
 (d) Light Chain CDR 1: (i) ser ser ser val pro, or
  (ii) ser ser ser val ser.
 (e) Light Chain CDR 2: leu thr ser.
 (f) Light Chain CDR 3: arg ser ser tyr pro leu Such antibodies may comprise the sequence of the MFE-23 antibody of SEQ ID NO: 2, said sequence having the following substitutions as shown in the sequence of the sm3E antibody of SEQ ID NO: 6:
 (a) SVL50L (Serine to Leucine in light chain CDR 2); and/or
 (b) FVL36L (Phenylalanine to Leucine between light chain CDRs 1 and 2); and optionally
 (c) VLS31P (Serine to Proline in light chain CDR 1); and/or
 (d) VLA13V (Alanine to Valine in the light chain upstream of CDR 1); and/or
 (e) VLW47L (Tryptophan to Leucine between light chain CDRs 1 and 2); and/or
 (f) VLM78V (Methionine to Valine between light chain CDRs 2 and 3).

Optionally, other substitutions, deletions and insertions may be present, substitution of up to 50, up to 30, up to 20 or up to 5 or 10 further amino acids outside the CDRs, and/or deletion or insertion of up to 5, up to 10, up to 20, up to 30 or up to 50 amino acids outside the CDRs, and/or insertion of up to 20 amino acids outside the CDRs (See the following references for examples of insertion and deletion mutations: J. Immunol Methods 2002 Jan 1; 259 (1–2): 43–53; J. Immunol Methods May 1, 2001; 251(1–2): 137–49; Journal of Molecular Biology, Vol. 294, No. 3, Dec. 1999, pp. 701–710; Journal of Molecular Biology, Vol. 291, No. 3, August 1999, pp 589–602).

Substitution (a) above is important to ensuring high affinity of MFE-23-derived antibodies to CEA. Substitution (b) also has a significant effect even though it is not in a CDR.

Preferably, an antibody of this type has both substitutions (a) and (b). More preferably it will also have at least two of three of substitutions (c)–(f), desirably all of them.

Of the further changes that may be made to MFE-23, changes that "humanize" the antibody are preferred: compare the sequence of MFE-23 (SEQ ID NO: 2) with that of humanised hMFE (SEQ ID NO: 4). Preferred changes thus include those set out in the following table. Desirably, 5 or more, 10 or more, 15 or more, 20 or more or 25 or more of these changes, or all of them, will be made.

| SEQ ID NO 2 | Position | SEQ ID NO 4 |
|---|---|---|
| gln | 5 | glu |
| leu | 11 | val |
| arg | 13 | lys |
| ser | 14 | pro |
| thr | 16 | ala |
| thr | 23 | lys |
| glu | 42 | gly |
| gly | 44 | arg |
| ser | 76 | ala |
| gln | 82 | gly |
| thr | 87 | arg |
| ser | 88 | pro |
| thr | 115 | leu |
| ala | 144 | ser |
| ile | 145 | ser |
| pro | 150 | val |
| glu | 152 | asp |
| lys | 153 | arg |
| thr | 157 | ala |
| thr | 176 | lys |
| ala | 194 | ser |
| ser | 204 | asp |
| arg | 211 | ser |
| glu | 213 | gln |
| ala | 214 | pro |
| ala | 234 | gly |
| leu | 240 | ile |

Particularly preferred antibodies of this aspect of the invention comprise the sequence of SEQ ID NO: 6 from position +1 (start light chain) to the beginning of the c-myc tag or the sequence of SEQ ID NO: 6 from position +1 (state heavy chain) to the beginning of the c-myc tag. An especially preferred antibody is sm33E, having the sequence of SEQ ID NO 6.

Desirably, MFE-23-derived antibodies of the invention will have an off-rate 10 or more times, 100 or more times, 500 or more times or 1000 or more times lower than that of MFE-23 itself.

Recombinant Production of Antibodies of the Invention

The invention provides nucleic acids encoding the antibodies of the invention. Such coding sequences may be DNA or RNA, preferably DNA. The coding sequences may have any codon usage but will preferably be codon-optimised for expression in yeast.

Coding sequences of the invention may be comprised in a vector, desirably an expression vector. Suitable vectors include plasmids and viruses. In an expression vector, the coding sequence will be operably linked to regulatory sequences that secure its expression in a host cell. Such sequences include promoters, enhancers and terminators. Desirably, the regulatory sequences will be capable of securing the expression of the antibody-encoding sequence in a yeast cell, e.g. a cell of Saccharomyces cerevisiae.

Host cells of the invention may be produced by introducing the vectors of the invention into cells by any means known in the art, e.g. by transformation or transfection. Yeast host cells are preferred.

Antibodies of the invention may be produced in any suitable manner. Typically they will be produced by expressing said antibody in a host cell of the invention and recovering said antibody from said cell, and optionally purifying said antibody. Purification may be carried out by any means known in the art, e.g. by affinity chromatography. His tags may be used for purification purposes.

Treatments and Diagnoses of the Invention

Whilst the antibodies of the invention may find utility as antibodies per se, they will desirably be attached to a detectable labels and/or an antitumor agent. In this regard, anti-CEA antibodies of the invention may be used in a similar manner to MFE-23, discussed herein (cf Chester et al., 1994, WO95/15431, U.S. Pat. No. 5,876,691 to Chester et al) which has been used to effectively target colon cancer for radioimmunodetection in vivo (Begent et al., 1996) and in radioimmunoguided surgery of colorectal cancer (Mayer et al., 2000).

Attachment to a detectable label will target the label to tumor cells and thus enable detection of tutors expressing the tumor surface antigen to which the antibody binds, and hence diagnosis of such tumors. Detectable labels may be short-lived radioisotopes such as $^{111}$In, $^{123}$I or $^{99m}$Tc. Other labels, such as fluorescent labels may also be used in appropriate circumstances.

Attachment to an antitumor agent will target the antitumor agent to the tumor and thus effect treatment of the tumor. Antitumor agents include toxic agents such as chemotherapeutic agents and radioisotopes, enzymes which activate prodrugs, and cytokines. Suitable chemotherapeutic agents include anthracyclines. Preferred cytokines include TNF-alpha. Preferred enzymes for prodrug activation include carboxypeptidase G2 (CPG2).

Antitumor agents and detectable labels may be attached to antibodies of the invention by means known in the art. Where the label or agent is a polypeptide, it may be expressed as a fusion protein with the antibody.

Antibodies of the invention may be administered in any suitable manner known in the art. They will normally be administered in conjunction with a pharmaceutically acceptable carrier. In clinical use, they will typically be administered parenterally, e.g. intravenously or intraperitoneally and the composition will thus be formulated for such routes of delivery.

A person of skill in the art will be able to determine a suitable dosage and dosage regimen based on his/her experience and assessment of the patient's condition. Suitable doses of antibodies are also known in the art, e.g. as discussed above in relation to MFE-23. As a guide, doses of 0.01 to 100 mg, e.g. 0.1 to 10 mg may be used.

Where the antigen is CEA, treatment or diagnosis of any tumor whose cells express CEA may be effected. Treatment and diagnosis of breast tumors is preferred. Treatment and diagnosis of colorectal tumors is another possibility.

EXAMPLES

Example 1

Mathematical Modelling of Antibody Penetration and Binding in Tumor Microspheroids Experimental Methods Description of Model A model was constructed to describe antibody penetration in tumor microspheroids as it relates to diffusion, antibody/antigen binding, and antibody/antigen degradation. The model is based on the equations derived by Weinstein and coworkers (van Osdol et al., 1991) with minor modification. Specifically, convection is not included in the model because flow is negligible within nonvascularized micrometasases. The basic model equations are as follows:

$$\frac{\partial Ab}{\partial t} = D \frac{1}{r^2} \frac{\partial}{\partial r}\left(r^2 \frac{\partial Ab}{\partial r}\right) - \frac{k_{on}}{\varepsilon} AbAg + k_{off} B \quad \text{Equation 1}$$

$$\frac{\partial Ag}{\partial t} = R_s - \frac{k_{on}}{\varepsilon} AbAg + k_{off} C - k_e Ag \quad \text{Equation 2}$$

$$\frac{\partial B}{\partial t} = \frac{k_{on}}{\varepsilon} AbAg - k_{off} B - k_e B \quad \text{Equation 3}$$

The boundary conditions are specified by plasma pharmacokinetics and spherical symmetry. They are: zero antibody gradient at the center and specified surface antibody concentration.

$$\frac{\partial Ab}{\partial r}(0) = 0$$

$$Ab(R) = \varepsilon Ab_p(t)$$

With the following material balance:

$$Ag_t = Ag + B$$

At time zero, the antibody concentration is equal to zero everywhere in the spheroid (Ab=B=0) and available antigen is equal to the total antigen present (Ag=Ag$_t$).

The variables are defined as follows:
Dependent Variable:
Ab=concentration of unbound antibody, [mol/(tumor volume in L)]
Ag=concentration of unbound antigen, [mol/(tumor volume in L)]
B=concentration of antibody/antigen complex, [mol/(tumor volume in L]
Independent Variable:
r=distance from the center of the spheroid, [µm]
t=time, [seconds]
The following is a list of parameters:
D=antibody diffusivity in tumor, [µm$^2$/s]
$\varepsilon$=volume fraction of tumor accessible to antibody
$k_{on}$=association rate constant, [M$^{-1}$s$^{-1}$]
$k_{off}$=dissociation rate constant, [s$^{-1}$]
$k_e$=rate constant for degradation of antigen and antibody/antigen by endogenous metabolism, [s$^{-1}$]
$R_s$=rate of synthesis of new antigen, set equal to $k_e Ag_f$ The plasma concentration of the antibody at the microspheroid surface is determined from empirical two-exponential kinetics as follows $$Ab_p(t) = Ab_n\{\alpha 2^{-\tau 1/\tau_\alpha} + \beta 2^{-\tau/\tau_\beta}\}$$

Ab$_0$=initial antibody concentration in plasma at time zero, [mol/L]
$\alpha,\beta$=fractions of $\alpha$ and $\beta$ elimination phases, respectively
$\tau_\alpha,\tau_\beta$=half-life of $\alpha$ and $\beta$ elimination phases, respectively A list of the parameter values for the model, as well as the literature references for the selected values, is contained in Table 1. For certain parameters, a range of values was tested in order to determine the optimal conditions.

TABLE 1

Parameter values for model simulations

| Parameter | Value | Source | Notes |
|---|---|---|---|
| R | 0–300 μm | Groebe and Mueller-Klieser, 1996 | |
| D | 14–80 μm²/s | Berk, DA et al., 1997 | Scaled to 37° C. by Stokes Einstein |
| $\epsilon$ | 0.1–0.28 | Krol, A et al., 1999 | Varies with antibody size |
| $k_{on}$ | $10^4$–$10^6$ $M^{-1}s^{-1}$ | | Adjustable parameter |
| $k_{off}$ | $10^{-3}$–$10^{-6}$ $s^{-1}$ | | Adjustable parameter |
| $k_e$ | $10^{-3}$–$10^{-6}$ $s^{-1}$ | Baulida, J et al., 1996; Worthylake, R et al., 1999; Bidart, JM et al., 1999; Stein, R et al., 1999; Press, OW et al., 1994; Kyriakos, RJ et al., 1992 | Antigen dependent |
| $Ag_t$ | 10–1000 nM | Baxter and Jain, 1991; Press, OW et al., 1994; Worthylake, R et al., 1999 | Antigen dependent |
| Ab | 10–1000 nM | | Adjustable parameter |
| $\tau_\alpha$ | 0.1–0.9 hr (scFv)<br>3–5 hr (IgG) | Begent, RH et al., 1996; Milenic, DE et al., 1991; Green, AJ et al., 2001 | |
| $\tau_\beta$ | 3–5 hr (scFv)<br>26–72 hr (IgG) | | |

The numerical solution was obtained with the Absoft Fortran 77 software package using the method of lines (IMSL MOLCH).

Shrinking Core Model

In order to test the numerical solution for accuracy, the simulations were tested against an analytical model. The Shrinking Core Model (SCM), an analytical method used to describe reaction kinetics in heterogeneous catalytic particles with a shrinking unreacted core, provides a situation which is analogous to antibody penetration within a microspheroid. The central assumption of the shrinking core model is that diffusion from the surface of the sphere to the internal reaction front is a slow process, and consumption of the surface reactant is extremely rapid at the reaction front at a critical radius $r_c$. The antibody spheroid penetration model can be analyzed in a similar fashion by solving the following sets of equations:

$$\frac{d^2 Ab}{dr^2} + \frac{2}{r}\frac{dAb}{dr} = 0 \text{(Assume quasi-steady state diffusion)} \quad \text{Equation 4}$$

@ $r = R$, $Ab = Ab_0$

@ $r = r_c$, $Ab = 0$

The relationship between the rate of disappearance of the antigen and the flux of the antibody to the core of the tumor by diffusion is given by equation 5:

$$\frac{\partial}{\partial t}\left(\frac{4}{3}\pi r_c^3 Ag_0\right) = 4\pi r_c^2 D \frac{dAb}{dr} \quad \text{Equation 5}$$

Integration of equation 5 at the critical radius $r_c$ and use of the solution from equation 4 yields the following equation which describes the movement of the reaction front at $r_c$:

$$t = t_{sat}\left(1 - 3\left(\frac{r_c}{R}\right)^2 + 2\left(\frac{r_c}{R}\right)^3\right) \quad \text{Equation 6}$$

$$t_{tot} = \frac{R^2(Ag_1/\varepsilon)}{6D(Ab_o)}$$

Figure 1:
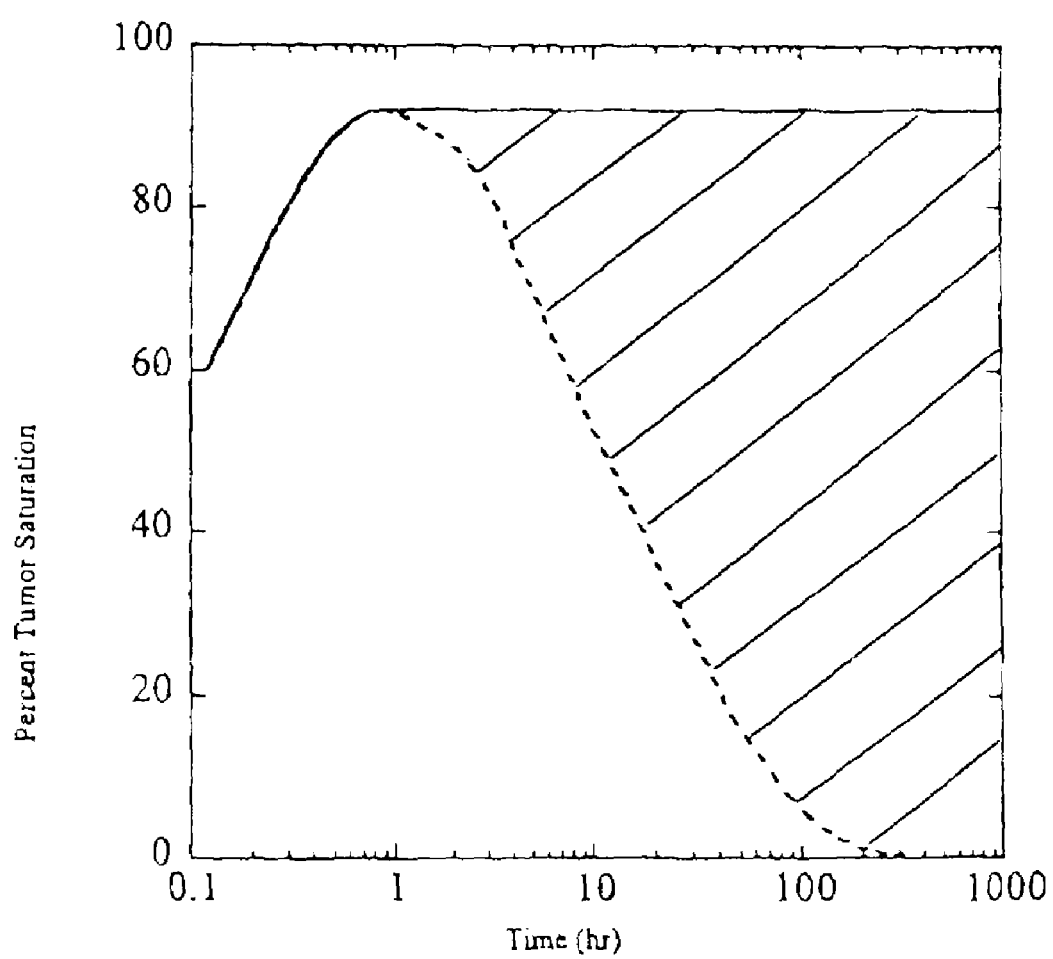
FIG. 1: Antibody Retention Qualitative analysis of percent tumor saturation as a function of time for steady intravenous infusion (solid line) and single bolus administration (dashed line). The cumulative effect of the antibody in the tumor over time can be measure by the area under the curve (AUC). The difference in the AUC between the two methods of administration is represented by the hatched area

Equation 6 can then be used to predict the location of the bound antibody front $r_c$ as a function of time when surface antibody concentration is held constant. From a therapeutic perspective, constant antibody concentration can only be accomplished through steady intravenous infusion. However, single bolus dosing is more generally practiced with antibodies. This necessitates consideration of the effect of antibody pharmacokinetics in the plasma. To adapt the shrinking core model to single bolus dosing, a new term will be introduced. For biodistribution studies, a measurement used to estimate the cumulative effect of the antibody in the tumor over time is the area under the curve (AUC). For constant antibody concentration, the product $Ab_0\tau_{sat}$ is equal to the time integral of the surface antibody concentration, the AUC (FIG. 1). In cases where surface antibody concentration is not constant (ie. single bolus infusion), the concentration of the antibody over time decrease in a fashion relative to its rate of removal from the blood stream (i.e. the plasma pharmacokinetics) (FIG. 1). For single exponential antibody pharmacokinetics in plasma, the corresponding AUC is given instead by $Ab_0\tau_\alpha/\ln 2$, where $\tau_\alpha$ is the plasma half-life for the antibody.

Validation of Model with Published Experimental Data

In addition to testing the numerical solution analytically, it was necessary to also verify its accuracy by comparing simulation results against published experimental data. To do this, several papers were selected from the literature. The papers chosen targeted several different antigens (ErbB2, EGFRvIII, and CEA) and encompassed more than one antibody molecule, differing in size and valency (scFv and scFv-fusion protein). The papers used for comparison are summarized in table 2. The parameter values extracted from each paper and used in the simulations are summarized in tables 3–6.

TABLE 2

Papers

| Paper | Target | Antibody Molecule |
|---|---|---|
| Adams et al., Cancer Res. 61: 4750, 2001 | ErbB2 | scFv (range of affinities; single time point) |
| Kuan et al., Int. J. Cancer 88: 962, 2000 | EGFR | scFv (two affinities; multiple time points) |
| Wu et al., Immuno. 2: 21, 1996 | CEA | scFv (two affinities; multiple time points) |
| Cooke et al., Bioconjugate Chem. 13.7, '02 | CEA | scFv-fusion protein - 144 kDa (single affinity; multiple time points) |

TABLE 3

Parameter Set for Adams et al., Cancer Res. 61: 4750, 2001

| Parameter | Value | Notes |
|---|---|---|
| R | 300 µm | |
| D | 80 µm$^2$/s | scFv |
| $\epsilon$ | 0.28 | scFv |
| $k_{on}$ | 4.1, 4.0, 7.6, 5.0, 6.9 ($10^5$ M$^{-1}$s$^{-1}$) | scFvs: C6G98A, C6.5, C6ML3-9, C6MH3-B1, C6-B1D2 |
| $k_{off}$ | 1310, 63, 7.6, 0.6, 0.1 ($10^{-4}$ s$^{-1}$) | scFvs: C6G98A, C6.5, C6ML3-9, C6MH3-B1, C6-B1D2 |
| $k_e$ | 6.67 × 10$^{-4}$ s$^{-1}$ | Baulida, J et al., 1996; Worthylake, R et al., 1999 |
| $Ag_t$ | 1670 nM | Worthylake, R et al., 1999 |
| Ab | 370 nM | 20 ug per mouse (2 ml blood volume) |
| $\tau_\alpha$ | 0.23 hr (0.9) | Nielsen, UB et al., 2000 |
| $\tau_\beta$ | 5.7 hr (0.1) | Nielsen, UB et al., 2000 |

TABLE 4

Parameter Set for Kuan et al., Int. J. Cancer 88: 962, 2000

| Parameter | Value | Notes |
|---|---|---|
| R | 300 µm | |
| D | 80 µm$^2$/s | scFv |
| $\epsilon$ | 0.28 | scFv |
| $k_{on}$ | 0.91, 7.8 ($10^5$ M$^{-1}$s$^{-1}$) | scFvs: MR1, MR1-1 |
| $k_{off}$ | 2.1, 1.2 ($10^{-3}$ s$^{-1}$) | scFvs: MR1, MR1-1 |
| $k_e$ | 6.67 × 10$^{-4}$ s$^{-1}$ | Baulida, J et al., 1996; Worthylake, R et al., 1999 |
| $Ag_t$ | 1670 nM | Worthylake, R et al., 1999 |
| Ab | 37 nM | 2 ug per mouse (2 ml blood volume) |
| $\tau_\alpha$ | 0.5 hr (0.8) | |
| $\tau_\beta$ | 5 hr (0.2) | |

TABLE 5

Parameter Set for Wu et al., Immuno. 2: 21, 1996

| Parameter | Value | Notes |
|---|---|---|
| R | 300 µm | |
| D | 80 µm$^2$/s | scFv |
| $\epsilon$ | 0.28 | scFv |
| $k_{on}$ | 6.5, 10 ($10^5$ M$^{-1}$s$^{-1}$) | scFvs: T84.66/C28, T84.66/212 |
| $k_{off}$ | 3.0, 2.5 ($10^{-4}$ s$^{-1}$) | scFvs: T84.66/C28, T84.66/212 |
| $k_e$ | 8.0 × 10$^{-6}$ s$^{-1}$ | Stein, R et al., 1999 |
| $Ag_t$ | 840 nM | Baxter and Jain, 1991 |

TABLE 5-continued

Parameter Set for Wu et al., Immuno. 2: 21, 1996

| Parameter | Value | Notes |
|---|---|---|
| Ab | 7.4 nM | 0.3–0.5 ug per mouse (2 ml blood volume) |
| $\tau_\alpha$ | 0.14; 0.12 hr | T84.66/C28; T84.66/212 |
| $\tau_\beta$ | 3.27; 4.8 hr | T84.66/C28; T84.66/212 |

TABLE 6

Parameter Set for Cooke et al., Bioconjugate Chem. 13: 7, '02

| Parameter | Value | Notes |
|---|---|---|
| R | 300 µm | |
| D | 14 µm$^2$/s | (MW = 144 kDa) |
| $\epsilon$ | 0.1 | (MW = 144 kDa) |
| $k_{on}$ | 4 × 10$^5$ M$^{-1}$s$^{-1}$ | MFE-23 scFv |
| $k_{off}$ | 1 × 10$^{-3}$ s$^{-1}$ | MFE-23 scFv |
| $k_e$ | 1.15 × 10$^{-6}$ s$^{-1}$ | Stein, R et al., 1999 |
| $Ag_t$ | 840 nM | Baxter and Jain, 1991 |
| Ab | 21.5 nM | 6.2 ug per mouse (2 ml blood volume) |
| $\tau_\alpha$ | 3 hr | |
| $\tau_\beta$ | 50 hr | |

Results

Effect of Antibody Affinity on Tumor Penetration

Figure 2:
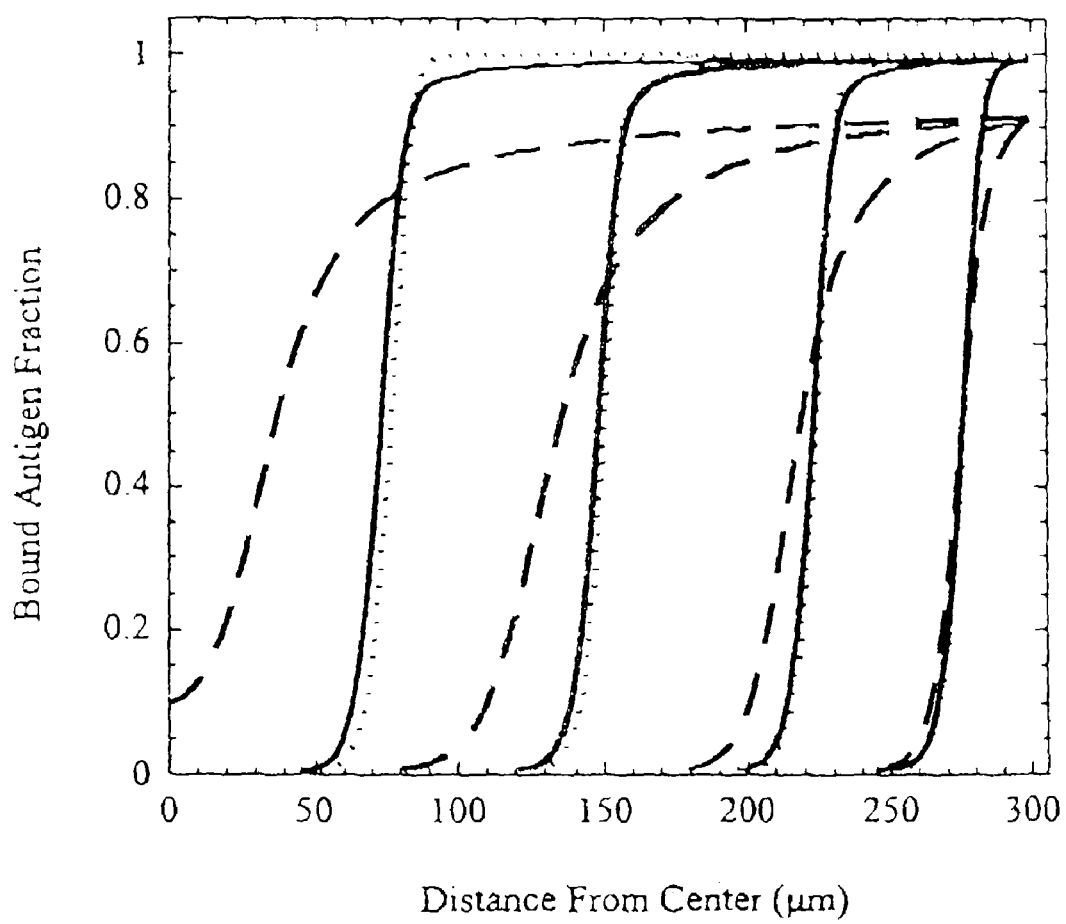
FIG. 2: Movement of Antibody Front The simulation was performed for an IgG with a constant antibody concentration of 100 nM and an antigen concentration of 800 nM. Antibodies with three different affinities were tested: $K_D$=10 nM (dashed line), $K_D$=1 nM (solid line), and $K_D$=0.1 nM (dotted line). Location of the moving front was captured (curve sets from right to left in the Figure) at 0.5 hrs, 3.8 hrs, 10.9 hrs, and 20 hrs

Several investigators have observed the tendency of high affinity antibodies to penetrate less uniformly and remain bound at the outer shell of the tumor. This phenomenon, termed the "binding site barrier" (Weinstein et al., 1987), has been used as an argument against the development and use of high affinity antibodies for tumor therapy. To examine the broad features of antibody penetration into the microspheroid, simulations were performed with constant surface antibody concentration, in the absence of antigen degradation, for a range of antibody affinities (FIG. 2). As previously described, high affinity antibodies fill a "shell" at the rim of the sphere, and this shell moves progressively towards the center of the sphere. Because the antibody concentration is held constant in this simulation, the antibody penetrates the tumor as a moving front until all of the antigen binding sites are saturated. In a more therapeutically realistic situation, antibody concentration at the tumor surface is not held constant, and instead decreases as the antibody is depleted from the circulation. Hence, the "binding site barrier" effect is created by the dynamic interaction of pharmacokinetics with diffusion: if antibody concentration drops to negligible levels before the shell front has moved entirely to the center of the sphere, it will appear that the antibodies became "stuck" at a fixed distance from the surface, although what is actually observed is only a "freeze frame" of a kinetic process that stopped when antibody was cleared from the plasma.

Figure 3:
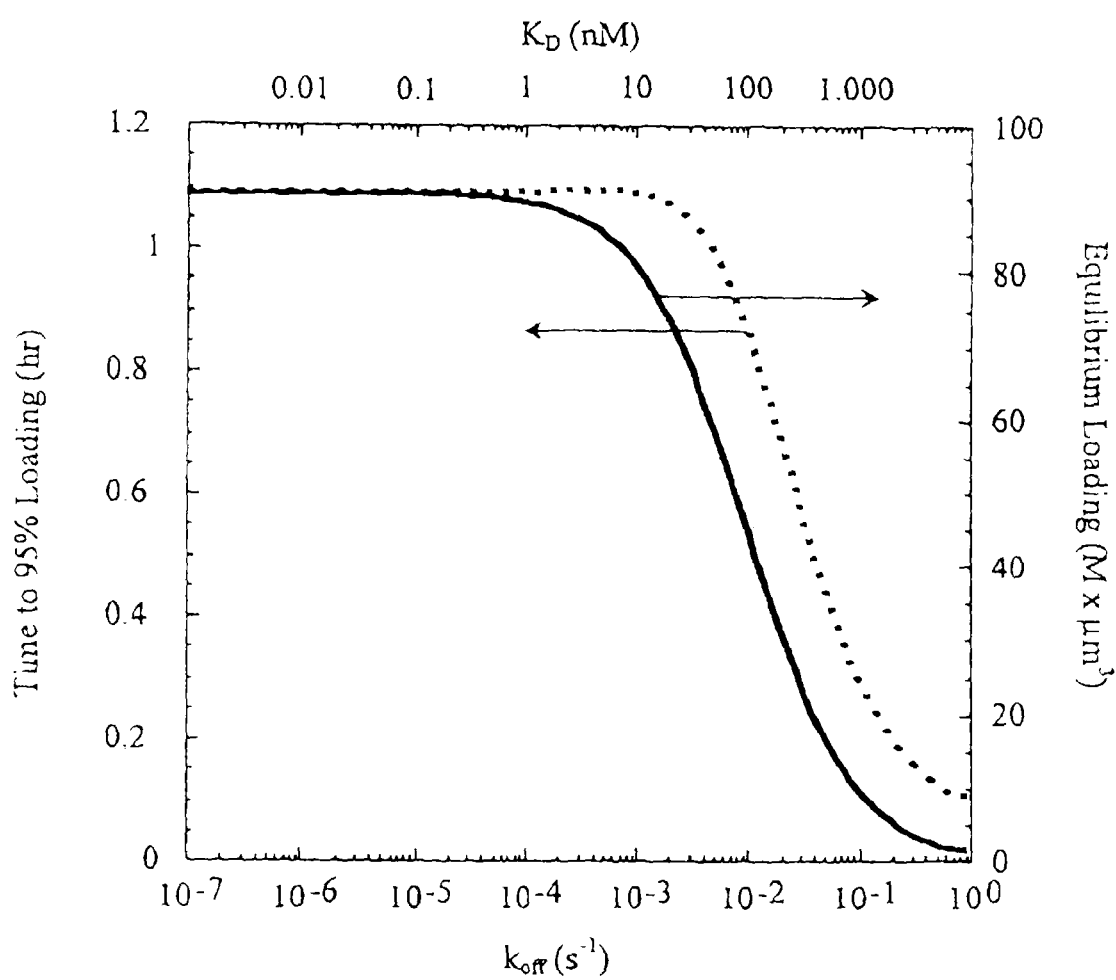
FIG. 3: Effect of Affinity on Time to load and level of loading The simulation was performed for an scFv with a constant antibody concentration of 100 nM and an antigen concentration of 800 nM. Affinities ranging from 1 pM to 1 µM were tested. The time to reach 95% saturation of the tumor, as well as the equilibrium loading concentration were plotted

Inspection of FIG. 2 shows that the lowest affinity antibody ($K_D$=10 nM) examined in this simulation penetrates faster and more uniformly than the other two, suggesting that the use of lower affinity antibodies may be more advantageous. This idea was tested more vigorously with antibodies ranging in affinity from 1 pM to 1 µM. More specifically, the time to reach 95% saturation of the tumor, as well as the equilibrium loading concentration, were simulated as a function of antibody affinity (FIG. 3). As expected, the lower affinity antibodies did in fact penetrate the tumor more quickly. However, the more rapid penetration had an explicit negative result from a therapeutic perspective. The antibody does not bind the antigen to a significant extent at low affinities; hence, at $K_D$>1 µM, penetration is extremely rapid but very little antigen is bound with antibody. These plots illustrate an intrinsic trade-off in these processes. antigen binding slows tumor penetration, but antigen binding is necessary to achieve the therapeutic benefit. It is important to note that the movement of the sharp, slowly moving front of bound antibody reaches the lower limit in speed at a $K_D$=1 nM, and further decrease of the $K_D$ does not slow the movement of the front further. In other words, the "binding site barrier" penalty is fully paid once affinity is sufficiently high for complete antigen binding, and further affinity increases do not incrementally affect the rate of tumor penetration.

Comparison of Simulation to Shrinking Core Model

Figure 4:
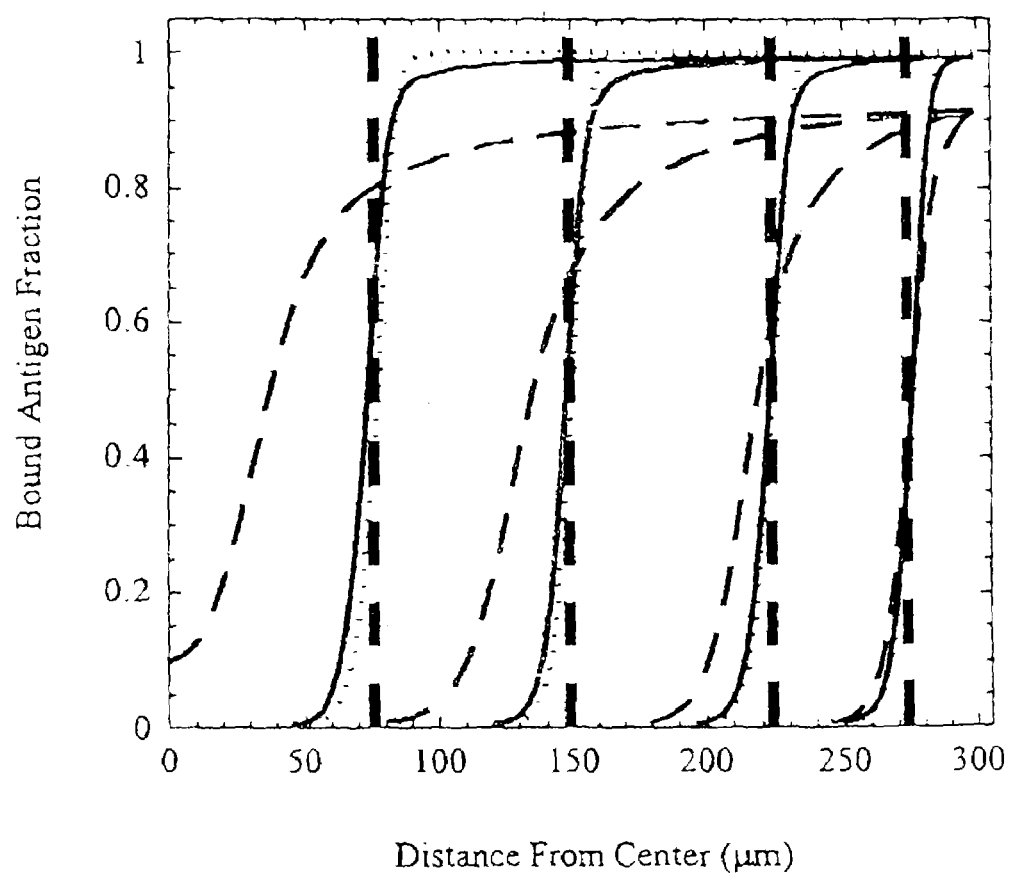
FIG. 4: Shrinking Core Model Moving Front Simulation parameters are described in FIG. 2. The predicted location of the bound antibody front $r_c$ as a function of time is indicated by the dashed vertical line.
Figure 5:
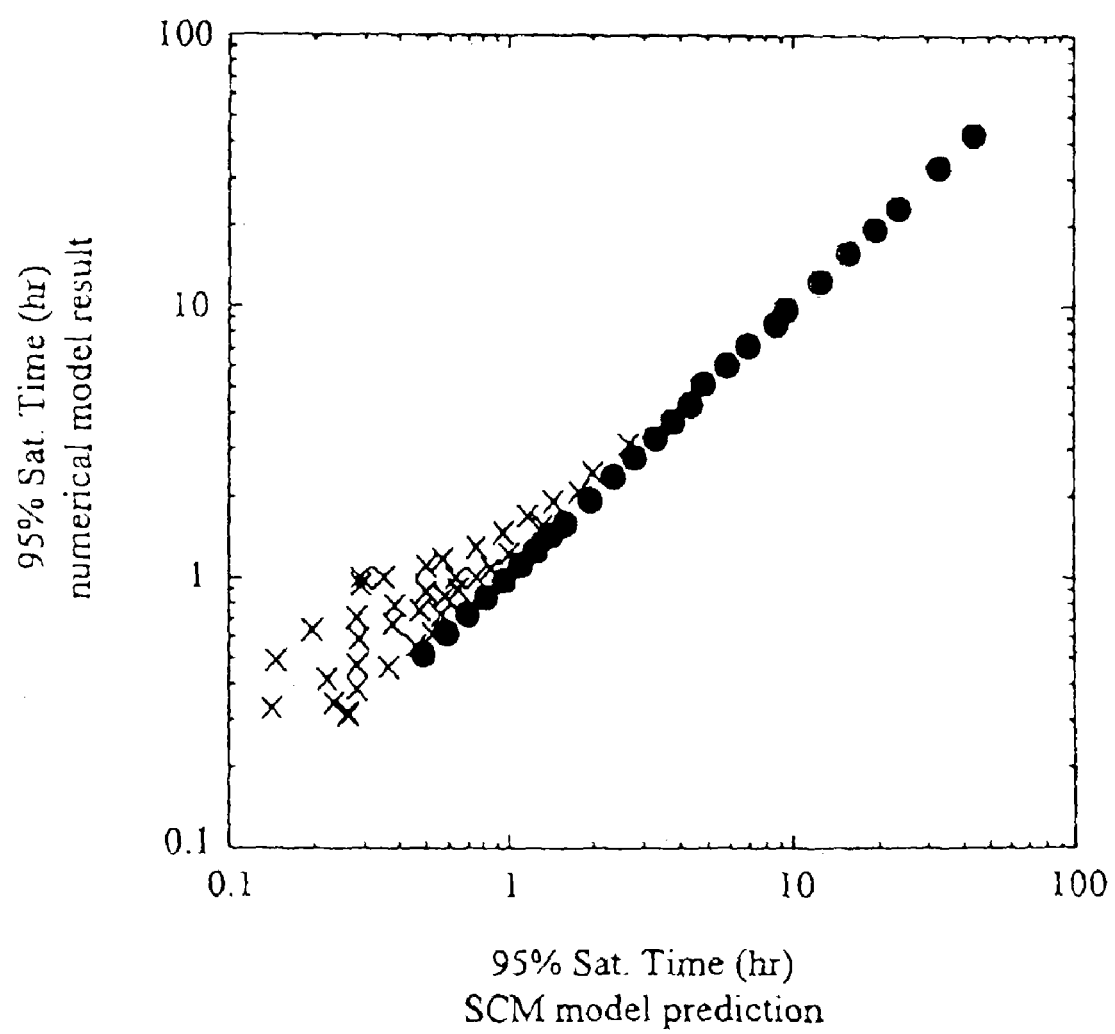
FIG. 5: Comparison of Numerical Simulation to Shrinking Core Model The time to reach 95% saturation of the tumor by the numerical simulation and shrinking core model was compared for a large range of parameters. The parameters tested were: affinity (1 pM–1 nM), antigen concentration (0.4–1.6 µM), antibody concentration (10–1000 nM), tumor size (100–300 um), accessible volume fraction (0.1–0.28), and diffusivity (14–80 µm²/s). IgG (●), scFv (X)

The moving front of antibody penetration shown in FIG. 2 is reminiscent of a similar occurrence described in classic chemical reaction engineering literature. Processes in heterogeneous catalytic particles are sometimes observed to produce such moving fronts with outer shells and inner cores. The Shrinking Core Model (SCM), an analytical method used to describe reaction kinetics in heterogeneous catalytic particles with a shrinking unreacted core, was derived to describe these phenomena. The central assumption of the shrinking core model is that diffusion from the surface of the sphere to the internal reaction front is a slow process, and consumption of the surface reactant is extremely rapid at the reaction front at a critical radius $r_c$. The exact numerical simulations in FIG. 2 were compared to the simplified SCM derived above (FIG. 4). The predicted location of the bound antibody front r, as a function of time is indicated by the dashed vertical line. This location agrees closely with the antibody shell fronts identified for antibodies with affinities of $K_D$=1 nM or lower, indicating that the SCM approximation is reasonable for the high affinity limit. To test the validity of the SCM more rigorously, a range of affinities, antigen concentrations, antibody concentrations, and diffusivities were used. The numerically simulated time for full tumor penetration was compared to the SCM approximated value (FIG. 5). The agreement between the two models is excellent for the IgG parameters, and somewhat less exact for scFv molecules. This discrepancy is most likely due to the fact that single chain fragments have an approximately 6-fold higher diffusivity than IgG molecules. As the diffusivity increases, the central assumption of the SCM model, that consumption of the surface reactant (binding to the antigen in this case) is extremely rapid at the reaction front and that diffusion from the surface of the sphere to the internal reaction front is a much slower process, begins to break down. Nevertheless, the SCM accurately predicts scFv saturation times (within 2-fold) for times less than 0.5 hour, a kinetic regime in which the slowness of tumor penetration is not a practical concern.

One of the most useful features to come out of the SCM derivation for antibody tumor penetration is the term $t_{sat}$. Inspection of the term shows which parameters directly affect the rate of tumor penetration. The parameters R, $Ag_i$, and ε are all related to the tumor physiology and are uncontrollable from the viewpoint of antibody engineering (although antigen concentration has been shown to be manipulated in certain cases). The time to reach saturation increases proportionally to the square of the radius of the tumor as well as the antigen concentration. It decreases with increasing tumor porosity. Terms that are accessible to engineering manipulations are the diffusivity (D) and the antibody concentration ($Ab_0$). The diffusivity is a function of antibody size, and is approximately inversely proportional to the molecular weight. Hence, a smaller scFv would saturate the tumor six times faster than a full sized IgG. Finally, saturation is predicted to be inversely proportional to surface antibody concentration. By doubling this parameter, the time would be cut in half. Perhaps the most interesting information to come out of this analysis is the fact that the parameter of antibody affinity ($K_D$) is not contained in the SCM expression for $t_{sat}$. For conditions well described by the SCM model, tumor penetration speed is independent of binding affinity. (Note, however, that as affinity is lowered to $K_D$>10 nM, the SCM approximation is no longer valid (FIG. 4)).

Figure 6:
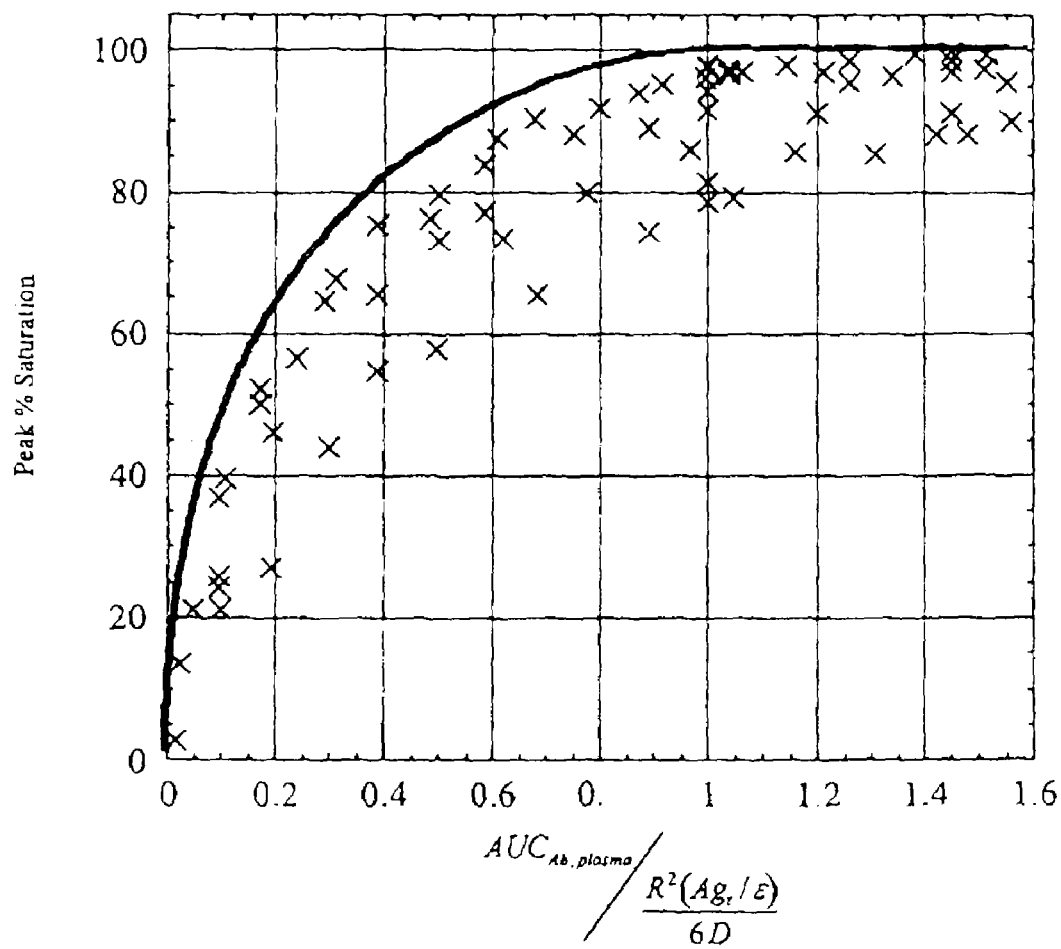
FIG. 6: Shrinking Core Model with Plasma Pharmacokinetics The time to reach 95% saturation of the tumor by the numerical simulation and shrinking core model was compared for a large range of parameters. The parameters tested were affinity (1 pM–1 nM), antigen concentration (0.4–1.6 µM), tumor size (100–300 um), accessible volume fraction (0.1–0.28), diffusivity (14–80 µm²/s), and antibody plasma pharmacokinetics ($\tau_{1/2}$=0.25–2 hours).

Spheroid surface antibody concentration was held constant in all of the simulations presented up to this point. Such conditions could be imposed clinically by steady intravenous infusion. However, single bolus dosing is more generally practiced with antibodies, and so the effect of antibody pharmacokinetics in the plasma is now incorporated into the analysis. First, to what extent can the $t_{sat}$ formalism of the SCM be applied to bolus dosing? For steady antibody concentration, the product $Ab_0 t_{sat}$ is equal to the time integral of the surface antibody concentration, generally referred to as Area Under Curve (AUC). For single exponential antibody pharmacokinetics in plasma, the corresponding AUC is given instead by $Ab_0 \tau_\alpha/\ln 2$, where $\tau_\alpha$ is the plasma half-life for the antibody (FIG. 1). We explored whether the critical antibody AUC value of $R^2(Ag_i/\epsilon)/6D$ would predict tumor saturation values for bolus dosing, and the results are presented in FIG. 6. Given the simplicity of the SCM formalism, the required bolus antibody AUC is remarkably well predicted for a very broad range of parameter values. Hence the SCM makes the following experimentally testable prediction regarding the initial bolus dose required to obtain 95% microspheroid saturation:

$$[Ab]_o = 1.5\left(\frac{(\ln 2)R^2([Ag]_o/\varepsilon)}{6D\tau_{1/2}}\right) \quad \text{Equation 7}$$

Kinetic Phases and Antigen Stability

Figure 7:
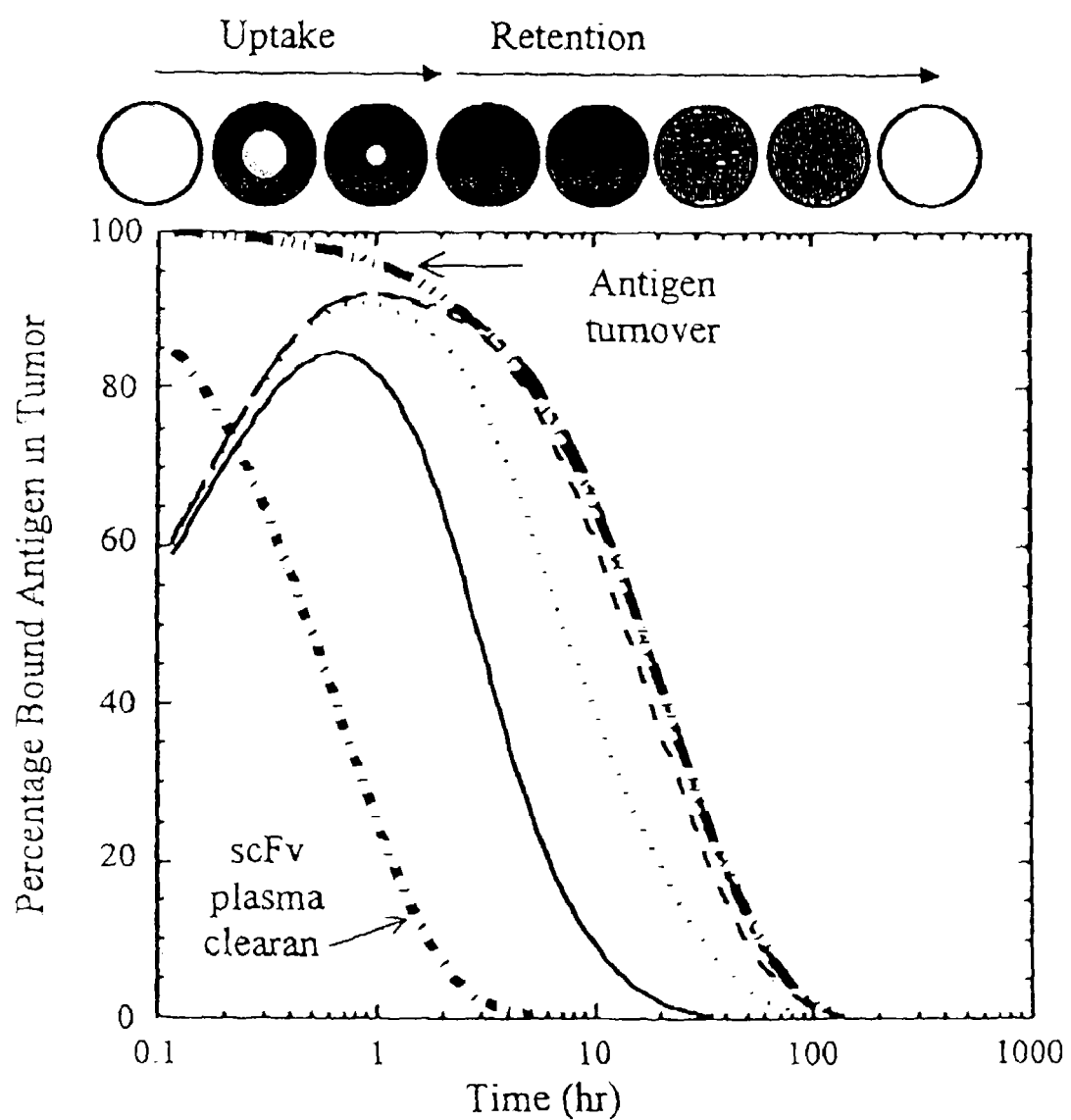
FIG. 7: Kinetic Phases of Loading and Retention Simulations were performed to measure the percentage of antigen bound in the tumor as a function of time and antibody affinity. Antibody penetrates the tumor as in the shrinking core model, and then concentration decreases over time as 1) antibody concentration in the plasma becomes negligible and 2) the antibody dissociates from antigen and/or the antigen is degraded (shed or internalized). The antibody vs. time curves are bound by the antigen degradation curve. Antibody affinities 10 nM (short dashes), 1 nM (alternate long dashes and dots), 100 pM (solid line), 10 pM (dotted line), and 1 pM (long dashes).
Figure 8:
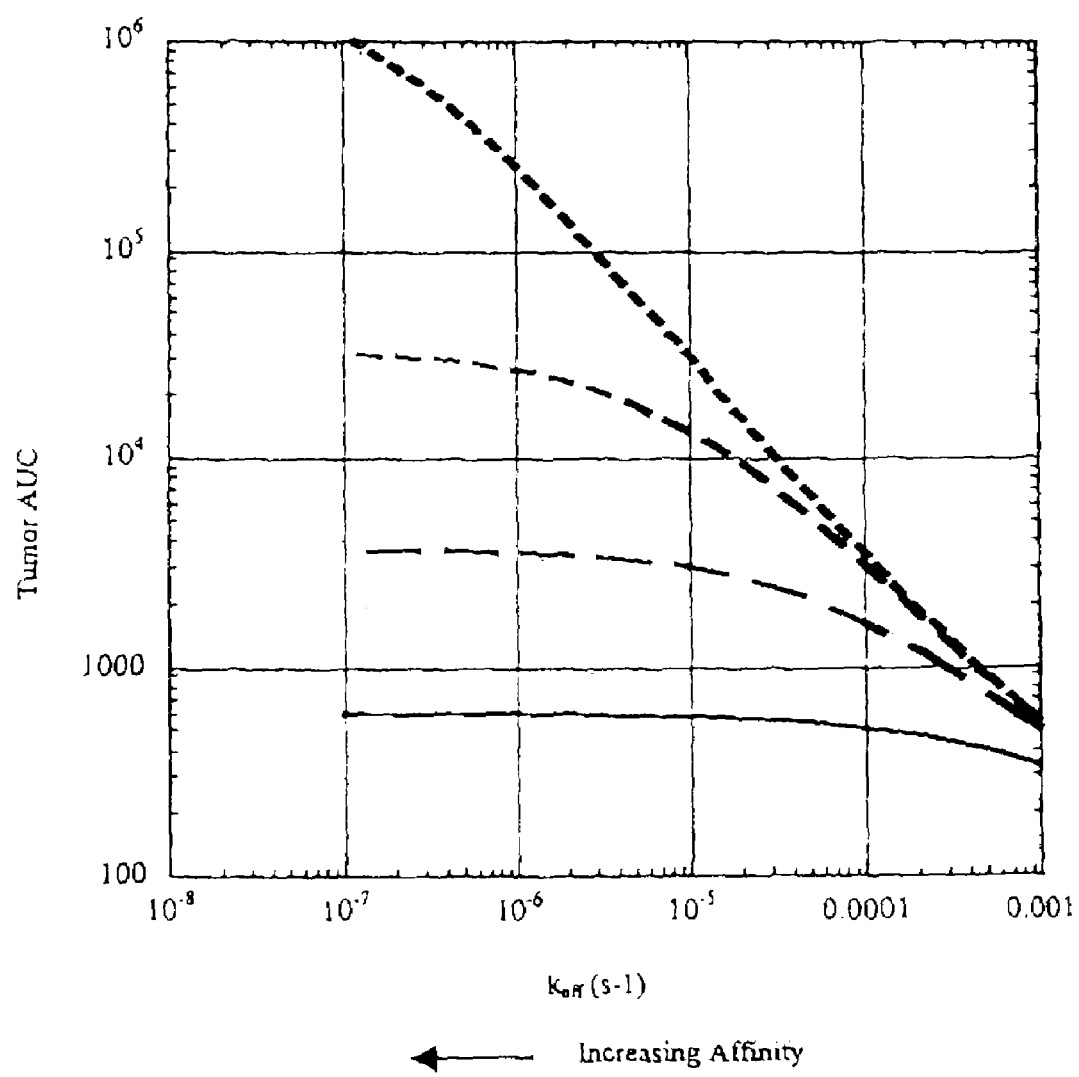
FIG. 8: Effect of Antigen Stability on AUC Simulations were performed with an antibody concentration of 300 nM and an antigen concentration of 840 nM. Antigen stability is represented as follows (curves from upper to lower): $\tau_{1/2}$=2.4 hrs, $\tau_{1/2}$=1 day, $\tau_{1/2}$=10 days, $\tau_{1/2}$=∞.

The time course of tumor antibody exposure can be considered in two qualitatively distinct kinetic phases: 1) uptake by passive diffusion and binding, as described above; and 2) retention of bound antibody in the tumor. The second kinetic phase will now be considered. Simulations were performed with time-varying antibody surface concentrations according to the plasma pharmacokinetic model, and antigen degradation was incorporated into the model. The results are shown in FIG. 7, as a function of antibody affinity. The qualitative shape of bound antibody profiles within the spheroid are represented above the plot. As the bound antibody front penetrates the sphere, one obtains an SCM-like distribution. However, following tumor saturation, the decrease in bound antibody occurs more uniformly throughout the tumor. Thus, the overall process can be broken into two distinct kinetic phases: tumor uptake, dominated by diffusion and well-described by the SCM; and tumor retention, dominated by (as demonstrated below) antigen turnover rate.

As a highly simplified measure of antibody pharmacodynamics, it is assumed that the time integral of the bound antibody within the spheroid is a gross measure of antibody effect on the tumor. This quantity, termed $AUC_{tumor}$, is the area under the curves in FIG. 7. Although one would not necessarily expect a linear relationship between $AUC_{tumor}$ and tumor cell killing, one might well expect a monotonic relationship, such that increased antibody exposure kills more tumor cells. Further expansion of this pharmacodynamic relationship for the various different potential payloads (radioisotopes, prodrug-cleaving enzymes, Fc-mediated ADCC, etc.) is beyond the scope of this chapter.

In FIG. 7, note that $AUC_{tumor}$ increases markedly when affinity is increased from 10 nM to 1 nM, less so for an increase from 1 nM to 100 pM, and almost negligibly for a 100-fold further improvement of affinity to $K_d$=1 pM. Note also that antibody vs. time curves are bounded by the curve for antigen degradation.

As evidenced by FIG. 7, the therapeutic benefit of antibody therapy is limited by the antigen elimination. While many studies have focused on ranges in antibody affinities and antigen concentration, none to date have explicitly examined the role of antigen degradation on the effectiveness of treatment. Physiologically, the target antigen can be internalized or shed at significantly different rates. For example, erbB2 is internalized at a rate of $6.67 \times 10^{-4}$ s$^{-1}$, µ is internalized at a rate of $1.9 \times 10^{-4}$ s$^{-1}$, CD20 is shed at a rate of $8.0 \times 10^{-6}$ s$^{-1}$, and CEA is shed at a rate from $1.2–80 \times 10^{-6}$ s$^{-1}$ (Worthylake et al., 1999, Press et al., 1994, Stein et al., 1999). For this reason, the AUC delivered to the tumor was simulated as a function of both the antibody affinity and antigen stability (FIG. 2.8). For an antigen with a half-life of 2.4 hours, an affinity improvement from 1 nM to 1 pM (1000-fold) led to a rather disappointing 2-fold increase in the dose delivered to the tumor. Conversely, an antigen with a half-life of 10 days will result in a 50-fold increase in the therapeutic dose delivered to the tumor for the same 1000-fold affinity improvement. It can be easily seen that success of antibody based therapy is directly related to the antigen stability, such that targeting an antigen with a fast internalization or shedding rate will show little incremental benefit for large improvements in affinity. In other words, there is no advantage to engineering antibodies that bind an antigen that is no longer present.

Model Validation with Experimental Data

In order to test the accuracy of the model to predict results for in vivo testing of antibodies, several published experimental studies were selected for comparison. These studies examined the role of affinity and antibody molecule type on success of treatment. Several antigens were targeted, including erbB2, CEA, and EGFRvIII. In many cases, data published in these studies is in the form of percentage of injected dose retained per gram of tumor (% ID/g) at a given time point. While absolute direct number comparisons cannot be made with simulation data, relative trends can be observed.

Figure 9:
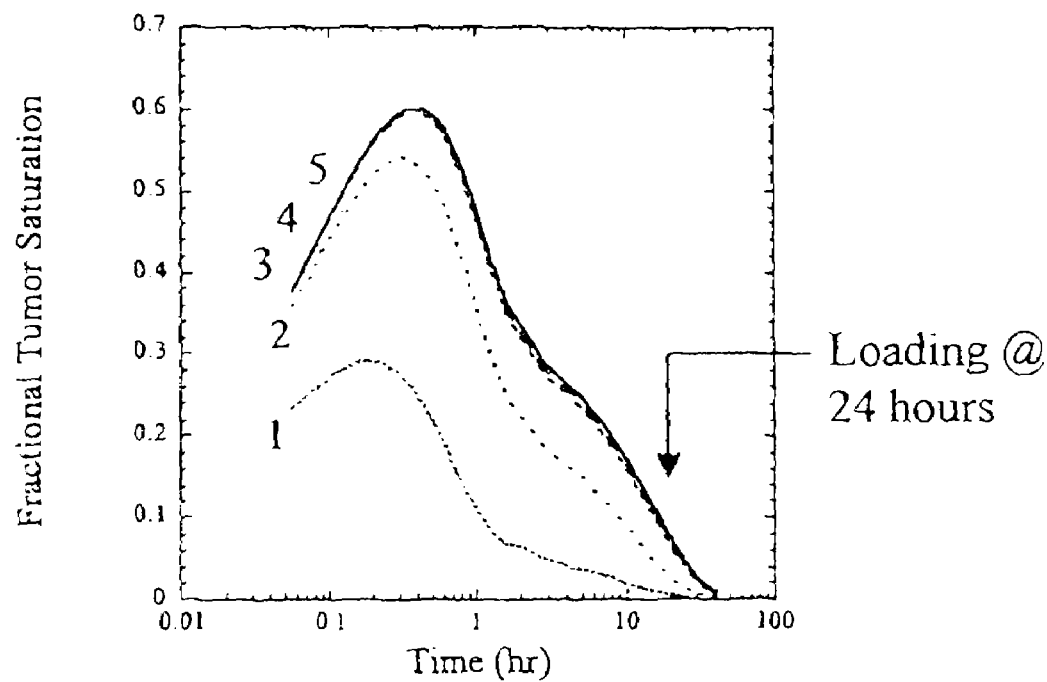
FIG. 9: Comparison to anti-erbB2 antibody fragments Simulated results were compared to data from Adams et al., Cancer Res. 61: 4750, 2001. (A) Fractional tumor saturation profile from simulation for the series of scFvs (B). The antibody loading value at 24 hours from the simulation compared to the antibody retained (% ID/g) in the biodistribution study. C6G98A: $\tau_{1/2}$~5 sec (1); C6.5: $\tau_{1/2}$~110 sec (2); C6ML3–9: $\tau_{1/2}$~15 min (3); C6MH3-B1: $\tau_{1/2}$~3 hrs (4); C6-B1D2: $\tau_{1/2}$~19 hrs (5).
Figure 9:
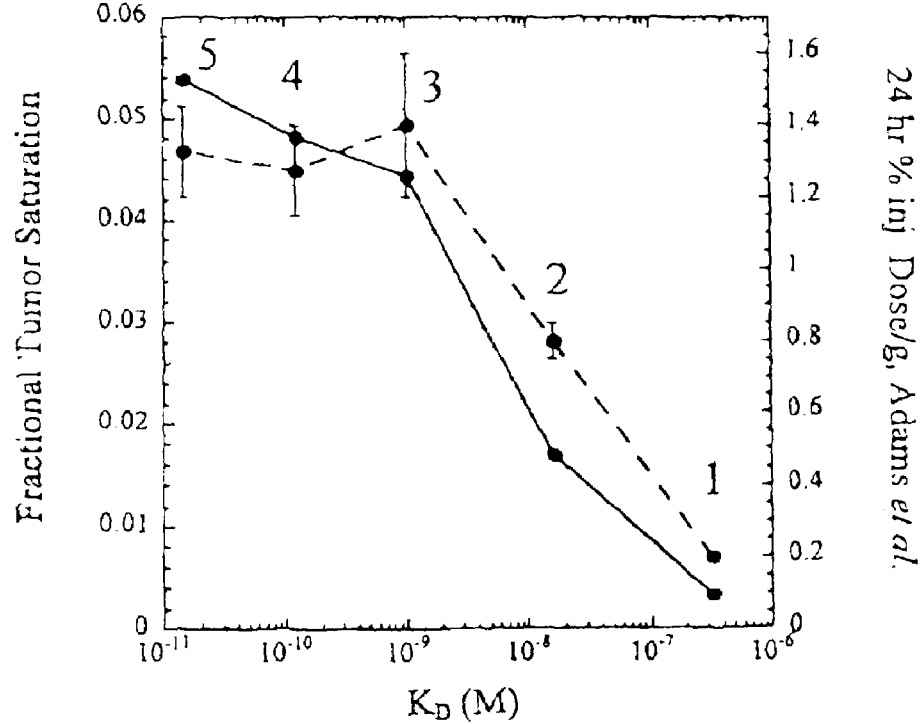

The first study examined the effect of a 5000-fold improvement in affinity for scFvs targeting tumors expressing erbB2 (Adams et al., 2001). Specific experimental conditions are listed in table 3. These same conditions were used in the simulation. For the simulation, the amount of the antibody retained in the tumor over time increases with increasing affinity up to a $K_D$ equal to 1 mM (FIG. 9A). By taking the simulation value at 24 hours, this can be compared to experimentally measured % ID/g (FIG. 9B). There is excellent agreement between the simulated and experimental data. For both cases, the % ID/g of tumor increases up to a $K_D \approx 1$ nM, where the value plateaus. This result can be explained by examining the biological properties of the targeted antigen. ErbB2 is constitutively internalized at a rate of $6.67 \times 10^{-4}$ s$^{-1}$ ($\tau_{1/2}$=17 minutes) (Worthylake et al., 1999). Engineering antibodies to bind with a half-life greater than 17 minutes would be of no advantage because the antigen's time stability dictates that it would not be present. This is the reason the two higher affinity antibodies, $K_D$=120 pM ($\tau_{1/2}$=3 hours) and $K_D$=15 pM ($\tau_{1/2}$=15 hours), perform no better than the antibody with a dissociation constant of 1 nM ($\tau_{1/2}$=15 minutes).

Figure 10:
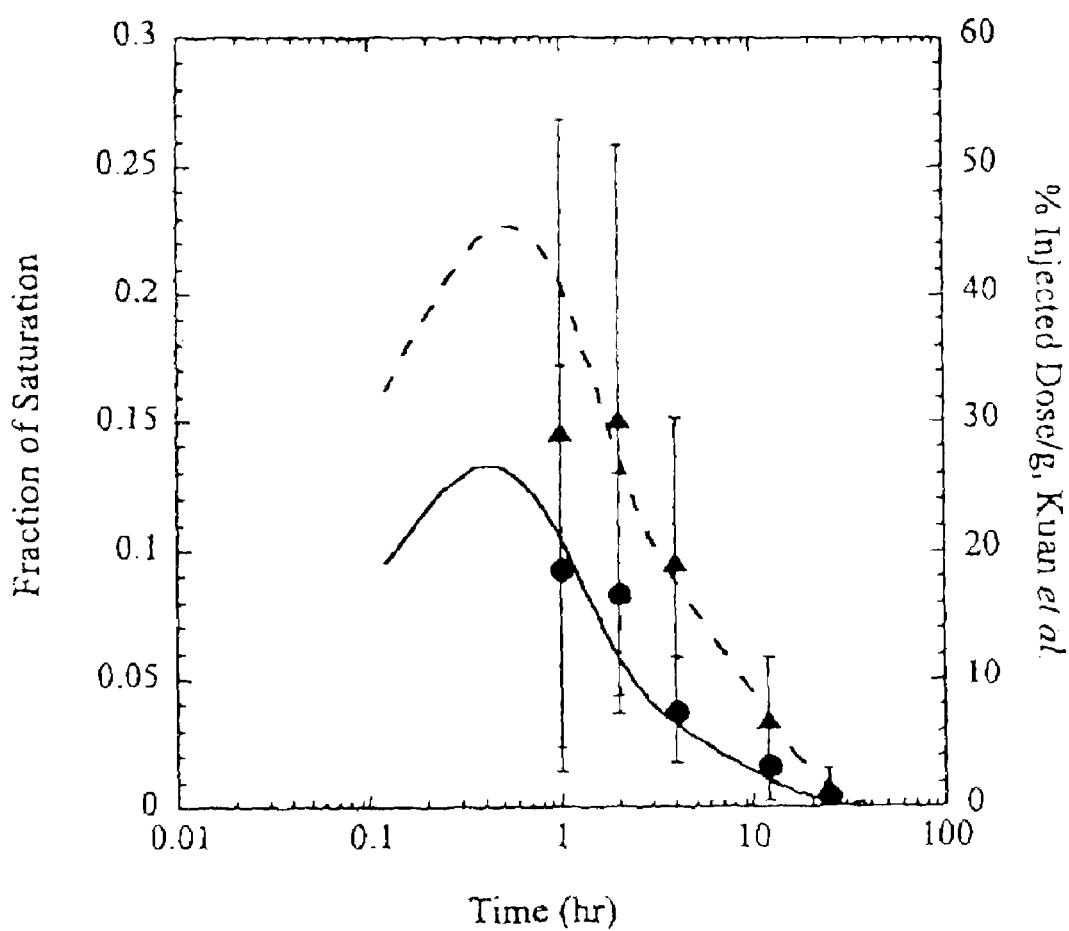
FIG. 10: Comparison to anti-EGFRIII antibody fragments Simulated results were compared to data from Bigner et al., Int. J. Cancer 88:962, 2000. Fractional tumor saturation profile from simulation for MR1: $K_D$=23 nM (solid line) and MR1-1: $K_D$=1.5 nM (dashed line). Percent injected dose per gram of tumor (% ID/g) from experimental data for MR1: $K_D$≈23 nM (●) and MR1-1: $K_D$=1.5 nM (▲).

The second paper studied two scFvs with a 15-fold difference in affinity. These antibodies targeted an epitope on EGFRvIII. Experimental conditions selected from the paper to be used in the simulation are summarized in Table 4. In this study, % ID/g was measured at five time points for both of the antibodies. Once again, there is good correlation between the simulated results and those measured in the biodistribution study (FIG. 10). For the higher affinity antibody ($K_D$=1.5 nM, $k_{off}$=1.2×10$^{-3}$ s$^{-1}$), the amount retained in the tumor is approximately two times higher than for the lower affinity antibody ($K_D$=23 nM, $k_{off}$=2.1×10$^{-3}$ s$^{-1}$). In this particular study, the antibody was injected directly into the tumor, which accounts for the much higher tumor retention (% ID/g) than that attained with the scFvs that targeted erbB2.

Figure 11:
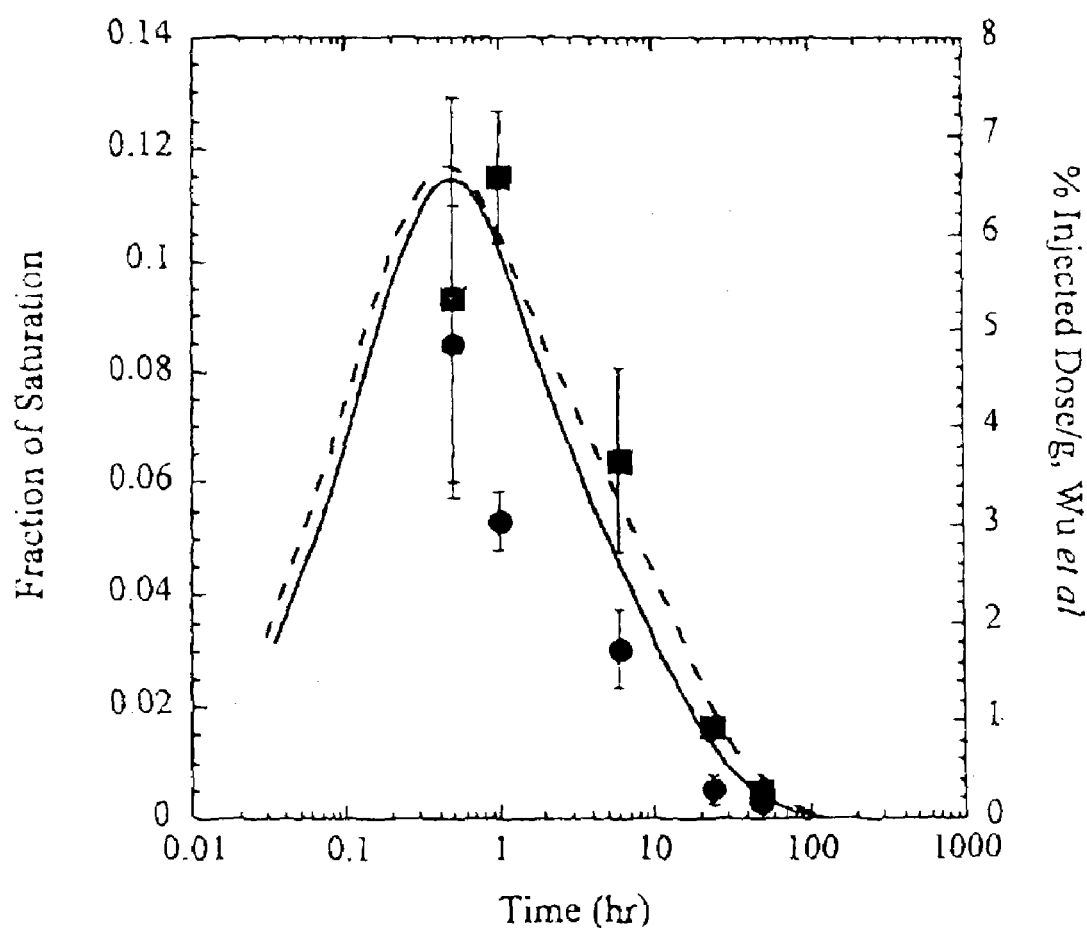
FIG. 11: Comparison to anti-CEA antibody fragments Simulated results were compared to data from Wu et al., Immunotechnology 2: 21, 1996. Fractional tumor saturation profile from simulation for T84.66/C28: $K_D$=0.45 nM (solid line) and T84.66/212: $K_D$=0.24 nM (dashed line). Percent injected dose per gram of tumor (% ID/g) from experimental data for T84.66/C28: $K_D$≈0.45 nM (●) and T84.66/212: $K_D$=0.24 nM (■).
Figure 12:
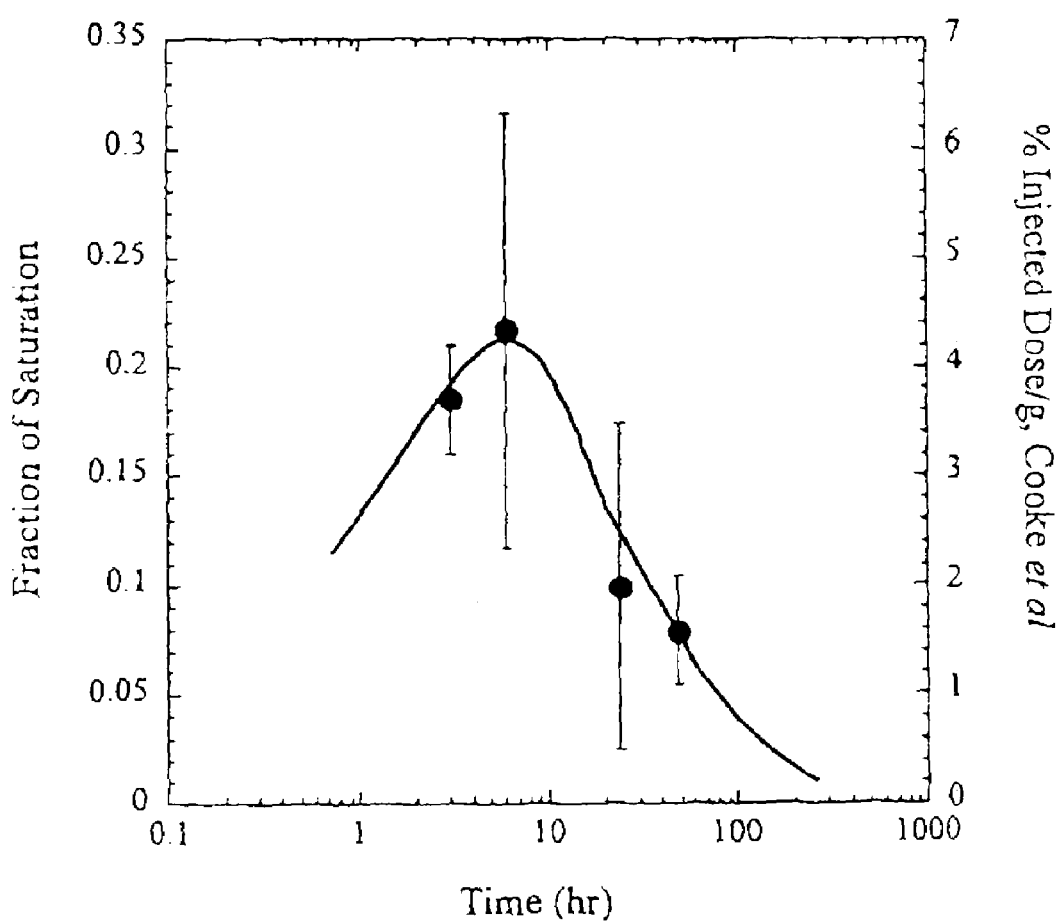
FIG. 12: Comparison to anti-CEA scFv-fusion protein Simulated results were compared to data from Cooke et al., Bioconjugate Chem. 13:7, 2002. Fractional tumor saturation profile from simulation for MFE-23 scFv/TNFα fusion protein (solid line). Percent injected dose per gram of tumor (% ID/g) from experimental data for MFE-23 scFv/TNFα fusion protein (●).

The final two papers investigated several antibody molecules targeting carcinoembryonic antigen (CEA). Wu et al. studied two scFvs, constructed from the same monoclonal antibody (T84.66), but with amino acid linkers of different lengths connecting the variable fragments (Wu et al., 1996). T84.66/C28 was connected by a 28 amino acid linker ($V_H$-linker-$V_L$ orientation, $K_D$=0.45 nM) and T84.66/212 was connected by a 14 amino acid linker ($V_L$-linker-$V_H$ orientation; $K_D$=0.24 nM). Simulated results compared well with biodistribution data for T84.66/212; however, experimental results for T84.66/C28 were lower than that predicted by the simulation (FIG. 11). The linker used to construct T84.66/C28 may account for its poor performance. The longer linker may have interfered with association of the variable domains, making the fragment less stable and more vulnerable to protease degradation. The orientation of the fragment may have resulted in lower stability as well. If the C28 scFv was destabilized, the effective concentration of antibody in the bloodstream would be lower than the amount injected, which could lead to the discrepancy between simulated and experimental results. Cooke et al. examined the tumor targeting properties of a single chain antibody fragment/tumor necrosis factor fusion protein (Cooke et al., 2002). This fusion protein forms a trimeric structure of 144 kDa, approximately the same size as a full IgG antibody molecule. The fusion protein was radiolabeled with $^{125}$I and percent injected dose per gram of tumor was measured at 3, 6, 24, and 48 hours post injection. Experimental conditions selected from the paper to be used in the simulation are summarized in Table 6. As compared to the other simulated data sets, the larger antibody fragment in this study reaches maximal saturation at a later time point (~6 hours vs 30 minutes for the scFvs), which would be expected due to slower diffusion. The model once again does a good job in capturing the trend of antibody retention over time for this antibody and antigen system (FIG. 12).

Discussion

In this study, a mathematical model was developed to gain an improved understanding of the quantitative interplay among the rate processes of diffusion, binding, degradation, and plasma clearance in tumor microspheroids. This model was based largely on that derived by Weinstein and coworkers, with minor modifications. For example, as in Weinstein's models, convection was not incorporated into the model, leaving diffusion as the only process by which the antibody can penetrate the tumor. Through analysis of the simulation results and comparison to published experimental data, the goal was to understand the key variables for loading of the antibody and maximal tumor retention. With this information, it would be possible to design the optimal targeting agent.

The first area addressed was the impact of affinity on tumor penetration. With Weinstein's paper in 1987 introducing the concept of the binding site barrier, many investigators believed that the advantage of longer binding of high affinity antibodies did not outweigh the disadvantage of non-homogenous distribution of antibodies in the tumor. Experimental results also supported the binding site barrier hypothesis (Juweid et al., 1992). The limitation in many of the experimental approaches, however, was that low antibody concentrations used in biodistribution studies restricted the broad interpretations of the results. The analysis above shows a more accurate representation of the process by which an antibody penetrates the tumor. As a binding entity, the antibody molecule will diffuse through the tumor until it encounters free antigen that it can bind to. As available antigen is saturated, the antibody will continue to penetrate the tumor as a moving front, until all antigen is bound. Several papers which support the binding site barrier hypothesis also acknowledge that this effect can be overcome with an elevated antibody dose. Simulations performed in this study did confirm that lower affinity antibodies will in fact penetrate the tumor faster. However, the trade-off for this faster penetration is a lower level of antibody loading in the tumor, which is directly correlated to the therapeutic value of the antibody. This is another limitation to some of the previous experimental work (Saga et al., 1995). It has been hypothesized that antibody molecules must have an affinity greater than one nanomolar ($K_D < 10^{-9}$ Molar) to provide effective results (Schier et al., 1996). By comparing a high affinity antibody ($K_D < 10^{-9}$ M) to a non-binding antibody or one with very low affinity, conclusions can be somewhat misleading. There is a cost associated with binding to the antigen, but the cost does not continue to increase as the affinity increases. For antibodies with a dissociation constant equal to 1 nM (the point at which they are therapeutically valuable), the slowly moving front of bound antibody has reached its limit.

The observation that the antibody penetrates the tumor as a shell provides an opportunity for comparison to a well established model system. The Shrinking Core Model (SCM), derived to describe the reaction kinetics in heterogeneous catalytic particles with a shrinking unreacted core, has a diffusion and reaction profile similar to that shown for antibody molecules in a tumor. The analytical solution using the SCM shows excellent agreement with the simulation results across a broad range for several parameter values. The value of the derivation of the shrinking core model in terms of antibody penetration is the relationship that is developed between the time to reach tumor saturation and the other parameters (Equation 6). While certain parameters that affect saturation time are strictly defined by the tumor of interest (radius and antigen concentration), others can be controlled by the investigator (diffusivity, antibody concentration, and accessible volume fraction). Most notably, the antibody affinity has no impact on the saturation time. This simplified analytical approach can provide a roadmap for designing antibody molecules and treatment methods that provide the most optimal conditions for tumor penetration.

The benefit of high affinity antibodies would be seen in the retention of the antibody in the tumor. The time integral of the bound antibody in the tumor (AUC) is a measure of the antibody effect on the tumor. The percentage of the injected does per gram of tumor (% ID/g) is also a term used to measure the amount of the antibody retained at given time points. Several studies have found that high affinity antibodies (those with slower off-rates) do persist at the tumor longer than their lower affinity counterparts (Juweid et al., 1992, Viti et al., 1999, Kuan et al., 2000, Adams et al., 2001). However, this relative increase in tumor retention does not always seem to correlate with the increase in antibody affinity. One factor that significantly affects retention is the stability of the target antigen. If the antigen is shed from the surface or internalized at a fast rate (on the order of minutes to hours) and an antibody is designed to bind with a half-life on the order of days, very little improvement will be seen in the tumor retention for the ultra high binder versus one that bound on the order of hours. The simulations were performed in this study to explicitly examine the effect of antigen stability on tumor antibody retention. This work showed that the elimination rate of the target antigen was of critical importance to the change in the therapeutic effect of antibodies with increasing affinity. Antigen stability had not been investigated in previous modeling work.

It was also necessary to test the accuracy of the model for predicting in vivo antibody targeting results. Simulation results are measured as the fraction of antibody saturation in the tumor at a given time point. Experimental biodistribution data is often measured as the percentage of injected dose retained per gram of tumor (% ID/g). While absolute direct numerical comparisons cannot be made with simulation data, trends can be observed. To do this, several papers were selected from the literature. The first paper studied single chain antibody fragments targeting erbB2 that spanned four orders of magnitude in their off-rate. These scFvs were one of the first successes to show the ability of antibody engineering techniques to significantly improve off-rate kinetics (Schier et al., 1996). However, when their tumor targeting properties were examined in vivo, the results were less than encouraging (Adams et al., 2001). The conditions used in the biodistribution studies were used to simulate the tumor retention for comparison. The results from the model exhibited the same trend as the animal experiments, with a continued increase in retention of the antibodies with an affinity up to 1 nM ($k_{off} = 10 \times 10^{-3}$ s$^{-1}$). The two higher affinity antibodies showed no statistical increase over the 1 nM scFv. While these results may appear to support the "binding site barrier" hypothesis, the outcome is actually dependent on the stability of erbB2. The targeted antigen is constitutively recycled with a half-life of approximately 17 minutes (Worthylake et al., 1999). Accordingly, antibodies with half-lives greater than the antigen half-life would show no additional benefit, as was the case here. Using the model prior to the experimental study would have predicted the plateau in the antibody retention that occurred as a result of the antigen internalization.

An additional paper was selected to see if the model could predict the antibody retention of scFvs at multiple time points, as compared to the single time point in the erbB2 study. An scFv was affinity matured by hot-spot mutagenesis to produce a variant that has an approximate 2-fold improvement in the off-rate (15-fold affinity improvement) (Beers et al., 2000). These two scFvs were then compared in simultaneous biodistribution studies by labeling each with a different radioisotope (Kuan et al., 2000). The modeling results were in good agreement with the experimental results for all five time points, ranging from 1 hour to 24 hours. For both results, the higher affinity antibody exhibited approximately 2-fold higher retention than the parental molecule. Once again, the model succeeded in predicting the relative retention of the two scFvs over the time course of the study.

The final papers examined the retention of several antibody molecules against carcinoembryonic antigen. CEA has been shown to be very stable, with a half-life ranging from one to seven days (Stein et al., 1999), and is one of the most stable antigens used for tumor targeting purposes. Because of its increased stability in comparison to erbB2 and EGFR, CEA biodistribution studies were selected for comparison to simulation data. Wu et al. studied scFvs and Cooke et al. studied a lager scFv-fusion protein (144 kDa). Simulated antibody retention showed a good correlation with experimental data for one scFv (T84.66/212) at several time points, but not the other (T84.66/C28). Since these two scFvs are comprised of the same variable fragments in different orientations and connected with linkers of different lengths, some other property is likely affecting the tumor retention. The T84.66/C28 scFv has a longer linker (28 amino acids) which may lead to lower stability. If the C28 scFv was destabilized, the effective concentration of antibody in the bloodstream would be lower than the amount injected. Although stability of the scFvs were not addressed in this study, lower stability may account for the discrepancy between the simulated and experimental results for the C28 scFv. Given that biodistribution data from single chain antibody fragments has only been analyzed thus far, the scFv-fusion protein was selected for comparison to study the models ability to predict antibody retention for larger antibody molecules. As compared to the other simulated data sets, the larger antibody fragment in this study reached maximal saturation at a later time point (~6 hours vs ~30 minutes for the scFvs), which would be expected due to slower diffusion. The simulation prediction of peak saturation matches with the experimental results. Additionally, there is qualitative agreement between the simulation and experimental results for the scFv-fusion protein.

In this study, a mathematical model was developed to gain an improved understanding of the quantitative interplay among the rate processes of diffusion, binding, degradation, and plasma clearance in tumor microspheroids. Observation that the antibody penetrated the tumor as a moving front allowed for comparison to the "shrinking core model" (SCM), derived to model particulate combustion or catalyst regeneration in classical chemical engineering literature. The SCM provides a simple analytical method that will be useful for predicting the effects of altered antibody pharmacokinetics, antibody molecular weight, antigen turnover rate, antigen expression level, and micrometastases size on antibody penetration and retention. Through analysis of the simulation results and comparison to published experimental data, we have also been able to discern the key variables for loading of the antibody and maximal tumor retention. Optimal loading favors the use of highly diffusible, small antibody fragments. Additionally, affinity is irrelevant and does not restrict penetration for antibodies with a $K_D$<1 nM. There are several key variables for retention of the antibody in the tumor. Stability of the antigen is of critical importance, since an antibody will not remain bound to an antigen that has been shed or internalized and degraded. Also, the antibody should be engineered to bind the antigen with an off-rate less than or equal to the degradation rate of the antigen.

Example 2

Design of a Stable, High Affinity Single Chain Antibody Against Carcinoembryonic Antigen for use in Tumor Immunotherapy Introduction In this study, MFE-23 was engineered to increase the retention time of the antibody in the tumor relative to normal tissue. This was accomplished through partial humanization of MFE-23, and maturation of the affinity and stability of the scFv. Since MFE-23 was isolated from a murine phage library, there exists the possibility that its administration may elicit an immune response. This could in turn decrease the lifetime of the antibody in circulation. In order to reduce the likelihood of immunogenicity, the antibody was resurfaced to present a more "human" Fv framework surface (Pedersen et al., 1994; Roguska et al., 1994). The crystal structure of MFE-23 shows structural similarity to another crystallized human antibody) (Boehm et al., 2000). This resemblance allowed for the determination of twenty-eight residues in MFE-23 that were over 30% solvent-accessible and chemically different or similar to the human antibody (TR19)(Boehm et al., 2000). For humanization of MFE-23, the residues suggested in Boehm et al. were changed to the corresponding residues in the human antibody. Equilibrium titration verified that altering these twenty-eight residues resulted in no detectable change in CEA binding affinity. This resurfaced scFv is termed hMFE.

Increased affinity of the hMFE scFv may increase retention time of the antibody in a tumor (cf Osbourn et al., 1996) and as predicted by mathematical modeling (See Example 1). A critical parameter determining tumor retention is the off-rate ($k_{off}$). After two rounds of mutagenesis and screening, several variants of hMFE were isolated which showed a 10-fold, 100-fold, and 1000-fold improvement in the off-rate over the original scFv, hMFE. The greatest improvement corresponds to a half-life for binding to CEA of approximately 7 days (versus 10 minutes for hMFE).

A final parameter addressed in this study was the stability of the scFv. In order to function in a therapeutic setting, the scFv must be resistant to thermal denaturation at 37° C. (Willuda et al., 1999). Furthermore, stability has been shown to correlate closely with expression efficiency (Shusta et al., 1999), and the affinity matured hMFE mutants were found to express poorly. Affinity improved mutants were subjected to stability maturation. All stability improved mutants retained their affinity gains and soluble expression levels were greatly increased. Yeast cells displaying the stabilized, highest affinity mutant retained approximately 80% binding after incubation at 37° C. for 9 days. In addition, this mutant had comparable thermal stability to the wild-type hMFE scFv after restabilization.

It is important to note that the off-rate achieved in this study is amongst the slowest known for antibody-protein antigen interactions. A further special significance of our panel of very stable antibody fragments is that they span three orders of magnitude in off-rate improvement. This series of scFvs will enable us to confirm the impact of increased affinity on efficacy in anti-CEA tumor therapy.

Experimental Protocol

Cloning of MFE-23 and bMFE Surface Display Plasmids

The MFE-23 scFv was PCR'ed from the MFE-23his vector (Casey et al., 1995) with the MFEtop and MEEbot primers (SEQ ID NOS: 7 & 8). The resulting 750 bp fragment was digested with NheI and BamHI, gel purified, and ligated into the yeast surface display vector, pCTCON. The pCTCON vector is a variant of pCT302 (Boder and Wittrup, 1997) that contains a unique BamHI site 5 to the c-myc coding sequence. Twenty-eight residues of the MFE-23 scFv were identified for resurfacing (Boehm et al., 2000). The resurfaced humanized version (hMFE) was designed using yeast optimum codons with a NheI site immediately 5' to the gene and a BamHI site immediately 3' to the gene. The gene was synthesized by Synthetic Genetics (San Diego, Calif.). The hMFE scFv was excised from the Synthetic Genetics vector with NheI and BamHI and cloned into pCTCON. The two display vectors, pCTMFE23 and pCThMFE were transformed into yeast strain EBY 100 (Boder and Wittrup, 1997) by the lithium acetate method of Gietz and coworkers (see tto dot trends dot com). To test expression of the Aga2p-MFE-23 and Aga2p-hMFE fusions, cells were grown at 30° C. for 24 hours in SD-CAA (2% dextrose, 0.67% yeast nitrogen base, 1% casamino acids) to an OD600=5.0–7.0. Cells were then transferred to SG-CAA (2% galactose, 0.67% yeast nitrogen base, 1% casamino acids) to a starting OD600 =1.0 and grown for 16–20 hours at 20° C. or 37° C.

To perform an equilibrium titration, cells displaying the MFE-23 and hMFE scFvs were labeled at multiple concentrations with biotinylated-CEA and incubated at 37° C. for 1–24 hours. In order to limit depletion of antigen, labeling volume was increased with decreasing CEA concentration. Cells were washed with cold PBS-BSA and labeled with a 1:100 dilution of biotinylated-9E10 on ice. Cells were washed and labeled with secondary reagents goat-anti-mouse-FITC (1:50) (Sigma) and streptavidin-PE (1:100) (Pharmingen) on ice. Cells were washed and resuspended for analysis on a Coulter EPICS XL. The mean fluorescence of the labeled population was plotted against the CEA concentration, and data was fit to calculate the dissociation constant.

MFE-23 PCR Primers

```
                                              (SEQ ID NO: 7)
MFEtop
5'-GTCAGTGCTAGCCAGGTGAAACTGCAGCAGTCTGGG-3'

(SEQ ID NO: 8)
MFEbot
5'-GTTCACGGATCCTGCTTTCAGCTCCAGCTTGGTGCCAGC-3'
```

NhE I restriction site single underline BamHI site double underline.

Soluble Production and Detection of MFE-23 and hMFE

The pCTMFE-23 and pCThMFE vectors were digested with NheI and XhoI. The digests were isolated on a 1% agarose gel and the 750 bp scFvs were excised from the gel and purified with the Qiagen gel purification kit. The scFv was ligated into the pRS4420 vector (Boder et al., 2000), which was also digested with NheI and XhoI and gel purified. The new vectors, pRSMFE-23 and pRShMFE, were digested with BamHI and XhoI to remove the c-myc epitope tag. The digests were isolated on a 1% agarose gel and the .about.6700 bp backbone was purified with the Qiagen gel purification kit. The oligos, HIStop and HISbot (SEQ ID NOS: 9 & 10), were annealed and ligated into the backbone. The resulting vectors, MFE23-his and hMFE-his, contain the scFv followed by a c-terminal 6-histidine tag. The two secretion vectors, MFE23-his and hMFE-his, along with the pRS314 vector were transformed into yeast strain YVH10 (Shusta et al., 1998) by the lithium acetate method of Gietz and coworkers (see tto dot trends dot com). To test soluble expression of the scFvs, cells were grown at 30° C. for 48 hours in SD-SCAA (2% dextrose, 0.67% yeast nitrogen base, 1% synthetic casamino acids (ura-, trp-, leu-)) to an OD600=5.0–7.0. Cells were pelleted and resuspended in SG-SCAA (2% galactose, 0.67% yeast nitrogen base, 1% casamino acids (ura-, trp-, leu-) supplemented with 1 mg/ml of BSA) and grown for 36–48 hours at 20° C. or 37° C.

For detection of the scFv, samples were run on a 12% polyacrylamide gel and then transferred to a nitrocellulous membrane. The membrane was blocked in a milk solution (1.5 mg nonfat dry milk in 30 ml TBST (8 g/L NaCl, 3.6 g/L Tris Base, 1 ml/L. Tween 20 solution (pH=7.6)) at room temperature for 1 hour. Membrane was washed 1×15 minutes, 2×5 minutes in 30 ml TBST. Membrane was incubated with the tetra-his antibody (Qiagen) (1:800 dilution) for 1 hour at room temperature and was washed 1×15 minutes, 2×5 minutes in 30 ml TBST. The membrane was incubated with a goat-anti-mouse-HRP antibody (1:2000) and streptavidin-HRP (1.1500) for 20 minutes at room temperature. Membrane was washed 1×15 minutes, 4×5 minutes in 30 ml TBST. The membrane was developed with ECL reagents. The chemiluminescent signal was detected with the Bio-Rad Fluor-S Imager for two to thirty minutes. Samples were quantitated with the Quantity one software.

Oligos for HIS Tag in Secretion Vector

```
                                              (SEQ ID NO: 9)
HIStop   5'-GATCCCATCACCATCATCACCATTAATAGC-3'

(SEQ ID NO: 10)
HISbot   5'-TCGAGCTATTAATGGTGATGATGGTGATGG-3'
```

Construction and Screening of hMFE Library

A random scFv library of the hMFE scFv was created by adapting the nucleotide analogue method from Zaccolo (Zaccolo and Gherardi, 1999). The expression cassette of hMFE was amplified by PCR with the T3 and T7 promoter standard primers. Five mutagenic PCR conditions were used: 250 µM dPTP and 8-oxo-dGTP/5 cycles; 25 µM dPTP and 8-oxo dGTP/10 cycles; 2.5 µM dPTP and 8-oxo-dGTP/ 10 cycles; 25 µM dPTP and 8-oxo-dGTP/20 cycles, 2.5 µM dPTP and 8-oxo-dGTP/20 cycles. Other PCR components were: 1 ng pCThM FE, 250 µM each dNTP, 0.5 µM each primer, 3 units Taq polymerase (Gibco), 1× Gibco PCR buffer supplemented with 2 mM $MgCl_2$. The reaction was cycled as follows: 94° C. minute, 50° C. minute, 72° C. 35 minutes. PCR products from 10 and 20 cycles were isolated on a 1% agarose gel. Four 2200 bp fragments were excised from the gel and purified with the gel purification kit (Qiagen). PCR products from 5 cycles were diluted 1:10 for farther amplification. The PCR fragments were then amplified in the absence of the nucleotide analogues for 25 cycles using Taq polymerase. PCR conditions were identical as those listed above, with the exception of extension time at 72° C. This was changed to 3 minutes and 10 seconds. PCR products were purified using the PCR purification kit (Qiagen). Purified PCR fragments were digested with NheI and BamHI, gel purified, and ligated overnight at 16° C. into pCThM FE. Ligation reactions were transformed into ten aliquots of DH5a-FT cells (Life Technologies). Transformants were pooled and aliquots were plated to determine library size. The diversity was calculated to be $10^5$. The library was amplified in LB/Amp50/Carb50 media at 37° C. and plasmid DNA was purified with the Qiagen Maxi-prep kit. Ten clones were selected for sequencing from the library and the mutagenesis rate was calculated to be 0 2%–5%. Library DNA was transformed into yeast strain EBY100. (Boder and Wittrup, 1997) by the lithium acetate method of Gietz and coworkers (see tto dot trends dot com). Transformants were pooled in SD-CAA (2% dextrose, 0.67% yeast nitrogen base, 1% casamino acids) and aliquots were plated to determine library diversity. The library was passaged twice in SD-CAA to reduce the concentration of untransformed EBY100.

The library was grown to an OD600=10.0 in SD-CAA. Cells were transferred to SG-CAA to an OD600=1.0 and grown for 18 hours at 37° C. The hMFE library was screened by the equilibrium method as described in Boder and Wittrup (Boder and Wittrup, 1998). The optimal biotinylated-CEA concentration was calculated from the mathematical model. Concentrations were selected to screen for 3-fold and 10-fold improvements. Yeast cells displaying mutated hMFE scFv were incubated in 0.35 nM or 0.2 nM biotinylated-CEA at 37° C. Cells were washed with cold PBS/BSA (8 g/L NaCl, 0.2 g/L KCl, 1.44 g/L $Na_2HPO_4$, 0.24 g/L $KH_2PO_4$, 1 mg/ml BSA) and labeled with a 1:100 dilution of the monoclonal antibody 9E10 on ice (Covance). Cells were washed with cold PBS/BSA and labeled with secondary reagents streptavidin-Phycoelythrin (1:100) (Pharmingen) and goat-anti-mouse-FITC (1:50) (Sigma) on ice. Cells were washed with PBS/BSA and resuspended at a concentration of $10^7$ cells/ml and sorted on a Becton Dickinson FACStar flow cytometer (Flow Cytometry Center, MIT Cancer Research Center) with a sort rate of approximately 4000 cells/sec. Cells were collected with gate settings designed to collect the cells displaying the highest PE fluorescent signal (CEA binding) per FITC fluorescent signal (scFvs on surface). Four rounds of sorting and regrowth were performed to isolate a highly enriched (100%) population of improved mutants. Mutants were analyzed from both the $3^{rd}$ and $4^{th}$ round sorts.

Analysis of Clones from Equilibrium Sort

Four individual clones were chosen at random from each of the $3^{rd}$ and $4^{th}$ sorts for analysis by equilibrium titration. For each clone, 10 samples of $10^6$ cells were incubated with varying concentrations of biotinylated-CEA at 37° C. for 1–24 hours. Cells were washed with PBS/BSA and labeled with a 1:100 dilution of the monoclonal antibody 9E10 on ice. Cells were washed and labeled with secondary reagents streptavidin-PE (1:100) and goat-anti-mouse-FITC (1:50). Cells were washed again and resuspended at a concentration of approximately $10^6$ cells/ml for analysis on a Coulter EPICS XL flow cytometer using Expo v.2 software. All clones with improved dissociation constants were selected for sequence analysis. Plasmids were rescued from the yeast cells using the Zymoprep (Zymogen) kit following the manufacture's protocol and transformed into XL1-blue competent cells (Stratagene). E. coli cultures were grown overnight in LB/AMP100 and plasmid DNA was purified using the Qiagen Miniprep kit. Sequencing of the scFv ORF was done using the dideoxy terminator method on a Perkin Elmer. Applied Biosystems Division model 377 DNA sequencer at the MIT Cancer Research Center Polymer Laboratory.

Construction and Screening of hLib2 Library

A second random scFv library based on clones isolated from the first library was constructed by adapting the sexual PCR method of Stemmer (Stemmer, 1994). The expression cassette of improved round one mutants as well as enriched pooled library was amplified with the T3 and T7 promoter standard primers. PCR products (approximately 10 μg) were digested to <200 bp with DNase I. Samples were equilibrated for 5 minutes at 15° C., then digested with 1 unit of DNase I (Boehringer) for 90 seconds at 15° C. DNase I was inactivated by heating at 90° C. for 10 minutes. Samples were purified with the Qiagen Qiax II kit. Five DNase digestion mixtures were used (Table 6), combining equal amounts of each component. Digested products were recombined following the method of Stemmer replacing Taq polymerase with Pfu polymerase and cycling for 45 cycles. Six recombination mixtures were used, one for each of the five digestion mixtures and one combining all five digestion mixtures PCR conditions were as follows 94° C. 3 minutes (1 cycle), 94° C. 1 minute, 55° C. 1 minute, 72° C. 1 minute+5 seconds/cycle (45 cycles); 72° C. 7 minutes (1 cycle). Final amplification was performed with primers (SEQ ID NOS: 10 & 11) nested approximately 50 bp and 100 bp from the ends of the scFv ORF and in the presence of 2.25 mM $MnCl_2$ and 0.375 mM $MgCl_2$ to introduce further mutations PCR products were purified by gel electrophoresis, digested with NheI and BamHI, and ligated into the pCThMFE backbone. A portion of the library (25%) was created by the nucleotide analogue method as described previously. Ligation reactions were transformed into XL10-Gold competent cells (Stratagene), pooled, and aliquots were plated to determine library diversity. The library size was calculated to be $2 \times 10^5$. Library DNA was purified and transformed into EBY100 as above.

The second random hMFE library was selected with a kinetic screen as described in Boder (Boder and Wittrup, 1998). Yeast cells displaying mutant scFv were incubated in 2 nM biotinylated-CEA at 37° C. Cells were washed with cold PBS/BSA and then resuspended in 100-fold excess CEA (approximately 250 nM) and returned to 37° C.

Optimal competition time was calculated from Boder and Wittrup (Boder and Wittrup, 1998); however, this time was not used in order to reduce the length of the experiment. First round competition was 1 day, second round was 1 day, third was 1.2 days, and fourth was 2 days. Cells were washed with PBS/BSA and labeled with a 1:100 dilution of 9E10 (Covance) on ice. Cells were washed in PES/BSA and labeled with secondary reagents as described above. Cells were washed with PBS/BSA and resuspended to a concentration of $10^7$ cells and sorted on a Becton Dickinson FACStar flow cytometer. Four rounds of sorting and regrowth were performed to isolate a highly enriched (100%) population of improved mutants

TABLE 6

| | | DNase Digestion Mixture | | |
|---|---|---|---|---|
| 1 | 2 | 3 | 4 | 5 |
| 3rd sort (0.35 nM) | 3rd sort (0.2 nM) | 3rd sort (0.35 nM) | 3rd sort (0.35 nM) | 3rd sort (0.35 nM) |
| 4th sort (0.35 nM) | 4th sort (0.2 nM) | 4th sort (0.35 nM) | 4th sort (0.35 nM) | 4th sort (0.35 nM) |
| hMFE Library | hMFE Library | 3rd sort (0.2 nM) | m10B | 3rd sort (0.2 nM) |
| | | 4th sort (0.2 nM) | m6B | 4th sort (0.2 nM) |
| | | | m9B | m10B |
| | | | | m9B |
| | | | | m6B |
| | | | | HMFE |
| | | | | hMFE Library |

Nested Primers for Shuffled Amplification

```
                                        (SEQ ID NO: 11)
CGDISP/L    5'-GGCAGCCCCATAAACACACAGTAT-3'

(SEQ ID NO: 12)
CGDISP/R    5'-GTTACATCTACACTGTTGTTATC-3'
```

Analysis of Clones Isolated from Kinetic Sort

Ten individual clones were chosen at random from the 4th sort for off-rate analysis. For each clone, $10^7$ cells were incubated in 2 nM biotinylated-CEA at 37° C. for 3 hours. Cells were washed with PBS/BSA and transferred to microcentrifuge tubes ($10^6$ cells/tube) and incubated in 100-fold excess CEA (Calbiochem) at 37° C. for varying amounts of time. Cells were washed and incubated in a 1:50 dilution of 9E10 (Covance) on ice, then washed and incubated in secondary reagents streptavidin-PE (1:100) and goat-anti-mouse-FITC (1:50) on ice. Cells were washed and resuspended at a concentration of $10^6$ cells/ml for analysis on a Coulter Epics XL flow cytometer. All clones with improved off-rates were selected for sequence analysis. Plasmid rescue and sequencing was performed as described above.

Stability Screen of bMFE Library

The first random hMFE library was also screened for improved stability of the scFv. Cells were induced at 37° C. Yeast cells were incubated in 10 nM biotinylated-CEA at 37° C. Cells were transferred to microcentrifuge tubes, washed with ice cold PBS-BSA, and incubated in a 1:100 dilution of 9E10 (Covance) on ice. Cells were labeled with secondary reagents as described previously. Cells were sorted at a concentration of $10^7$ cells/ml on a Becton Dickinson FACStar flow cytometer. Cells were sorted with gate settings designed to collect the highest FITC signal for the CEA binding population. Three rounds of sorting and regrowth were performed to isolate an enriched population of better-displayed mutants. Sixteen mutants were analyzed from the third sort. For each clone, cells were labeled with 10 mM bio-CEA and 9E10. Six clones with higher display levels were selected for sequence analysis. Plasmids were rescued and sequenced as described previously. The single common stabilizing mutation, $V_L$ W47L, was added back to m10B and m3E with site directed mutagenesis. The primers used are shown below as SEQ ID NOS: 13 & 14.

Primers for W47L Change

```
                                                    (SEQ ID NO: 13)
W47Ltop
5'-GGTAAAAGCCCAAAGTTGTTGATTTATTTGACATCCAACTTGGC-3'
```

```
                                                    (SEQ ID NO: 14)
W47Lbot
5'-GCCAAGTTGGATGTCAAATAAATCAACAACTTTGGGCTTTTACC-3'
```

Nucleotide changes are underlined.

Soluble Production of Mutants

The pCTm10B, pCTm3E, pCTm10B47L, and pCTm3E47L vectors were digested with NheI and BamHI. The digests were isolated on a 1% agarose gel and the 750 bp scFvs were excised from the gel and purified with the Qiagen gel purification kit. The four scFvs were ligated into the MFE23-his vector, which was also digested with NheI and BamHI and gel purified. Insertion of the product was confirmed by restriction digest. The secretion plasmids were transformed into the yeast strain YVH10 as previously described. Soluble production was performed as previously described, with protein induction at 37° C. for 48 hours. Samples were detected by an anti-$his_4$ western.

Construction of Destabilized scFv Library

The two cysteines in the light chain of m3E and m3E47L were changed to valine and alanine, respectively. The Quikchange kit from Stratagene was used to perform site directed mutagenesis, following the manufacturer's protocol. The primers used are shown below as SEQ ID NOS: 15–18. Two random scFv libraries were created based on m3E-$V_L$cysout and m3E-$V_L$cys47L using the nucleotide analogue method. The expression cassette of each scFv was amplified by PCR with the T3 and T7 promoter standard primers. Three mutation PCR conditions were used: 250 μM analogues/5 cycles, 25 μM analogues/12 cycles, 2.5 μM analogues/12 cycles. Amplification, purification, and ligation were performed as described previously. Ligation reactions were transformed into ultramax DH5α-FT cells (Invitrogen). Both libraries were $10^5$ in size. Growth of transformants and plasmid purification were performed as described previously.

Primers for Site-Directed Mutagenesis

```
                                                    (SEQ ID NO: 15)
V_L1CYStop
5'-GATAGATGAAACATCGCTGTTAGCGCATCCTCTAGTGTC-3'
```

```
                                                    (SEQ ID NO: 16)
V_L1CYSbot
5'-GACACTAGAGGATGCGCTAACAGCGATGTTTACTCTATC-3'
```

-continued

```
                                                (SEQ ID NO: 17)
V_L2CYStop
5'-GGATGCTGCAACCTACTATGCCCAGCAAAGGTCCTC-3'

(SEQ ID NO: 18)
V_L2CYSbot
5'-GAGGACCTTTGCTGGGCATAGTAGGTTGCAGCATCC-3'
```

Nucleotide changes made are underlined.

Screening of Destabilized scFv Libraries

For the m3E-$V_L$cysout library, cells were incubated in 5 nM biotinylated-CEA and 1:50 9E10 at 37° C. Cells were washed with cold PBS/BSA and resuspended in a 1:50 dilution of goat-α-mouse-FITC and 1:100 streptavidin-PE and incubated on ice. Cells were washed with cold PBS/BSA and resuspended to a concentration of $10^7$ cells/ml for sorting. For the m3E-$V_L$cys47L library, cells were incubated in 1 nM biotinylated-CEA at 37° C. Cells were washed with PBS/BSA, resuspended in a 1:50 dilution of 9E10 and incubated on ice. Cells were washed with cold PBS/BSA and resuspended in a 1:50 dilution goat-α-mouse-FITC and 1:100 streptavidin-PE and incubated on ice. Cells were washed with cold PBS/BSA and resuspended to a concentration of $10^7$ cells/ml for sorting on a Beckton Dickinson FACStar flow cytometer. Sort windows were set to collect the cells with the highest CEA binding per number of scFvs on the surface for both libraries. Three rounds of sorting and regrowth were performed to isolate a highly enriched population for both sorts. Twenty clones were analyzed from each of the $2^{nd}$ and $3^{rd}$ sorts of the m3E-$V_L$cys47L library. For each clone, cells were labeled with 1 nM biotinylated-CEA at 37° C. and 9E10 on ice. Ten clones with higher display levels and CEA binding were selected for sequence analysis. Twenty clones were analyzed from the $3^{rd}$ sort of the m3E-$V_L$cysout library. For each clone, cells were labeled with 5 nM biotinylated-CEA at 37° C. and 9E10 on ice. Five clones with higher display levels and CEA binding were selected for sequence analysis. Plasmids were rescued and sequenced as described previously.

Construction of More Stable High Affinity Mutant

Four mutations were selected from the destabilized library sorts. The Multi-Quikchange kit and Quikchange kit from Stratagene were used to add these mutations back to hMFE47L, m9B47L, m10B47L, and m3E47L with site directed mutagenesis following the manufacturer's protocol. The primers used to make these changes are shown below as SEQ ID NOS: 19–22. Insertion of the mutations was confirmed by sequence analysis.

Primers Used for High Stability Mutant

```
A13Vbot    5'-CTCTATCGCCAACAGAAACAGACATGGAGCTTGG-3'
           (SEQ ID NO: 19)

N20Ttop    5'-GTTGGCGATAGATGAACCATCGCTTGTAGCGC-3'
           (SEQ ID NO: 20)

S31Ptop    5'-GCGCATCCTCTAGTGTCCCATATATGCACTGG-3'
           (SEQ ID NO: 21)

M78Vtop    5'-GTTTGACTATTAGCTCAGTGCAGCCAGAGGATGC-3'
           (SEQ ID NO: 22)
```

Nucleotide changes are underlined.

Soluble Production of High Stability, High Affinity Mutant

The restabilized hMFE, m9B, m10B, and m3E scFv display vectors were digested with NheI and BamHI. The digests were isolated on a 1% agarose gel and the 750 bp scFv was excised form the gel and purified with the Qiagen gel purification kit. The scFvs were ligated into the MFE23-his vector, which was also digested with NheI and BamHI and gel purified. Insertion of the scFv was confirmed by restriction digest and sequence analysis. The secretion plasmid was transformed into the yeast strain YVH10 as previously described. Soluble production was performed as previously described, with protein induction at 37° C. for 48 hours. Samples were detected by an anti-$his_4$ western.

For large scale production of each of the mutants, a 5 ml culture was grown for 36–48 hours at 30° C. in SD-SCAA (2% dextrose, 0.67% yeast nitrogen base, 1% synthetic casamino acids (ura-, trp-, leu-)). The 5 ml culture was then used to inoculate a 1 L culture, which was grown for 36–48 hours at 30° C. in SD-SCAA. Cells were pelleted and transferred to a 1 L culture of SG-SCAA (2% galactose, 0.67% yeast nitrogen base, 1% casamino acids (ura-, trp-, leu-) supplemented with 0.42 mg/ml of BSA) and induced at 30° C. for 48 hours. The supernatant containing the scFv was concentrated with an Amicon stirred ultrafiltration cell (molecular weight cut-off of 10 kDa) and exchanged 200–1000 fold with column buffer (300 mM NaCl, 50 mM $NaH_2PO_4$, pH=7.9). The scFv was purified from the yeast supernatant using the histidine tag by IMAC (immobilized metal-affinity chromatography). Supernatant was incubated with nickel resin (Qiagen) for 2 hours at room temperature and then loaded onto a column. Resin was washed with five to seven column volumes with wash buffer (300 mM NaCl, 50 mM $NaH_2PO_4$, 20 mM Imidazole, pH=7.9). The scFv was eluted from the column with elution buffer (300 mM NaCl, 50 mM $NaH_2PO_4$, 250 mM Imidazole, pH=7.9). The protein eluted predominantly in the second and third elution fractions. All fractions containing scFv were combined and samples were exchanged with PBS to reduce imidazole concentration to less than 1 mM.

Soluble Binding Assays

In order to assess the stability of the scFvs, a 96-well plate (Immulon 2 HB-Dynex) was coated with an anti-$his_4$ antibody (Qiagen) at a concentration of 10 ug/ml overnight at 4° C. Sample wells were blocked with blocking solution (PBS, 0.02% $NaN_3$, 3% BSA) for 2 hours at room temperature. The plate was washed 4 times with TBST (200 mM NaCl, 50 mM Tris, 0.1% Tween-20, pH=8.0). The scFv sample was incubated at 37° C., 70° C., and 84° C. for 1 hour in binding buffer (PBS, 0.05% Triton x-100, 1 mM PMSF, 0.5 mM Iodacetamide, 2.5 mM EDTA, 0.02% $NaN_3$, 0.1% BSA). Samples were then incubated with 25 nM biotinylated-CEA for 1 hour at 37° C. The scFv/biotinylated-CEA solution was added to the wells and incubated for 1 hour at 37° C. The plate was washed 5 times with TBST. A 1:1000 dilution of streptavidin-Europium (Wallac) in assay buffer was added to the wells and incubated at 4° C. for 30 minutes. The plate was washed 7 times with TBST. Enhancement solution was added to each of the wells and incubated at room temperature for 20 minutes. Fluorescence was measure with a Victor 1420 Multilabel Counter.

Results

Production and Affinity Measurement of MFE-23 and Humanized MFE-23

Two general alternative approaches have been described for humanizing a murine Fv. "Loop grafting" involves substitution of murine CDRs into a homologous human framework, followed by fine tuning of several key framework residues (Baca et al., 1997; Rader et al., 1998).

Figure 13:
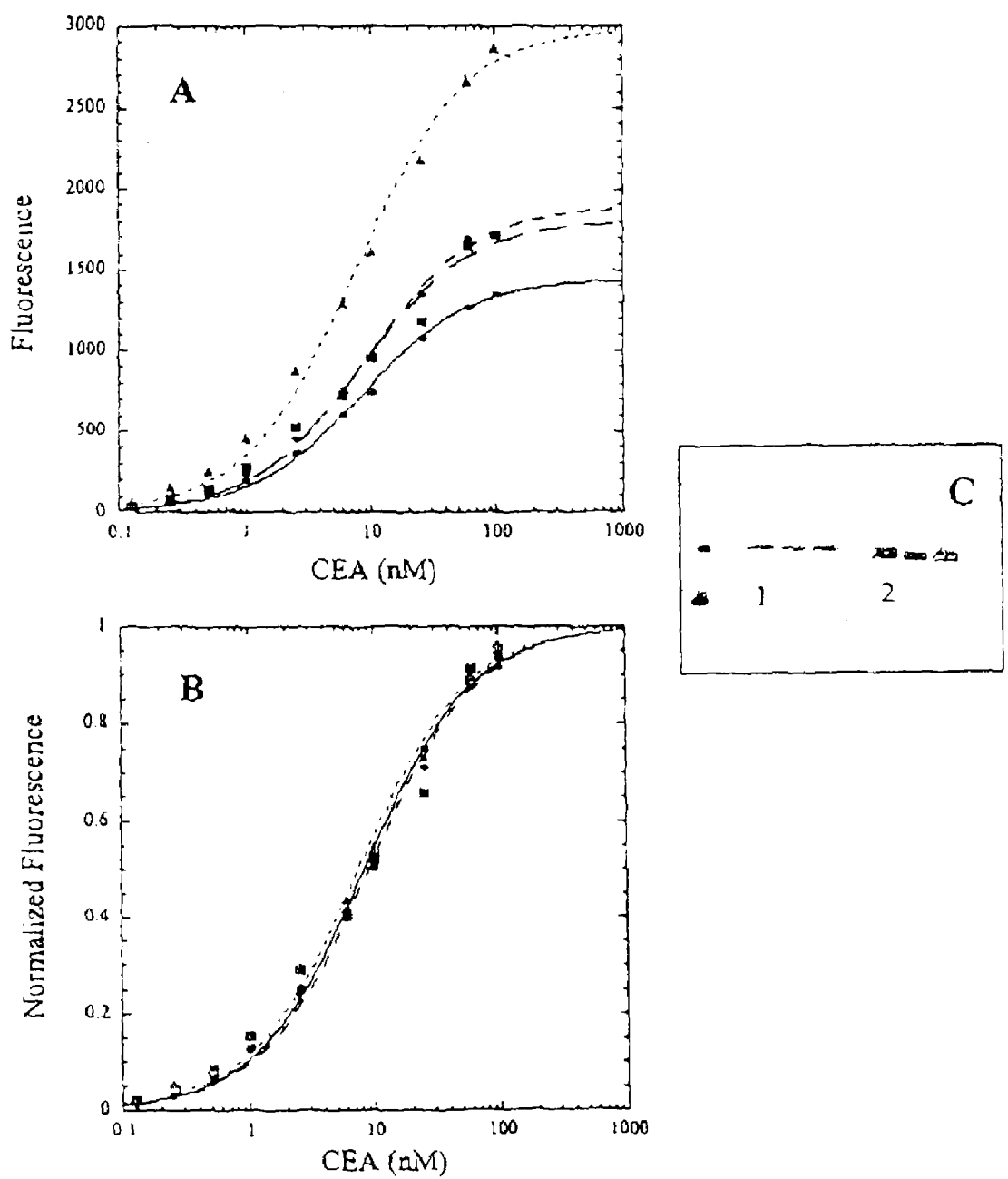
FIG. 13: Titration of MFE-23 and humanized MFE-23 (hMFE) Equilibrium binding constants $K_D$ for CEA at 37° C. A) Plot of CEA binding (measured fluorescence) versus CEA concentration. B) CEA binding (normalized for different display levels) versus CEA concentration. Titrations were performed by labeling yeast cell surface-displayed scFvs with biotinylated-CEA at varying concentrations, and detecting binding with streptavidin-phycoerythrin and flow cytometry (Example 3) hMFE produced at 20° C.

"Resurfacing" involves changing only the solvent exposed residues in a murine framework to their human homologs. A possible pitfall of resurfacing, which has not yet been experimentally reported, is potential retention of T cell epitopes involving buried murine framework residues. However, a benefit of resurfacing is that it generally has less negative impact on antigen binding affinity. The open reading frames of the MFE-23 scFv and humanized MFE-23 (hMFE) scFv were subcloned into the yeast display vector, pCTCON, a variation of pCT302 (Boder and Wittrup, 1997) containing a BamHI site. This construct contains a HA tag N-terminal and a c-myc tag C-terminal of the scFv, to allow detection of scFv expression independent of CEA-binding. The DINA and protein sequences of hMFE are given below as SEQ ID NOS: 3 & 4. Display of the full length fusion of each scFv was confirmed on the yeast surface by labeling with an anti-c-myc antibody. Both scFvs also bound biotinylated carcinoembryonic antigen (CEA). Single chain antibody fragments are often only produced at 20° C. in the yeast display system due to instability of the protein (Boder and Wittrup, 1997). Antibody production was also tested at 37° C. to measure the relative stability of MFE-23 and hMFE. Higher levels of each scFv were detected on the surface (as measured by fluorescence) for production at 37° C. versus 20° C. An equilibrium titration was performed to measure the dissociation constant ($K_D$) of MFE-23 and hMFE at 37° C. Both scFvs bound CEA with a similar $K_D$ (FIG. 13). MFE-23 and hMFE were also produced solubly at 37° C. Resurfacing did not alter CEA binding affinity, and was found to slightly increase soluble expression levels.

hMFE Equilibrium Sort

In order to affinity mature the hMFE scFv, random mutagenesis was performed on the entire scFv with an error rate from 0.2–5%. The error rate was controlled over this range by using the mutagenic nucleotide analogues 8-oxo-dGTP and dPTP and by varying the number of PCR cycles (See above). The resulting library contained $10^5$ clones. The library was transformed into EBY100, the yeast surface display strain, over-sampling the library size by ten-fold in order to insure that the yeast library contained all of the diversity of the DNA library. An equilibrium sort was performed to isolate scFvs with an improved dissociation constant. Optimal selection parameters were calculated as previously described (Equation 8) (Boder and Wittrup, 1998). The optimal labeling concentration was determined based on the $K_D$ of hMFE, the signal to noise ratio ($S_r$), and the desired improvement in the dissociation constant over wild-type ($k_t$ fold decrease in $K_D$).

$$[L]_{opt} = K_{D,hMFE}/(S_r * k_t)^{0.5}$$ Equation 8

The $K_D$ of hMFE was measured to be 8.5 nM on the yeast surface (FIG. 13). The signal to noise ratio was calculated as the mean fluorescence units of CEA labeled at fully saturated versus the mean fluorescence with no CEA. For a 3-fold and 10-fold improvement in the $K_D$, the optimal CEA labeling concentration was calculated to be 0.35 nM and 0.2 nM, respectively. Two labeling concentrations were selected in order to ensure isolation of clones that were modestly improved as well as clones that showed greater improvement. A highly enriched population of improved scFvs was isolated after four sorts with both labeling conditions. The progression of the enrichment for the more stringent conditions, CEA concentration equal to 0.2 nM, is shown in FIG. 14. Four clones were analyzed by equilibrium titration from each of the third and fourth sorts (FIGS. 14D and 14E) and all had an improved dissociation constant. Seven unique clones were isolated (Table 7).

TABLE 7

Mutants from First Equilibrium Library Sort

| | m2B | m5B | m6B | m9B | m10B | m17B | m18B | CDR |
|---|---|---|---|---|---|---|---|---|
| $K_D$ | nd | nd | nd | 0.80 | 0.08 | nd | nd | |
| # times found | 1 | 1 | 1 | 1 | 2 | 1 | 1 | |
| Heavy | | | | | | | | |
| G8 | | | D | | | | | |
| E53 | | | | | | Q | | H2 |
| D101 | | Y | | | | H | | H3 |
| Y102 | | C | | | | | | |
| S113 | | | | | | | G | |
| Light | | | | | | | | |
| F36 | | | | L | | | | |
| S50 | L | L | L | | L | L | L | L2 |
| Q89 | L | | | | | | | |

Six of the seven clones contained the $V_L$S50L mutation in the CDR 2 loop of the light chain. One clone, m10B, contained only the S50L mutation. Since m10B maintains high affinity for CEA when the other mutations are not present, only the S50L change is necessary for the improvement in affinity. The highest affinity clone (m10B) has a dissociation constant of 0.08 nM (FIG. 15A) and an off-rate of $6.0 \times 10^{-6}$ s$^{-1}$ (FIG. 15B). This corresponds to a 100-fold improvement in the affinity and a 200-fold improvement in the off-rate over the wild-type scFv hMFE. The only clone that did not contain the S50L mutation was m9B. It has a dissociation constant of 0.8 nM and an off-rate of $7.5 \times 10^{-5}$ s$^{-1}$ (FIG. 15), which represent a 10-fold and 16-fold improvement over hMFE.

hLib2 Kinetic Library Sort

To improve the affinity further, a second library was made by random mutagenesis and DNA shuffling (hLib2). For random mutagenesis (approximately 25% of the final library), conditions were the same as those used to create the first library. Several different populations were combined for the shuffled portion of the library. These included: the third and fourth sorted populations from the modest and stringent equilibrium sorts, the first hMFE library, hMFE, m9B, and m10B. The resulting library contained $2 \times 10^5$ clones. A kinetic sort was used to isolate clones with a slower off-rate. Optimal selection conditions were calculated as previously described (Equation 9) (Boder and Wittrup, 1998). The optimal competition time was determined based on the off-rate of the best mutant from the first sort (m10B), the signal to noise ratio ($S_r$), and the desired improvement in the off-rate ($k_t$ fold decrease in $k_{off}$).

$$k_{off,m10B}t_{opt} = 0.239 + 2.05 \log k_t + (2.30 - 0.759 k_t^{-1}) \log S_r$$ Equation 9

The $k_{off}$ of m10B was measured to be $6.0 \times 10^{-6}$ s$^{-1}$. The signal to noise ratio was calculated as the mean fluorescence units of CEA labeling with no competition versus the mean fluorescence with no CEA. For a 3-fold improvement in the $k_{off}$, the optimal competition time with non-fluorescent CEA was calculated to be 7 days. In order to reduce the time necessary to isolate improved clones, competition times shorter than the optimal time were selected. Mutants with slower off-rates were isolated by competition with non-fluorescent CEA for 1—3 days (1$^{st}$ sort—1 day; 2$^{nd}$ sort—1 day; 3$^{rd}$ sort—1.2 days, 4$^{th}$ sort—2 days). A highly enriched population was isolated after four sorts. Ten clones were analyzed by competition and all had a slower off-rate. Eight unique clones were isolated (Table 8). Seven of the eight clones contained the $V_L$S50L and $V_L$P36L mutations. The most improved mutant (m3E) has a measured off-rate of $1.2 \times 10^{-6}$ s$^{-1}$ (FIG. 16). m3E is the combination of m9B and m10B from the previous cycle of mutagenesis and screening. The very slow dissociation kinetics for m3E/CEA are expected to correspond essentially to irreversible targeting in vivo (see Discussion below), indicating that further affinity maturation is not warranted.

TABLE 8 hlib2 Library Mutants

| | m1E | m2E | m3E | m4E | m5E | m6E | m7E | m8E | CDR |
|---|---|---|---|---|---|---|---|---|---|
| $k_{off}$ ($10^{-6}$ s$^{-1}$) | | | 1.2 | | | | 1.8 | 2.6 | |
| # times found | 1 | 1 | 2 | 1 | 2 | 1 | 1 | 1 | |
| Heavy | | | | | | | | | |
| E53 | | | | Q | Q | Q | | Q | H2 |
| N54 | | | | | | K | | | H2 |
| F69 | L | | | | | | | | |
| S82b | | F | | | | | | | |
| N93 | | | Y | | | | | | |
| T98 | | | | | | | | A | H3 |
| F100c | | S | | | | | | | H3 |
| Light | | | | | | | | | |
| S24 | | | | | | | N | | |
| F36 | L | L | L | L | L | L | L | | |
| S50 | L | L | L | L | L | L | L | L | L2 |
| S56 | P | | | P | P | | P | P | |
| M78 | | | | | | V | | | |

3.3.2 hMFE Library Stability Sort

Unfortunately, increased affinity appears to directly correlate with decreased expression for the isolated mutant series (FIG. 17). As a practical matter, it was necessary to improve expression yields significantly. In order to accomplish this, a stability screen was performed. A correlation has been previously shown to exist between surface display levels and thermal stability of the protein, as well as soluble protein production (Shusta et al., 2000). The initial hMFE library was sorted for increased display levels of the scFv in the non-affinity matured context. Cells were labeled at a CEA concentration of 5 nM. This concentration was chosen in order to isolate mutants that were improved in display levels only and not in affinity. After three sorts, sixteen clones were analyzed for increased display levels. Six exhibited a 2.5-fold improvement in display, four of which were unique clones (Table 9). All four clones contained the $V_L$W47L mutation, which was responsible for the increased display levels. This mutation was added to the m10B and m3E clones to check if display levels were improved as well. Addition of this mutation increased display levels 2.5 and 1.5-fold, respectively (FIG. 17). Soluble expression levels were also tested. The presence of $V_L$W47L significantly increased production for hMFE, m10B, and m3E (FIG. 17D), however further improvements in expression were still needed.

TABLE 9 hMFE Library Stability Mutants

| | m4G | m8G | m9G | m15G | CDR |
|---|---|---|---|---|---|
| Display Improvement | 2.5 | 2.5 | 2.5 | 2.5 | |
| # times found | 3 | 1 | 1 | 1 | |
| Heavy | | | | | |
| I51 | | | | V | |
| E53 | | | Q | | H2 |
| N93 | | Y | | | |
| Light | | | | | |
| W47 | L | L | L | L | |

Destabilization Followed by Restabilization

Since the most affinity-improved mutant was still not produced at levels comparable to the wild-type scFv hMFE, it was necessary to further improve soluble production for this clone. Removal of the pair of cysteines in either the heavy or light chain causes the loss of the disulfide bond for that fragment and consequently lower stability. Previous work has shown that the cysteines can be replaced with a valine and alanine and then mutated to isolate clones that improve the stability of the scFv in the absence of the disulfide bond. Reintroduction of the disulfide bond will then further stabilize the scFv (Proba et al., 1998). The two cysteines were pairwise removed from the heavy chain or the light chain of m3E and replaced with valine and alanine. Curiously, removal of the $V_H$ cysteines does not significantly alter expression of m3E. By contrast, removal of the $V_L$ cysteines destabilizes m3E significantly (FIG. 18). It can be seen that introduction of W47L restabilizes the disulfide deleted $V_L$, but not back to wild-type levels. With this in mind, two libraries were constructed based on m3E and m3E47L. The new constructs, m3E-cysout and m3E-cys47L, were used as the template for two new libraries. Random mutagenesis was performed on the entire scFv with an estimated error rate from 0.2–3%. The error rate was controlled over this range by using the mutagenic nucleotide analogues 8-oxo-dGTP and dPTP and by varying the number of PCR cycles (See above). Both libraries contained 10$^5$ clones. The libraries were labeled at a CEA concentration of 2.5 nM (m3E-cysout library) and 0.5 nM (m3E-cys47L). A higher CEA concentration was used with the m3E-cysout library because too little CEA binding was detected at the lower concentration. Stabilized clones were isolated by enriching for those cells with the highest display levels and CEA binding. Twenty clones were analyzed from the third sort of the m3E-cysout library. Nineteen were improved over m3E-cysout. Five were sequenced, four of which were unique (Table 10). Forty clones were analyzed for increased display levels and CEA binding from each of the second and third m3E-cys47L library sorts. All forty were improved over m3E-cys47L. Ten of the most improved clones were sequenced, nine of which were unique (Table 10). Mutations that were already present are underlined. Several mutants became stabilized by reverting the F36L affinity mutation back to phenylalanine. This result is consistent with the library being a comprehensive sample of the point mutations since the F36L reversion is a known (albeit trivial and undesirable) stabilizing mutation.

TABLE 10

Stabilized Mutants

| | m1I | m2I | m5I | m7I | m1J | m7J | m16J | m19J | m20J | m31J | m35J | m37J | m40J | CDR |
|---|---|---|---|---|---|---|---|---|---|---|---|---|---|---|
| # times found | 1 | 1 | 1 | 1 | 1 | 1 | 1 | 1 | 1 | 2 | 1 | 1 | 1 | |
| Heavy | | | | | | | | | | | | | | |
| V2 | | A | | | | | | | | | | | | |
| K19 | | | | | | R | | | | | | | | |
| F27 | | | | | | | | | | | | | L | H1 |
| M34 | | | | | | V | | | | | | | | |
| T57 | | | | | | | | | | | | A | | |
| Q64 | | R | | | | | | | | | | | | |
| R83 | | G | | | | | | | | | | | | |
| N93 | | T | | | | | | | | | | | | |
| Y100a | | | | H | | | | | | | | | | H3 |
| F100c | | | S | | | | | | | | | | | H3 |
| Light | | | | | | | | | | | | | | |
| A13 | | | V | | | | | | V | | | | | |
| N20 | | T | | | | | | | | | I | T | | |
| S29 | | | | | | | | | | G | | | | |
| S31 | | P | | | | P | P | | | | | | | L1 |
| F36 | L | L | | L | L | | L | L | L | L | | L | | |
| W47 | | | | L | L | L | L | L | L | L | L | L | L | |
| I48 | | | | | | | | | V | | | | | |
| S50 | L | L | L | L | L | L | L | L | L | L | L | L | L | L2 |
| N53 | | | H | | | | | | | | | | | |
| M78 | V | | | | | | | | | V | | | | |
| L96 | | | | | | | | | | P | | | | L3 |

Creation of a Well-Expressed, High Affinity scFv

Figure 21:
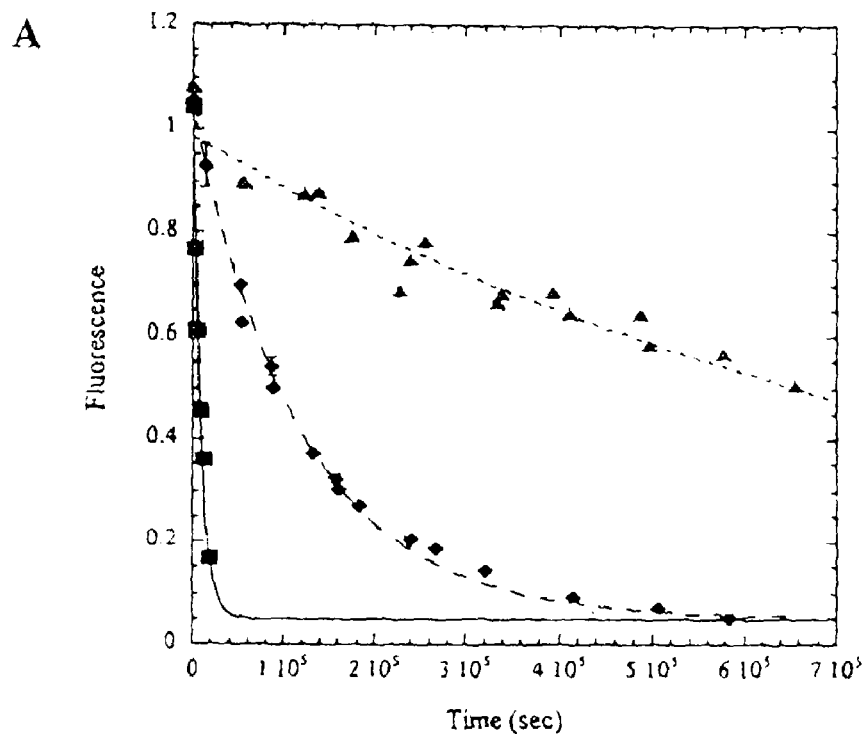
Figure 21:
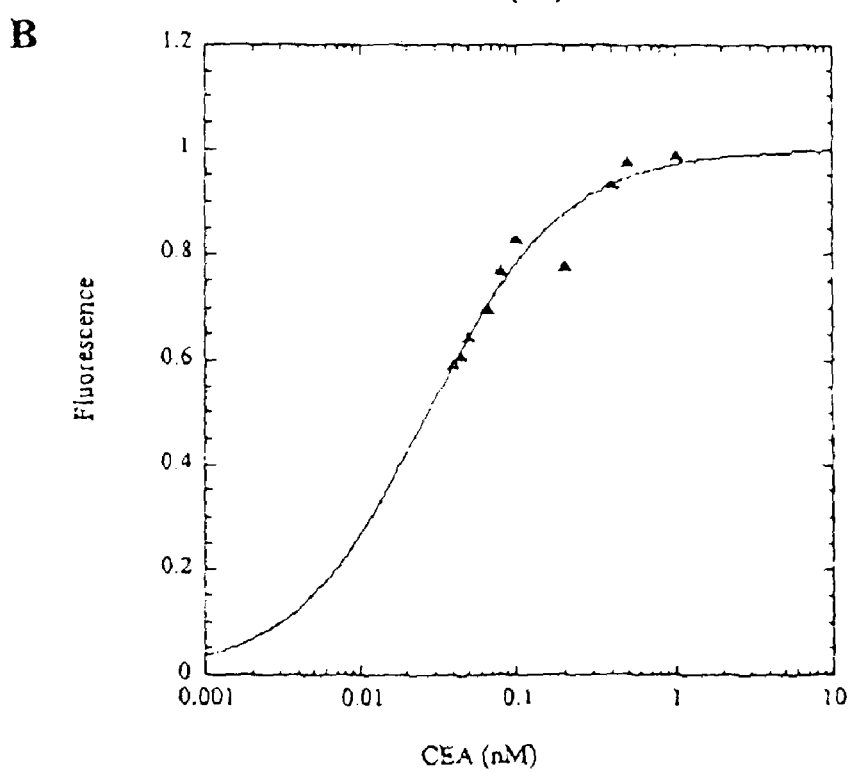

A total of three to four mutations isolated from the stability sort were added back to the affinity mutants containing $V_L$W47L by site-directed mutagenesis in order to create the final series of affinity mutants. These affinity improved clones contained the following additional mutations: m9B—$V_L$N20T, $V_L$S31P, $V_L$W47L, and $V_L$M78V; m10B—$V_L$N20T, $V_L$S31P, $V_L$W47L, and $V_L$M78V; m3E—$V_L$A13V, $V_L$N20T, $V_L$S31P, $V_L$W47L, and $V_L$M78V. The $V_L$N20T, $V_L$S31P, $V_L$W47L, and $V_L$M78V mutations were also added to the hMFE scFv. The DNA and protein sequences are given below as SEQ ID NOS: 5 & 6. Introduction of these mutations increased the display level 4-fold, 5-fold, and 6-fold for m9B, m10B, and m3E, respectively (FIG. 19). The soluble expression level was increased for the series as well. The shMFE scFv is made at approximately 20 mg/L, sm9B~17 mg/L, sm10B~12.5 mg/L, and sm3E is made at approximately 8 mg/L. This level of production for sm3E is a 100-fold improvement over the m3E scFv. In fact, scFv bands are now visible on a coomassie gel, whereas original scFvs were not visible (FIG. 20). The off-rates were relatively unchanged (FIG. 21). The final well-expressed, high affinity scFv has a dissociation constant equal to 30 pM and an off-rate equal to $1.2 \times 10^{-6}$ $s^{-1}$.

Stability of the final mutant was also assessed and compared to the stability of the wild-type hMFE scFv. After incubation at 37° C. for 9 days, yeast displaying sm3E retained approximately 80% binding to CEA. Similar values were obtained for hMFE. The soluble version of the sm3E mutant had comparable stability to the wild-type hMFE scFv at elevated temperatures after restabilization as well (FIG. 22). Since the high affinity mutant without the stabilizing mutations (m3E) is made poorly, a direct comparison between soluble m3E and sm3E cannot be made. However, sm3E does have similar thermal stability properties as hMFE and the soluble expression level is approximately four times higher than hMFE for the well-expressed high affinity mutant.

Construction of T98A Mutants

The T98A mutation was added to hMFE, sm10B, and sm3E with the Quikchange kit from Stratagene using primers T98Atop.

```
                              (SEQ ID NO: 23)
T98Atop    (CGAAGGGACACCAGCTGGTCCTTACTATTTCG
and (SEQ ID NO: 24)
T98Abot    (CGAAATAGTAAGGACCAGCTGGTGTCCCTTCG
```

Insertion of the mutation was confirmed by sequence analysis. Off-rate analysis was performed as previously described at 37° C.

Results

In order to check the contribution of the T98A mutation isolated from previous affinity maturation studies, this mutation was added to the hMFE, sm10B, and sm3E scFvs. Off-rate analysis was performed on the yeast surface at 37° C. for the scFvs with and without T98A. For the wild-type, humanized version (hMFE), addition of this mutation led to a modest 1.5-fold improvement (hMFE: $k_{off}=0.9\pm0.04\times10^{-3}$ $s^{-1}$; hMFE+T98A: $k_{off}=0.6\pm0.02\times10^{-3}$ $s^{-1}$) (FIG. 23). For sm10B and sm3E, addition of T98A led to a small improvement for sm10B (sm10B: $k_{off}=8.2\pm0.4\times10^{-6}$ $s^{-1}$; sm10B+T98A: $k_{off}=6.8\pm0.2\times10^{-6}$ $s^{-1}$) and no improvement for sm3E (sm3E & sm3E+T98A: $k_{off}=1.2\pm0.1\times10^{-6}$ $s^{-1}$) (FIG. 24).

Discussion

In this study, the MFE-23 scFv antibody fragment was engineered to improve tumor targeting through the use of directed evolution and yeast surface display. To accomplish this goal, three properties were addressed: immunogenicity; affinity, and stability. A series of scFvs was engineered that span three orders of magnitude in off-rate and are extremely stable at 37° C. In addition, the likelihood of immunogenicity was reduced via framework resurfacing. As a result, these designed molecules can be tested in a therapeutic setting to reconcile the importance of affinity in tumor targeting.

The current state of the art in antibody engineering is the use of "fully human" antibodies from either transgenic mice (Mendez et al., 1997) or repertoires displayed on phage (Knappik et al., 2000). However, decades of research with classic mouse hybridoma technology has produced many legacy mouse antibodies with interesting binding specificity, such as MFE-23. Rather than abandon these lead molecules, it is of interest to adapt them to reduce immunogenicity via humanization. The effect of resurfacing twenty-eight residues of the MFE-23 scFv on binding affinity was found to be negligible. This result is a major advantage of this humanization technique. The crystal structure or homology model of a murine scFv can be compared to that of a human antibody to look for structural similarity. It is essential to find a human antibody with the greatest domain resemblance so as not to change the antibody framework during humanization. The humanized scFv was also designed with yeast optimal codons. This design characteristic and humanization of the scFv led to increased soluble production levels over the MFE-23 scFv.

In order to affinity mature the hMFE scFv, the entire scFv was subjected to mutagenesis because amino acids not located in the CDR loops can often contribute to affinity gains (Low et al., 1996; Saviranta et al., 1998; Boder et al., 2000; Daugherty et al., 2000). The nucleotide analogues dPTP and 8-oxo-dGTP were used since higher error-rates can be achieved than with conventional error-prone PCR, and higher rates of mutagenesis more effectively search sequence space (Zaccolo and Gherardi, 1999; Daugherty et al., 2000). DNA shuffling was also performed in subsequent steps because random recombination of mutations tends to be more efficient than manual selection and recombination of the changes. The most improved clone (m3E) is simply the combination of $FV_L36L$ and $SV_L50L$ from the previous cycle of mutagenesis and screening. Both libraries constructed in this study were approximately $10^5$ in size, which would be considered small by comparison to phage display libraries. However, the dramatic affinity improvements obtained indicate that size was not a limiting factor in this case. The mutations of interest are both in the light chain. The change that led to the greatest improvement in affinity, $SV_L50L$, is in the CDR 2 loop of the light chain. From inspection of the crystal structure, the side chain of this residue protrudes into the cavity where contact with the antigen may occur. The other mutation that increased the affinity is $FV_L36L$. It is not in a CDR loop and occurs at the interface of the light and heavy chain, directly below this cavity. Its contribution to CEA binding is not as readily apparent as that at position 50. The crystal structure of MFE-23, as well as a homology model of the CEA/MFE-23 interaction, has led to speculation as to the location and importance of certain contact residues (Boehm et al., 2000; Boehm and Perkins, 2000). Most of the CEA contacts in the theoretical model of the complex involve residues located in the CDR loops of the heavy chain. There is a band of six acidic residues in MFE-23 (Asp-H31, Asp-H52, Glu-H53, Asp-H56, Glu-H58, and Glu-L1) that appears to interact with a band of six basic residues in CEA (Boehm and Perkins, 2000). Previous mutational studies have also highlighted the importance of several residues in the H3 loop (Read et al., 1995). The $V_HY100bP$ mutation eradicated binding, a $V_HE53K$ change decreased binding, and the $V_HT98A$ mutation led to a modest improvement in binding. While all six CDR loops were shown to interact with CEA in the homology model, it is possible that the loops of the heavy chain were already optimized for this interaction. While several mutations were isolated which were located in the CDR loops of the heavy chain, they seem to be neutral in effect.

The hMFE scFv was already quite stable at 37° C. prior to affinity maturation. Single chain antibody fragments are often only produced at 20° C. in the yeast display system due to instability of the protein (Boder and Wittrup, 1997). However, higher levels of the hMFE scFv were detected on the surface when produced at 37° C. than at 20° C. Unfortunately, increased affinity appeared to directly correlate with decreased expression for the isolated mutant series. This necessitated screening for higher display of the scFv, which has been shown to correlate with the soluble expression level and thermal stability of the protein (Shusta et al., 2000). The goal of this screen was to engineer the affinity mutants in such a manner as to return soluble expression capacity and thermal stability to at least the level of the hMFE scFv. A total of five stabilizing mutation were selected as significant from the three stability sorts. Four to five of these changes were added to each of the affinity mutants. In the cases where less than five of the changes were incorporated in the stabilized mutants, inclusion of the additional mutations did not confer any greater stability. All of the stabilized mutants contained $V_LN20T$, $V_LS31P$, $V_LW47L$, and $V_LM78V$. Position 20 was resurfaced in the humanization portion of the project to asparagine. The change to threonine was a reversion back to the original MFE-23 residue. It is not unusual in the case of resurfacing to need to selectively change residues back to their original amino acid. The key is to find a balance between the desired goal, humanization in this case, and any potential drawbacks such as a loss in soluble production levels and/or stability. The change to leucine at position 47 was isolated in the first sort and proved to significantly increase soluble production levels and stability for all clones. This mutation was also isolated from the destabilized, cysteine removed library. Position 78 in the light chain is a buried residue in a pocket away from the CDR loops. The change to valine may have created better packing of the side chains within this pocket. In the course of humanization, residues 77,79, and 80 were all changed to the corresponding ones in the human antibody. It is also possible that these three changes dictated the change at position 78. The $V_LS31P$ mutation is located in CDR 1 of the light chain. While inclusion of this change was mildly important for increasing soluble expression levels, it was incorporated to offset small affinity losses as a result of the other changes. The $V_LA13V$ mutation was only included in the stabilized version of m3E. This residue is not solvent exposed, with its side chain facing into the same pocket as position 78. The change from alanine to the larger side chain of valine may also fill a gap within this pocket. It is interesting to note that for the highest affinity mutant, the stabilized version (sm3E) is only six-fold better displayed, but its soluble expression level increased 100-fold from ~0.08 mg/L to 8 mg/L. This difference highlights a caveat to this approach. While the general progression holds that as surface display levels increase, so do soluble expression levels, the magnitude of this improvement is not always proportionally correlated. The high affinity mutant was also improved in its stability characteristics. Yeast cells displaying sm3E retained approximately 80% binding to CEA after incubation at 37° C. for 9 days. The sm3E mutant had comparable stability to the wild-type hMFE scFv at elevated temperatures after restabilization as well. Through the stabilization process, we were able to return the highest affinity mutant to similar thermal stability as the hMFE scFv. Addition of the five stabilizing mutations to the high affinity mutant also increased soluble production levels 4-fold over the wild-type hMFE scFv.

We have created a humanized version of the MFE-23 scFv with higher affinity, stability, and expression levels in yeast. The highest affinity mutant isolated in this study has the slowest off-rate engineered for an antibody against a protein antigen using yeast surface display. It is also amongst the slowest for known antibody-protein antigen interactions. Although we had achieved a similar 'off rate' at room temperature ($1.1 \times 10^{-6}$) with a previous mutation of MFE-23 (CDRH3; Thr 102-Ala), the resulting affinity ($K_D$) of this mutant was only $2.7 \times 10^{-10}$ (Read et al 1995). This is approximately 10× lower overall affinity for CEA than sm3E, due to an accompanying slower 'on rate'. Previous affinity maturation studies against protein antigens using phage display produced several scFvs or Fabs with affinities in the picomolar range (Yang et al., 1995; Schier et al., 1996; Pini et al., 1998). Yang and coworkers engineered a 13 pM Fab ($k_{off}=1.2\times10^{-6}$ s$^{-1}$) against the human envelope glycoprotein gp120 of HIV-1. This was accomplished by CDR walking mutagenesis (Yang et al., 1995). Schier et al. produced a 15 pM scFv ($k_{off}=8.0\times10^{-6}$ s$^{-1}$) against the tumor antigen erbB2 by mutagenesis of the $V_L$ and $V_H$ CDR3 loops (Schier et al., 1996). Pini and coworkers designed a 54 pM scFv ($k_{off}=6.0\times10^{-6}$ s$^{-1}$) against the ED-B domain of fibronectin by mutagenesis of CDR residues (Pini et al., 1998).

Beyond the implications in the field of directed evolution, we have engineered a series of scFvs that may prove valuable in a therapeutic setting. These single chain fragments span three orders of magnitude in off-rate against the tumor associated carcinoembryonic antigen, the greatest with a half-life of approximately 7 days. The work presented in Example 1 above highlights the importance of engineering antibodies against stable cell surface antigens. Success of antibody treatment can be dependent upon the turnover of targeted antigen. Several antigens routinely used as targets cover a broad range of values for internalization or shedding of the antigen. ErbB2, a protein targeted in several forms of cancer, is internalized with a half-life of ~17 minutes (Worthylake et al., 1999). CD20, a B-cell surface antigen used in the treatment of non-Hodgkin's lymphoma, is shed with a half-life of 1 day (Press et al., 1994). The kinetics of CEA synthesis and shedding has been measured previously for human cancer cell lines. Stein et al. (1999) note that a radiolabeled antibody binding CEA on a medullary thyroid carcinoma cell line is only 50% catabolized in 7 days. Shi et al. (1983) examined CEA distribution, synthesis, and release in several different colon cancer cell lines. One can estimate shedding half-lives from the reported net synthesis rates, netrelease rates, and CEA contents for the cell lines SKCO-1, LS174T, and HCT48. These estimates range from 3 to 16 days for the CEA shedding half time in cell culture. The shedding rate is also shown to vary with cell density. Clearly, these indirect estimates on cell lines are at best an estimate of the situation in a micrometastasis or tumor in vivo. Plasma clearance half-lives for CEA have been reported, but in order to convert these to shedding half-lives in vivo one needs synthesis rates and tumor CEA levels, which were generally not determined. However, the available empirical evidence indicates that CEA shedding is a slow process, with a half life on the order of several days to two weeks. By affinity maturing an antibody with a long half-life, comparable to the turnover half-life of the antigen, we have therefore engineered an antibody with effectively irreversible binding to CEA. Because CEA is a stable target with a long half-life, differences in tumor retention for the series of scFvs will be dominated by the off-rate of the antibody and not the half-life of CEA. With this in mind, the molecules designed in this study can be used to confirm the benefits of high affinity antibodies in tumor therapy.

Antibody Sequences

SEQ ID NO: 1/2—Nucleotide and amino acid sequence of MFE-23. This is based on the amino acid sequence of SEQ ID NOS: 1/2 of WO95/15341 but begins from gln 27 of that sequence, which corresponds to position +1 (start heavy chain) of SEQ ID NOS: 3/4 and 5/6 herein. CDRs are shown in bold. Note that the position and length of the CDRs shown below correspond to the position and length of the CDRs shown in SEQ ID NOS: 3/4 and 5/6 herein. Slightly different positions and lengths are in some cases given in WO95/15341)

```
                            +1 start heavy chain

CAGGTGAAACTGCAGCAG

GlnValLysLeuGlnGln              6

TCTGGGGCAGAACTTGTGAGGTCAGGGACCTCAGTCAAGTTGTCCTGC

SerGlyAlaGluLeuValArgSerGlyThrSerValLysLeuSerCys    22

CDR 1

ACAGCTTCTGGCTTCAACATTAAAGACTCCTATATGCACTGGTTGAGG

ThrAlaSerGlyPheAsnIleLysAspSerTyrMetHisTrpLeuArg    38

CDR 2

CAGGGGCCTGAACAGGGCCTGGAGTGGATTGGATGGATTGATCCTGAG

GlnGlyProGluGlnGlyLeuGluTrpIleGlyTrpIleAspProGlu    54
```

-continued

```
AATGGTGATACTGAATATGCCCCGAAGTTCCAGGGCAAGGCCACTTTT
AsnGlyAspThrGluTyrAlaProLysPheGlnGlyLysAlaThrPhe       70
ACTACAGACACATCCTCCAACACAGCCTACCTGCAGCTCAGCAGCCTG
ThrThrAspThrSerSerAsnThrAlaTyrLeuGlnLeuSerSerLeu       86
                          CDR 3
ACATCTGAGGACACTGCCGTCTATTATTGTAATGAGGGGACTCCGACT
ThrSerGluAspThrAlaValTyrTyrCysAsnGluGlyThrProThr      102
GGGCCGTACTACTTTCACTACTGGGGCCAAGGGACCACGGTCACCGTC
GlyProTyrTyrPheAspTyrTrpGlyGlnGlyThrThrValThrVal      118
TCCTCAGGTGGAGGCGGTTCAGGCGGAGGTGGCTCTGGCGGTGGCGGA
SerSerGlyGlyGlyGlySerGlyGlyGlyGlySerGlyGlyGlyGly      134
    +1 start light chain
TCAGAAAATGTGCTCACCCAGTCTCCAGCAATCATGTCTGCATCTCCA
SerGluAsnValLeuThrGlnSerProAlaIleMetSerAlaSerPro      150
                          CDR 1
GGGGAGAAGGTCACCATAACCTGCAGTGCCAGCTCAAGTGTAAGTTAC
GlyGluLysValThrIleThrCysSerAlaSerSerSerValSerTyr      166
ATGCACTGGTTCCAGCAGAAGCCAGGCACTTCTCCCAAACTCTGGATT
MetHisTrpPheGlnGlnLysProGlyThrSerProLysLeuTrpIle      182
    CDR 2
TATAGCACATCCAACCTGGCTTCTGGAGTCCCTGCTCGCTTCAGTGGC
TyrSerThrSerAsnLeuAlaSerGlyValProAlaArgPheSerGly      198
AGTGGATCTGGGACCTCTTACTCTCTCACAATCAGCCGAATGGAGGCT
SerGlySerGlyThrSerTyrSerLeuThrIleSerArgMetGluAla      214
                          CDR 3
GAAGATGCTGCCACTTATTACTGCCAGCAAAGGAGTAGTTACCCACTC
GluAspAlaAlaThrTyrTyrCysGlnGlnArgSerSerTyrProLeu      230
ACGTTCGGTGCTGGCACCAAGCTGGAGCTGAAACGGGCGGCC
ThrPheGlyAlaGlyThrLysLeuGluLeuLysArgAlaAla            244
```

| SEQ ID NO: 3/4—Nucleotide and amino acid sequence of hMFE-23 |
|---|

```
<- - - - HA tag - - - - ->
CCA TAC GAC GTT CCA GAC TAC GCT CTG CAG GCT AGT GGT GGT GGT GGT TCT GGT GGT GGT
 pro  tyr  asp  val  pro  asp  tyr  ala  leu  gln  ala  ser  gly  gly  gly  gly  ser  gly  gly  gly
                                          +1 start heavy chain
GGT TCT GGT GGT GGT GGT TCT GCT AGC CAA GTT AAA CTG GAA CAG TCC GGT GCT GAA GTT
 gly  ser  gly  gly  gly  gly  ser  ala  ser  gln  val  lys  leu  glu  gln  ser  gly  ala  gly  val
                                                                          CDR 1
GTC AAA CCA GGT GCT TCC GTG AAG TTG TCC TGT AAA GCG TCT GGT TTT AAC ATC AAG GAT
 val  lys  pro  gly  ala  ser  val  lys  leu  ser  cyc  lys  ala  ser   gly  phe  asn  ile  lys  asp
```

SEQ ID NO: 3/4—Nucleotide and amino acid sequence of hMFE-23

```
TCG TAT ATG CAT TGG TTG AGA CAA GGG CCA GGA CAA AGA TTG GAA TGG ATT GGC TGG ATT
 ser  tyr met his trp leu arg gln gly pro gly gln arg leu glu trp ile gly trp ile
                                     CDR 2
GAT CCA GAG AAT GGT GAT ACT GAG TAC GCT CCT AAA TTT CAG GGA AAG GCT ACT TTT ACT
 asp pro glu asn gly asp  thr glu tyr ala pro lys phe gln gly lys ala thr phe thr ACC GAC ACT TCC GCT AAT ACC GCA TAC TTG GGC TTA TCT TCC TTG AGA CCA GAG GAC ACT
 thr asp thr ser ala asn thr ala tyr leu gly leu ser ser leu arg pro glu asp thr
                                CDR 3
GCC GTA TAC TAC TGC AAC GAA GGG ACA CCA ACT GGT CCT TAC TAT TTC GAC TAC TGG GGA
 ala val tyr tyr cys asn glu gly  thr pro thr gly pro tyr tyr phe asp  tyr trp gly CAA GGT ACC TTA GTT ACT GTC TCT AGC GGT GGC GGA GGT TCA GGC GGT GGA GGG TCT GGA
 gln gly thr leu val thr val ser ser gly gly gly gly ser gly gly gly gly ser gly
                       +1 start  light chain
GGT GGC GGT AGT GAA AAT GTG CTG ACC CAA TCT CCA AGC TCC ATG TCT GCT TCT GTT GGC
 gly gly gly ser glu asn val leu thr gln ser pro ser ser met ser ala ser val gly
                                     CDR 1
GAT AGA GTA AAC ATC GCT TGT AGC GCA TCC TCT AGT GTC TCA TAT ATG CAC TGG TTT CAA
 asp arg val asn ile ala cys ser ala  ser ser ser val ser  tyr met his trp phe gln
                                         CDR 2
CAG AAG CCA GGT AAA AGC CCA AAG TTG TGG ATT TAT TCG ACA TCC AAC TTG GCT TCT GGA
 gln lys pro gly lys ser pro lys leu trp ile tyr  ser thr ser  asn leu ala ser gly GTC CCT TCA AGG TTT TCT GGT TCC GGC TCA GGA ACC GAT TAT AGT TTG ACT ATT AGC TCA
 val pro ser arg phe ser gly ser gly ser gly thr asp tyr ser leu thr ile ser ser
                                     CDR 3
ATG CAG CCA GAG GAT GCT GCA ACC TAC TAT TGC CAG CAA AGG TCC TCA TAT CCA CTG ACT
 met gln pro glu asp ala ala thr tyr tyr cys gln gln  arg ser ser tyr pro leu  thr
                                                       < - c-myc tag - -
TTC GGG GGT GGA ACG AAG TTG GAA ATC AAG GCT GCA GCC GGA TCC GAA CAA AAG CTT ATT
 phe gly gly gly thr lys leu glu ile lys ala ala ala gly ser  glu gln lys leu ile
 - - - - - - - >
TCT GAA GAG GAC TTG TAA TAG CTC GAG
 ser glu glu sep leu  OCH AMB leu glu
```

Sequence of fusion including HA tag, hMFE scFv, and c-myc tag. CDR loops of hMFE are boxed and in bold. Epitope tags are highlighted with a box.

SEQ ID NO: 5/6—Nucleotide and amino acid sequence of sm3E

```
<  -  -  - HA tag -  -  -  - >
CCA TAC GAC GTT CCA GAC TAC GCT CTG CAG GCT AGT GGT GGT GGT GGT TCT GGT GGT GGT
 pro tyr asp val pro asp tyr ala  leu gln ala ser gly gly gly gly ser gly gly gly
                                        +1  start  heavy chain
GGT TCT GGT GGT GGT GGT TCT GCT AGC CAA GTT AAA CTG GAA CAG TCC GGT GCT GAA GTT
 gly ser gly gly gly gly ser ala ser gln val lys leu glu gln ser gly ala gly val
                                                                       CDR 1
GTC AAA CCA GGT GCT TCC GTG AAG TTG TCC TGT AAA GCC TCT GGT TTT AAC ATC AAG GAT
 val lys pro gly ala ser val lys leu ser cyc lys ala ser  gly phe asn ile lys asp
```

SEQ ID NO: 5/6—Nucleotide and amino acid sequence of sm3E

```
TCG TAT ATG CAT TGG TTG AGA CAA GGG CCA GGA CAA AGA TTG GAA TGG ATT GGC TGG ATT
[ser] tyr met his trp leu arg gln gly pro gly gln arg leu glu trp ile gly trp ile
         CDR 2
GAT CCA GAG AAT GGT GAT ACT GAG TAC GCT CCT AAA TTT CAG GGA AAG GCT ACT TTT ACT
[asp pro glu asn gly asp] thr glu tyr ala pro lys phe gln gly lys ala thr phe thr
ACC GAC ACT TCC GCT AAT ACC GCA TAC TTG GGC TTA TCT TCC TTG AGA CCA GAG GAC ACT
thr asp thr ser ala asn thr ala tyr leu gly leu ser ser leu arg pro glu asp thr
                            CDR 3
GCC GTA TAC TAC TGC AAC GAA GGG ACA CCA ACT GGT CCT TAC TAT TTC GAC TAC TGG GGA
ala val tyr tyr cys asn glu gly [thr pro thr gly pro tyr tyr phe asp] tyr trp gly
CAA GGT ACC TTA GTT ACT GTC TCT AGC GGT GGC GGA GGT TCA GGC GGT GGA GGG TCT GGA
gln gly thr leu val thr val ser ser gly gly gly gly ser gly gly gly gly ser gly
         +1 start   light chain
GGT GGC GGT AGT GAA AAT GTG CTG ACC CAA TCT CCA AGC TCC ATG TCT GtT TCT GTT GGC
gly gly gly ser glu asn val leu thr gln ser pro ser ser met ser VAL ser val gly
                                                            CDR 1
GAT AGA GTA AcC ATC GCT TGT AGC GCA TCC TCT AGT GTC cCA TAT ATG CAC TGG cTT CAA
asp arg val THR ile ala cys ser ala [ser ser ser val PRO] tyr met his trp LEU gln
                                              CDR 2
CAG AAG CCA GGT AAA AGC CCA AAG TTG TGG ATT TAT TtG ACA TCC AAC TTG GCT TCT GGA
gln lys pro gly lys ser pro lys leu LEU ile tyr [LEU thr ser] asn leu ala ser gly
GTC CCT TCA AGG TTT TCT GGT TCC GGC TCA GGA ACC GAT TAT AGT TTG ACT ATT AGC TCA
val pro ser arg phe ser gly ser gly ser gly thr asp tyr ser leu thr ile ser ser
                                                            CDR 3
gTG CAG CCA GAG GAT GCT GCA ACC TAC TAT TGC CAG CAA AGG TCC TCA TAT CCA CTG ACT
VAL gln pro glu asp ala ala thr tyr tyr cys gln gln [arg ser ser tyr pro leu] thr
                                                          < -  c-myc tag  - -
TTC GGG GGT GGA ACG AAG TTG GAA ATC AAG GCT GCA GCC GGA TCC GAA CAA AAG CTT ATT
phe gly gly gly thr lys leu glu ile lys ala ala ala gly ser [glu gln lys leu ile]
- - - - - - - >
TCT GAA GAG GAC TTG TAA TAG CTC GAG
[ser glu glu sep leu] OCH AMB leu glu
```

Sequence of surface display fusion including HA tag, sm3E scFv, and c-myc tag. CDR loops of the scFv are boxed and in bold. DNA changes are shown in lower case letters. Amino acid changes are capitalized and in bold italics. Epitope tags are highlighted with a box.

TABLE 11

Amino Acid Differences Between MFE-23 and hMFE-23

| SEQ ID NO: 2 | Position | SEQ ID NO: 4 |
|---|---|---|
| gln | 5 | glu |
| leu | 11 | val |
| arg | 13 | lys |
| ser | 14 | pro |
| thr | 16 | ala |
| thr | 23 | lys |
| glu | 42 | gly |
| gly | 44 | arg |
| ser | 76 | ala |
| gln | 82 | gly |
| thr | 87 | arg |
| ser | 88 | pro |
| thr | 115 | leu |
| ala | 144 | ser |
| ile | 145 | ser |
| pro | 150 | val |
| glu | 152 | asp |
| lys | 153 | arg |
| thr | 157 | ala |
| thr | 176 | lys |
| ala | 194 | ser |
| ser | 204 | asp |
| arg | 211 | ser |
| glu | 213 | gln |
| ala | 214 | pro |
| ala | 234 | gly |
| leu | 240 | ile |

REFERENCES

Cited in Example 1 (and Elsewhere)

Adams, G. P., Schier, R., McCall, A. M., Simmons, H. H., Horak, E. M., Alpaugh, R. K., Marks, J. D., and Weiner, L. M. (2001). High affinity restricts the localization and tumor penetration of single-chain fv antibody molecules. *Cancer Res*, 61: 4750–5.

Baxter, L. T., Zhu, H., Mackensen, D. G., Butler, W. F. and Jain, R. K. (1995). Biodistribution of monoclonal antibodies: scale-up from mouse to human using a physiologically based pharmacokinetic model. *Cancer Res*, 55: 4611–22.

Beers, R., Chowdhury, P., Bigner, D. and Pastan, I. (2000). Immunotoxins with increased activity against epidermal growth factor receptor vIII-expressing cells produced by antibody phage display. *Clin Cancer Res*, 6: 2835–43.

Cooke, S. P., Pedley, R. B., Boden, R., Begent, R. H. and Chester, K. A. (2002). In vivo tumor delivery of a recombinant single-chain Fv::tumor necrosis factor: a fusion protein. *Bioconjug Chem*, 13: 7–15.

Dvorak, H. F., Brown, L. F., Detmar, M. and Dvorak, A. M. (1995). Vascular permeability factor/vascular endothelial growth factor, microvascular hyperpermeability, and angiogenesis. *Am J Pathol*, 146: 1029–39.

Fujimori, K., Covell, D. G., Fletcher, J. E. and Weinstein, J. N. (1989). Modeling analysis of the global and microscopic distribution of immunoglobulin G, F(ab')2, and Fab in tumors. *Cancer Res*, 49: 5656–63.

Fujimori, K., Covell, D. G., Fletcher, J. E. and Weinstein, J. N. (1990). A modeling analysis of monoclonal antibody percolation through tumors: a binding-site barrier. *J Nucl Med*. 31: 1191–8.

Gerlowski, L. E. and Jain, R. K. (1986). Microvascular permeability of normal and neoplastic tissues. *Microvasc Res*, 31: 288–305.

Jain, R. K. (1999). Transport of molecules, particles, and cells in solid tumors. *Annual Review of Biomedical Engineering*, 1: 241–263.

Juweid, M., Neumann, R., Paik, C., Perez-Bacete, M. J., Sato, J., van Osdol, W. and Weinstein, J. N. (1992). Micropharmacology of monoclonal antibodies in solid tumors: direct experimental evidence for a binding site barrier. *Cancer Res*, 52: 5144–53.

Kuan, C. T., Wikstrand, C. J., Archer, G., Beers, R., Pastan, I., Zalutsky, M. R. and Bigner, D. D. (2000). Increased binding affinity enhances targeting of glioma xenografts by EGFRvIII-specific scFv. *Int J Cancer*, 88: 962–9.

Press, O. W., Howell-Clark, J., Anderson, S. and Bernstein, I. (1994). Retention of B-cell-specific monoclonal antibodies by human lymphoma cells. *Blood*, 83: 1390–7.

Saga, T., Neumann, R. D., Heya, T., Sato, J., Kinuya, S., Le, N., Paik, C. H. and Weinstein, J. N. (1995). Targeting cancer micrometastases with monoclonal antibodies: binding-site barrier. *Proc Natl Acad Sci USA*, 92: 8999–9003.

Schier, R., Bye, J., Apell, G., McCall, A., Adams, G. P., Malmqvist, M., Weiner, L. M. and Marks, J. D. (1996). Isolation of high-affinity monomeric human anti-c-erbB-2 single chain Fv using affinity-driven selection. *J Mol Biol*, 255: 28–43.

Schier, R., McCall, A., Adams, G. P., Marshall, K. W., Merritt, H., Yim, M., Crawford, R. S., Weiner, L. M., Marks, C. and Marks, J. D. (1996). Isolation of picomolar affinity anti-c-erbB-2 single-chain Fv by molecular evolution of the complementarity determining regions in the center of the antibody binding site. *J Mol Biol*, 263: 551–67.

Stein, R., Juweid, M., Mattes, M. J. and Goldenberg, D. M. (1999). Carcinoembryonic antigen as a target for radioimmunotherapy of human medullary thyroid carcinoma: antibody processing, targeting, and experimental therapy with 131I and 90Y labeled MAbs. *Cancer Biother Radiopharm*, 14: 37–47.

Sung, C., Shockley, T. R., Morrison, P. F., Dvorak, H. F., Yarmush, M. L. and Dedrick, R. L. (1992). Predicted and observed effects of antibody affinity and antigen density on monoclonal antibody uptake in solid tumors. *Cancer Res*, 52: 377–84.

Thomas, G. D., Chappell, M. J., Dykes, P. W., Ramsden, D. B., Godfrey, K. R., Ellis, J. R. and Bradwell, A. R. (1989). Effect of dose, molecular size, affinity, and protein binding on tumor uptake of antibody or ligand: a biomathematical model. *Cancer Res*, 49: 3290–6.

van Osdol, W., Fujimori, K. and Weinstein, J. N. (1991). An analysis of monoclonal antibody distribution in microscopic tumor nodules: consequences of a "binding site barrier". *Cancer Res*. 51: 4776–84.

Viti, F., Tarli, L., Giovannoni, L., Zardi, L. and Neri, D. (1999). Increased binding affinity and valence of recombinant antibody fragments lead to improved targeting of tumoral angiogenesis. *Cancer Res*, 59: 347–52.

Weinstein, J. N., Eger, R. R., Covell, D. G., Black, C. D., Mulshine, J., Carrasquillo, J. A., Larson, S. M. and Keenan, A. M. (1987). The pharmacology of monoclonal antibodies. *Ann NY Acad Sci*, 507: 199–210.

Weinstein, J. N. and van Osdol, W. (1992). Early intervention in cancer using monoclonal antibodies and other biological ligands: micropharmacology and the "binding site barrier". *Cancer Res*, 52: 2747s–2751s.

Worthylake, R., Opresko, L. K. and Wiley, H. S. (1999). ErbB-2 amplification inhibits down-regulation and induces constitutive activation of both ErbB-2 and epidermal growth factor receptors. *J Biol Chem*, 274: 8865–74.

Wu, A. M., Chen, W., Raubitschek, A., Williams, L. E., Neumaier, M., Fischer, R., Hu, S. Z., Odom-Maryon, T., Wong, J. Y. and Shively, J. E. (1996). Tumor localization of anti-CEA single-chain. Fvs: improved targeting by non-covalent dimers. *Immunotechnology;* 2: 21–36.

Cited in Example 2 (and Elsewhere)

Baca, M., Presta, L. G., O'Connor, S. J. and Wells, J. A. (1997). Antibody humanization using monovalent phage display. *J Biol Chem*, 272: 10678–84.

Begent, R. H., Verhaar, M. J., Chester, K. A., Casey, J. L., Green, A. J., Napier, M. P., Hope-Stone, L. D., Cushen, N., Keep, P. A., Johnson, C. J., Hawkins, R. E., Hilson, A. J. and Robson, L. (1996). Clinical evidence of efficient tumor targeting based on single-chain Fv antibody selected from a combinatorial library. *Nat Med*, 2: 979–84.

Bidart, J. M., Thuillier, F., Augereau, C., Chalas, J., Daver, A., Jacob, N., Labrousse, F. and Voitot, H (1999). Kinetics of serum tumor marker concentrations and usefulness in clinical monitoring. *Clin Chem*. 45: 1695–707.

Boder, E. T., Midelfort, K. S. and Wittrup, K. D. (2000). Directed evolution of antibody fragments with monovalent femtomolar antigen-binding affinity. *Proc Natl Acad Sci USA*, 97: 10701–5.

Boder, E. T. and Wittrup, K. D. (1997). Yeast surface display for screening combinatorial polypeptide libraries. *Nat Biotechnol*, 15: 553–7.

Boder, E. T. and Wittrup, K. D. (1998). Optimal screening of surface-displayed polypeptide libraries. *Biotechnol Prog*, 14: 55–62.

Boehm, M. K., Corper, A. L., Wan, T., Sohi, M. K., Sutton, B. J., Thornton, J. D., Keep, P. A., Chester, K. A., Begent, R. H. and Perkins, S. J. (2000). Crystal structure of the anti-(carcinoembryonic antigen) single-chain Fv antibody MFE-23 and a model for antigen binding based on intermolecular contacts. *Biochem J*, 346 Pt 2: 519–28.

Boehm, M. K. and Perkins, S. J. (2000). Structural models for carcinoembryonic antigen and its complex with the single-chain Fv antibody molecule MFE23. *FEBS Lett*, 475: 11–6.

Casey, J. L., Keep, P. A, Chester, K. A., Robson, L., Hawkins, R. E. and Begent, R. H. (1995). Purification of bacterially expressed single chain Fv antibodies for clinical applications using metal chelate chromatography. *J Immunol Methods*, 179: 105–16.

Chester, K. A., Begent, R. H. Robson, L., Keep, P., Pedley, R. B., Boden, J. A., Boxer, G., Green, A., Winter, G., Cochet, O. and et al. (1994). Phage libraries for generation of clinically useful antibodies. *Lancet*, 343: 455–6.

Chester, K. A., Bhatia, J., Boxer, G., Cooke, S. P., Flynn, A. A., Huhalov, A., Mayer, A., Pedley, R. B., Robson, L., Sharma, S. K., Spencer, D. I. and Begent, R. H. (2000). Clinical applications of phage-derived sFvs and sFv fusion proteins. *Dis Markers*, 16: 53–62.

Chester, K. A., Mayer, A., Bhatia, J., Robson, L., Spencer, D. I., Cooke, S. P., Flynn, A. A., Sharma, S. K., Boxer, G., Pedley, R. B. and Begent, R. H. (2000). Recombinant anti-carcinoembryonic antigen antibodies for targeting cancer. *Cancer Chemother Pharmacol*, 46: S8–12.

Cooke, S. P., Pedley, R. B., Boden, R., Begent, R. H. and Chester, K. A. (2002). In vivo tumor delivery of a recombinant single-chain fv: tumor necrosis factor: a fusion protein. *Bioconjug Chem*, 13: 7–15.

Daugherty, P. S., Chen, G., Iverson, B. L. and Georgiou, G. (2000). Quantitative analysis of the effect of the mutation frequency on the affinity maturation of single chain Fv antibodies. *Proc Natl Acad Sci USA*, 97: 2029–34.

Gold, P. and Freedman, S. O. (1965). Specific carcinoembryonic antigens of the human digestive system. *J Exp Med*, 122: 467–81.

Graham, R. A., Wang, S., Catalano, P. J. and Haller, D. G. (1998). Postsurgical surveillance of colon cancer: preliminary cost analysis of physician examination, carcinoembryonic antigen testing, chest x-ray, and colonoscopy. *Ann Surg*, 228: 59–63.

Hammarstrom, S. (1999). The carcinoembryonic antigen (CEA) family: structures; suggested functions and expression in normal and malignant tissues. *Semin Cancer Biol*, 9: 67–81.

Hammarstrom, S., Shively, J. E., Paxton, R. J., Beatty, B. G., Larsson, A., Ghosh, R., Bormer, O., Buchegger, F., Mach, J. P., Burtin, P. and et al. (1989) Antigenic sites in carcinoembryonic antigen. *Cancer Res*, 49: 4852–8.

Jackson, H., Bacon, L., Pedley, R. B., Derbyshire, E., Field, A., Osbourn, J. and Allen, D. (1998). Antigen specificity and tumour targeting efficiency of a human carcinoembryonic antigen-specific scFv and affinity-matured derivatives. *Br J Cancer*, 78: 181–8.

Knappik, A., Ge, L., Honegger, A., Pack, P., Fischer, M., Wellnhofer, G., Hoess, A., Wolle, J., Pluckthun, A. and Virnekas, B. (2000). Fully synthetic human combinatonal antibody libraries (HuCAL) based on modular consensus frameworks and CDRs randomized with trinucleotides. *J Mol Biol*, 296: 57–86, Low, N. M., Holliger, P. H. and Winter, G. (1996). Mimicking somatic hypermutation: affinity maturation of antibodies displayed on bacteriophage using a bacterial mutator strain. *J Mol Biol*, 260: 359–68.

Matsuoka, Y., Matsuo, Y., Okamoto, N., Kuroki, M. and Ikehara, Y. (1991). Highly effective extraction of carcinoembryonic antigen with phosphatidylinositol-specific phospholipase C. *Tumour Biol*, 12: 91–8.

Mayer, A., Tsiompanou, E., O'Malley, D., Boxer, G. M., Bhatia, J., Flynn, A. A., Chester, K. A., Davidson, B. R., Lewis, A. A., Winslet, M. C., Dhillon, A. P., Hilson, A. J. and Begent, R. H. (2000). Radioimmunoguided surgery in colorectal cancer using a genetically engineered anti-CEA single-chain Fv antibody. *Clin Cancer Res*, 6: 1711–9.

Mendez, M. J., Green, L. L., Corvalan, J. R., Jia, X. C., Maynard-Currie, C. E., Yang, X. D., Gallo, M. L., Louie, D. M., Lee, D. V., Erickson, K. L., Luna, J., Roy, C. M., Abderrahim, H., Kirschenbaum, F., Noguchi, M., Smith, D. H., Fukushima, A., Hales, J. F., Klapholz, S., Finer, M. H., Davis, C. G., Zsebo, K. M. and Jakobovits, A. (1997). Functional transplant of megabase human immunoglobulin loci recapitulates human antibody response in mice. *Nat Genet*, 15: 146-56.

Nap, M., Hammarstrom, M. L., Bormer, O., Hammarstrom, S., Wagener, C., Handt, S., Schreyer, M., Mach, J. P., Buchegger, F., von Kleist, S. and et al. (1992). Specificity and affinity of monoclonal antibodies against carcinoembryonic antigen. *Cancer Res*, 52: 2329–39.

Nap, M., Mollgard, K., Burtin, P. and Fleuren, G. J. (1988). Immunohistochemistry of carcino-embryonic antigen in the embryo, fetus and adult. *Tumour Biol*, 9: 145–53.

Osbourn, J. K., Field, A., Wilton, J., Derbyshire, E., Earnshaw, J. C., Jones, P. T., Allen, D. and McCafferty, J. (1996). Generation of a panel of related human scFv antibodies with high affinities for human CEA. *Immunotechnology*, 2: 181–96.

Osbourn, J. K., McCafferty, J., Derbyshire, E. J., Waibel, R., Chester, K, Boxer, G. and Allen, D. (1999). Isolation of a panel of human anti-CEA single chain Fv from a large phage display library. *Tumor Targeting*: 150–157.

Pedersen, J. T., Henry, A. H, Searle, S. J., Guild, B. C., Roguska, M. and Rees, A. R. (1994). Comparison of surface accessible residues in human and murine immunoglobulin Fv domains. Implication for humanization of murine antibodies. *J Mol Biol*, 235: 959–73.

Pini, A., Viti, F., Santucci, A., Camemolla, B., Zardi, L., Neri, P. and Neri, D (1998). Design and use of a phage display library. Human antibodies with subnanomolar affinity against a marker of angiogenesis eluted from a two-dimensional gel. *J Biol Chem*, 273: 21769–76.

Prall, F., Nollau, P., Neumaier, M., Haubeck, H. D., Drzeniek, Z., Helmchen, U., Loning, T. and Wagener, C. (1996). CD66a (BGP), an adhesion molecule of the carcinoembryonic antigen family, is expressed in epithelium, endothelium, and myeloid cells in a wide range of normal human tissues. *J Histochem Cytochem*, 44: 35–41.

Press, O. W., Howell-Clark, J., Anderson, S. and Bernstein, I. (1994). Retention of B-cell-specific monoclonal antibodies by human lymphoma cells. *Blood*, 83: 1390–7.

Proba, K., Worn, A., Honegger, A. and Pluckthun, A. (1998). Antibody scFv fragments without disulfide bonds made by molecular evolution. *J Mol Biol*, 275: 245–53.

Rader, C., Cheresh, D. A. and Barbas, C. F., 3rd (1998). A phage display approach for rapid antibody humanization: designed combinatorial V gene libraries. *Proc Natl Acad Sci USA*, 95: 8910–5.

Read, D. A., Chester, K. A., Keep, P. A., Begent, R. H., Pedersen, J. T. and Rees, A. R. (1995). Mutagenesis of single-chain antibody MFE-23 and its effect on affinity for CEA. *Br. J. Cancer*, 71: 57 (abstr. P132).

Roguska, M. A., Pedersen, J. T., Keddy, C. A., Henry, A. H., Searle, S. J., Lambert, J. M., Goldmacher, V. S., Blattler, W. A., Rees, A. R. and Guild, B. C. (1994). Humanization of murine monoclonal antibodies through variable domain resurfacing. *Proc Natl Acad Sci USA,* 91: 969–73.

Saviranta, P., Pajunen, M., Jauria, P., Karp, M., Pettersson, K., Mantsala, P. and Lovgren, T. (1998). Engineering the steroid-specificity of an anti-17beta-estradiol Fab by random mutagenesis and competitive phage panning. *Protein Eng.,* 11: 143–52.

Schier, R., McCall, A., Adams, G. P., Marshall, K. W., Merritt, H., Yim, M., Crawford, R. S., Weiner, L. M., Marks, C. and Marks, J. D. (1996). Isolation of picomolar affinity anti-c-erbB-2 single-chain Fv by molecular evolution of the complementarity determining regions in the center of the antibody binding site: *J. Mol Biol,* 263: 551–67.

Shi, Z. R., Tsao, D. and Kim, Y. S. (1983). Subcellular distribution, synthesis, and release of carcinoembryonic antigen in cultured human colon adenocarcinoma cell lines. *Cancer Res,* 43: 4045–9.

Shusta, E. V., Holler, P. D., Kieke, M. C., Kranz, D. M. and Wittrup, K. D. (2000). Directed evolution of a stable scaffold for T-cell receptor engineering. *Nat Biotechnol,* 18: 754–9.

Shusta, E. V., Kieke, M. C., Parke, E., Kranz, D. M. and Wittrup, K. D. (1999). Yeast polypeptide fusion surface display levels predict thermal stability and soluble secretion efficiency. *J Mol Biol,* 292: 949–56.

Shusta, E. V., Raines, R. T., Pluckthun, A. and Wittrup, K. D. (1998). Increasing the secretory capacity of *Saccharomyces cerevisiae* for production of single-chain antibody fragments. *Nat Biotechnol,* 16: 773–7.

Stein, R., Juweid, M., Mattes, M. J. and Goldenberg, D. M. (1999). Carcinoembryonic antigen as a target for radioimmunotherapy of human medullary thyroid carcinoma: antibody processing, targeting, and experimental therapy with 131I and 90Y labeled MAbs. *Cancer Biother Radiopharm,* 14: 37–47.

Stemmer, W. P. (1994). Rapid evolution of a protein in vitro by DNA shuffling. *Nature,* 370: 389–91.

VanAntwerp, J. (1999). *Affinity Maturation of the D1.3 Antibody Using Yeast Surface Display and Flow Cytometry.* PhD Thesis, Department of Chemical Engineering, University of Illinois, Urbana-Champaign Williams, A. F. and Barclay, A. N. (1988). The immunoglobulin superfamily—domains for cell surface recognition. *Annu Rev Immunol,* 6: 381–405.

Willuda, J., Honegger, A., Waibel, R., Schubiger, P. A., Stahel, R., Zangemeister-Wittke, U. and Pluckthun, A. (1999). High thermal stability is essential for tumor targeting of antibody fragments engineering of a humanized anti-epithelial glycoprotein-2 (epithelial cell adhesion molecule) single-chain Fv fragment. *Cancer Res,* 59: 5758–67.

Worthylake, R., Opresko, L. K. and Wiley, H. S. (1999), ErbB-2 amplification inhibits down-regulation and induces constitutive activation of both ErbB-2 and epidermal growth factor receptors. *J Biol Chem,* 274: 8865–74.

Yang, W. P., Green, K., Pinz-Sweeney, S., Briones, A. T. Burton, D. R. and Barbas, C. F., 3rd (1995). CDR walking mutagenesis for the affinity maturation of a potent human anti-HIV-1 antibody into the picomolar range. *J Mol Biol,* 254: 392–403

Zaccolo, M. and Gherardi, E. (1999). The effect of high-frequency random mutagenesis on in vitro protein evolution: a study on TEM-1 beta-lactamase. *J Mol Biol,* 285: 775–83.

Read, D. A., Chester, K. C., Keep, P. A., Begent, R. H. J., Pedersen, J. T. & Rees, A. R. Mutagenesis of a single-chain antibody MFE-2323 and its effect on affinity for CEA. Br. J. Cancer, 71: Supplement XXIV, 57, 1995.

---

The invention claimed is:

1. An isolated antibody specific to carcinoembryonic antigen (CEA) with a dissociation constant of less than 5.0 nM for said antigen and comprising the following six CDRs:
   (a) Heavy Chain CDR 1: gly phe asn ile lys asp ser (from 55 to 61 of SEQ ID NO:6);
   (b) Heavy Chain CDR 2: asp pro glu asn gly asp (from 81 to 86 of SEQ ID NO:6);
   (c) Heavy Chain CDR 3: thr pro thr gly pro tyr tyr phe asp (from 129 to 137 of SEQ ID NO:6);
   (d) Light Chain CDR 1: (i) ser ser ser val pro (from 190 to 194 of SEQ ID NO:6), or
       (ii) ser ser ser val ser (from 161 to 165 of SEQ ID NO:2);
   (e) Light Chain CDR 2: leu thr ser (from 213 to 215 of SEQ ID NO:6);
   (f) Light Chain CDR 3: arg ser ser tyr pro leu (from 254 to 259 of SEQ ID NO:6).

2. The antibody of claim 1 which binds CEA with a dissociation halftime of one day or more at 37° C.

3. The antibody of claim 1 which is an scFv.

4. The antibody of claim 1 having an antitumor agent or a detectable label attached thereto.

5. A composition comprising an antibody of claim 1 and a carrier.

6. A pharmaceutical composition comprising an antibody of claim 1 and a pharmaceutically acceptable carrier.

* * * * *

UNITED STATES PATENT AND TRADEMARK OFFICE
CERTIFICATE OF CORRECTION

PATENT NO. : 7,232,888 B2
APPLICATION NO. : 10/609671
DATED : June 19, 2007
INVENTOR(S) : Begent et al.

Page 1 of 1

It is certified that error appears in the above-identified patent and that said Letters Patent is hereby corrected as shown below:

Title Page Item (73), Assignee, insert before "Massachusetts Institute of Technology, Cambridge, MA (US)" -- Cancer Research Technology Limited, London (GB); --.

Signed and Sealed this

Fourth Day of May, 2010

David J. Kappos
*Director of the United States Patent and Trademark Office*